US008173160B2

(12) United States Patent
Schramm et al.

(10) Patent No.: US 8,173,160 B2
(45) Date of Patent: May 8, 2012

(54) COMPOSITIONS COMPRISING EDIBLE OILS AND VITAMINS AND/OR MINERALS AND METHODS FOR MAKING THE COMPOSITIONS

(75) Inventors: Jack H. Schramm, Gordonsville, VA (US); James W. McGrath, Jr., Keswick, VA (US)

(73) Assignee: PBM Pharmaceuticals, Inc., Charlottesville, VA (US)

(*) Notice: Subject to any disclaimer, the term of this patent is extended or adjusted under 35 U.S.C. 154(b) by 527 days.

(21) Appl. No.: 11/579,527

(22) PCT Filed: May 18, 2005

(86) PCT No.: PCT/US2005/017413
§ 371 (c)(1),
(2), (4) Date: Nov. 3, 2006

(87) PCT Pub. No.: WO2005/112654
PCT Pub. Date: Dec. 1, 2005

(65) Prior Publication Data
US 2008/0274175 A1 Nov. 6, 2008

Related U.S. Application Data

(63) Continuation-in-part of application No. 11/040,953, filed on Jan. 21, 2005, now Pat. No. 8,075,910.

(60) Provisional application No. 60/572,787, filed on May 20, 2004, provisional application No. 60/584,655, filed on Jun. 30, 2004.

(51) Int. Cl.
*A61K 9/48* (2006.01)
*A61K 31/20* (2006.01)
*A61K 31/59* (2006.01)
*A61K 31/355* (2006.01)
*A61K 31/714* (2006.01)
*A61K 31/44* (2006.01)
*A61K 31/4985* (2006.01)
*A61P 43/00* (2006.01)

(52) U.S. Cl. ........ 424/456; 514/558; 514/167; 514/458; 514/52; 514/345; 426/601

(58) Field of Classification Search .................. 424/401, 424/433, 439, 451, 456, 490, 522, 523, 725, 424/590, 601; 514/170, 26, 411, 453
See application file for complete search history.

(56) References Cited

U.S. PATENT DOCUMENTS

| | | | |
|---|---|---|---|
| 2,348,503 A | 5/1944 | Taylor | |
| 2,562,840 A | 7/1951 | Caldwell | |
| 2,720,463 A | 10/1955 | Stirn et al. | |
| 3,376,199 A | 4/1968 | Leonard et al. | 167/83 |
| 3,427,378 A | 2/1969 | Henderson et al. | 424/14 |
| 3,553,329 A | 1/1971 | Nelson et al. | 424/321 |
| 3,861,941 A | 1/1975 | Brockett | 117/36.2 |
| 4,016,254 A | 4/1977 | Seager | 424/33 |
| 4,154,820 A | 5/1979 | Simoons | 424/175 |
| 4,260,626 A | 4/1981 | Carr et al. | 424/273 |
| 4,454,125 A * | 6/1984 | Demopoulos | 514/52 |
| 4,534,467 A | 8/1985 | Rathbun | |
| 4,623,488 A | 11/1986 | Takao | |
| 4,631,284 A | 12/1986 | Salpekar et al. | 514/277 |
| 4,792,418 A * | 12/1988 | Rubin et al. | 554/186 |
| 4,843,095 A * | 6/1989 | Rubin | 514/558 |
| 4,913,921 A | 4/1990 | Schroeder et al. | |
| 4,915,965 A | 4/1990 | Tanaka | 426/282 |
| 4,931,284 A | 6/1990 | Ekman et al. | 424/450 |
| 4,987,031 A | 1/1991 | Tatematsu et al. | 428/402.2 |
| 5,275,821 A | 1/1994 | Torosian | 424/456 |
| 5,346,709 A | 9/1994 | Myhre | |
| 5,374,657 A * | 12/1994 | Kyle | 514/547 |
| 5,434,183 A | 7/1995 | Larsson-Backstrom | |
| 5,494,678 A | 2/1996 | Paradissis et al. | 424/439 |
| 5,525,355 A | 6/1996 | Brown et al. | 424/456 |
| 5,563,129 A | 10/1996 | Masuya et al. | |

(Continued)

FOREIGN PATENT DOCUMENTS

CN 1225837 8/1999

(Continued)

OTHER PUBLICATIONS

Katan et al. Mayo Clinic Proceddings, 2003; 78:965-978.*
"Efficacy and safety of plant stanols and sterols in the management of blood cholestrol levels" Katan et al. Mayo Clinic Proceedings, 2003, 78, 965-978.*
"Effecacy and safty of plant stanols and sterols in the management of blood cholesterol levels", Katan et al., Mayo Clinic Proceedings, 2003, 78:965-978.*
Katan et al. Efficiency and Safety of Plant Stanols and Sterols in the Management of Blood Cholestrol Levels, Mayo Clinic Proceedings, 2003, 78: 965-978.*
Farooqui, Akhlaq A. Beneficial Ehhects of Fish Ol on Human Brain. Springer Dordrecht Heidelberg London New York, 2009. p. 6.*
"Definition of including": Morris, William "The American Heritage Dictionary", 2nd College Edition, Boston, Houghton Mifflin Company, 1982.*

(Continued)

*Primary Examiner* — Ernst Arnold
*Assistant Examiner* — Hong Yu
(74) *Attorney, Agent, or Firm* — Locke Lord LLP; Peter J. Fallon; David G. Green

(57) ABSTRACT

The invention provides compositions for an administration to a mammal orally or in a suppository that include one or more edible oils (preferably including one or more omega-3 fatty acids), one or more plant stanols, phytosterols, or esters thereof, and admixed in the one or more edible oils one or more water-soluble vitamins and/or minerals, for example, vitamins B6, B9 and/or B12. The invention also provides a method of making the compositions comprising mixing the foregoing components to form a suspension or emulsion of the vitamins and/or minerals in the edible oils. The mixture can be inserted into hollow soft or hard capsules, gelcaps or caplets. The edible oils can coat particles of the water-soluble vitamins and/or minerals, which may provide them with an improved absorption in the body due to an increased resistance to degradation in the acidic environment of the stomach.

108 Claims, No Drawings

U.S. PATENT DOCUMENTS

| | | | |
|---|---|---|---|
| 5,571,441 A | 11/1996 | Andon et al. ............... 252/1 |
| 5,770,225 A | 6/1998 | Parekh et al. ............ 424/456 |
| 5,869,084 A | 2/1999 | Paradissis et al. ........ 424/439 |
| 5,906,833 A | 5/1999 | Klatz ....................... 424/468 |
| 5,916,591 A | 6/1999 | Bierdel-Willkommen et al. ......................... 424/456 |
| 5,919,482 A | 7/1999 | Marttila et al. ........... 424/456 |
| 5,925,381 A | 7/1999 | Boyle et al. ............... 424/499 |
| 5,925,669 A * | 7/1999 | Katz et al. ................. 514/449 |
| 6,077,531 A | 6/2000 | Salin-Drouin ............. 424/451 |
| 6,096,317 A * | 8/2000 | Desantis et al. ........... 424/730 |
| 6,096,338 A | 8/2000 | Lacy et al. ................. 424/455 |
| 6,190,680 B1 * | 2/2001 | Sakurada et al. .......... 424/401 |
| 6,190,694 B1 | 2/2001 | Mizushima et al. ....... 424/451 |
| 6,190,702 B1 | 2/2001 | Takada et al. ............. 424/501 |
| 6,267,985 B1 * | 7/2001 | Chen et al. ................ 424/451 |
| 6,280,767 B1 | 8/2001 | Sano ......................... 424/456 |
| 6,365,181 B1 * | 4/2002 | Matthews ................. 424/451 |
| 6,376,461 B1 | 4/2002 | Igari et al. ................... 514/2 |
| 6,413,463 B1 | 7/2002 | Yamamoto ................ 264/301 |
| 6,433,025 B1 | 8/2002 | Lorenz ..................... 514/725 |
| 6,506,406 B1 | 1/2003 | Shioya ...................... 424/451 |
| RE38,009 E | 2/2003 | Garnett et al. ............. 424/451 |
| 6,534,093 B1 | 3/2003 | Thosar ...................... 424/489 |
| 6,541,025 B1 | 4/2003 | Kershman et al. ......... 424/439 |
| 6,544,553 B1 | 4/2003 | Hsia et al. ................. 424/465 |
| 6,551,615 B1 | 4/2003 | Iyer .......................... 424/456 |
| 6,569,445 B2 | 5/2003 | Manning et al. ........... 424/439 |
| 6,576,253 B2 | 6/2003 | Manning et al. ........... 424/439 |
| 6,808,725 B2 | 10/2004 | Bailey et al. |
| 6,838,091 B2 | 1/2005 | Lipari et al. .............. 424/451 |
| 2002/0035087 A1 * | 3/2002 | Barclay ....................... 514/52 |
| 2003/0012797 A1 | 1/2003 | Ishikawa et al. |
| 2003/0021839 A1 | 1/2003 | Draisey |
| 2003/0072797 A1 * | 4/2003 | Guinez et al. ............. 424/450 |
| 2003/0072808 A1 | 4/2003 | Thosar et al. |
| 2004/0052922 A1 * | 3/2004 | Pistolesi ................... 426/601 |

FOREIGN PATENT DOCUMENTS

| | | |
|---|---|---|
| CN | 1248451 | 3/2000 |
| CN | 1284379 | 2/2001 |
| CN | 1301556 | 7/2001 |
| CN | 1317323 | 10/2001 |
| CN | 1325688 | 12/2001 |
| EP | 1 163 901 A1 | 12/2001 |
| EP | 0 711 152 B1 | 12/2002 |
| FR | 2 627 671 | 9/1989 |
| FR | 2 639 797 | 6/1990 |
| GB | 2 028 655 A | 3/1980 |
| JP | 59157018 | 9/1984 |
| JP | 61282054 | 12/1986 |
| JP | 4082827 | 3/1992 |
| JP | 2002188095 | 7/2002 |
| JP | 2003073230 | 12/2003 |
| WO | WO 92/00066 | 1/1992 |
| WO | WO 95/09614 | 4/1995 |
| WO | WO 95/31972 | 11/1995 |
| WO | WO 02/28365 A2 | 4/2002 |
| WO | WO 02/052955 A1 * | 11/2002 |
| WO | WO 03/013550 A1 | 2/2003 |

OTHER PUBLICATIONS

Policosanol: Wikipedia, retrieved from internet http://en.wikipedia.org/wiki/Policosanol. Retrived on Jun. 28, 2011.*

U.S. Appl. No. 60/584,655, Schramm et al., filed Jun. 30, 2004.

U.S. Appl. No. 60/572,787, Schramm et al., filed May 20, 2004.

U.S. Appl. No. 10/144,641, Manning et al., filed May 13, 2002.

U.S. Appl. No. 10/340,088, Manning et al., filed Jan. 10, 2003.

U.S. Appl. No. 11/040,953, Schramm et al., filed Jan. 21, 2005.

Physician's Desk Reference (49$^{th}$ Edition, 1995), p. 1264.

Abdul W. Basit et al., "The Effect of Polyethylene Glycol 400 on Gastrointestinal Transit: Implications for the Formulation of Poorly-Water Soluble Drugs," Pharmaceutical Research (USA), vol. 18, 1146-1150 (2001).

Agnes I. Veldkamp et al., "Steady-State Pharmacokinetics of Twice Daily Dosing of Saqinavir Plus Ritonavir in HIV-1 Infected Individuals," Journal of Acquired Immune Deficiency Syndrome 27(4), 344-349 (2001).

Raquel D. Petry, "The Influence of Adjuvants and Filling Method on Characteristics of Hard Gelatin Capsules Containing Theophylline," Revista Brasileira de Farmacia 79(¾), 99-103 (1998).

M. A. Shehab et al., "Studies on the In Vitro Release of Ibuprofen from Polyethylene Glycol-Polyvinyl Acetate Mixtures Liquid Filled into Hard Gelatin Capsules," Drug Dev. Ind. Pharm. 22, No. 7, 645-51 (1996).

L. Conings et al., "Stability Study of Cimetidine 200 mg and Cimetidine 400 mg Capsules," Farmaceutisch Tijdschrift voor Belgie (Belgium), vol. 73, 2-21 (Sep. 1996).

Rokia Abdallah et al., "Liquid Chromatographic Determination of Rutin and Ascorbic acid-Binary Mixture in Pharmaceutical Preparations," Journal of Liquid Chromatography 16 (18), 4107-4116 (1993).

Terrance C. Dahl et al., "Feasibility of Manufacturing a Solid Dosage Form using a Liquid Nonvolatile Drug Carrier: a Physiocochemical Characterization," Drug Development and Industrial Pharmacy 16(12), 1881-1891 (1990).

Yalcin Topaloglu, "A Hard Gelatin Capsule Formulation for Amphotalide," Acta Pharmaceutica Turcica 32(1), 11-16 (1990).

A. M. Hannula, "Release of Ibuprofen from Hard Gelatin Capsule Formulations. Effect of Modern Disintegrants," Acta Pharm. Fenn. 98, No. 3, 189-96 (1989).

R. A. Kensley et al., "Multidimensional Column-Switching Liquid Chromatographic Method for Dissolution Testing of Enprostil Soft Elastic Gelatin Capsules," J. Pharm. Sci. 75, No. 10, 999-1002 (1986).

W. Pfeifer et al., "Investigations of the Frequency and Causes of Dosage Errors During the Filling of Hard Gelatin Capsules. 2$^{nd}$ Comm.; Dosage Errors During the Filling of Pellets into Hard Gelatin Capsules," Drugs Made Ger. 29, No. 4, 217-218, 220, 1986.

A. T. M. Serajuddin et al., "Water Migration from Soft Gelatin Capsule Shell to Fill Material and its Effect on Drug Solubility," J. Pharm. Sci. 75, No. 1, 62-64 (1986).

W. Pfeifer et al., "Untersuchugen zur Haufigkeit und Ursachen von Fehldosierungen bei der Abfullung von Hartgelatinekapseln," Pharm. Ind. 8, 860-63 (1984).

W. Pfeifer et al., "Untersuchugen zur Haufigkeit und Ursachen von Fehldosierungen bei der Abfullung von Hartgelatinekapseln," Pharm. Ind. 4, 423-425 (1984).

P. A. Mura et al., "In Vitro Study of Some Factors Affecting the Diffusion of Oxytetracycline Hydrochloride from Hard Gelatin Capsules," Bollettino Chimico Farmaceutico 123 (7), 344-51 (1984).

Tachio Byoin et al., "Pharmaceutical Study on Ubidecarenone Soft Gelatin Capsule," Byoin Yakugaku 9(3), 273-7 (1983).

Dieter Steinbach et al, "Studies on the Pharmaceutical and Biological Availability of Diazepam Drug Preparations. Part I. Pharmaceutical Availability," Pharmazeutische Zeitung 125(27), 1297-9 (1980).

K. C. James et al., "Availability of Tritium from Nonaqueous Solutions of [1,2-3H]Methyltestosterone, Administered Orally to Rats," Journal of Pharmacy and Pharmacology 32(12), 810-814 (1980).

J.M. Newton et al., "The Influence of Additives on the Presentation of a Drug in Hard Gelatin Capsules," Journal of Pharmacology 29(5), 294-7 (1977).

Foo S. Hom, "Separation and Ultraviolet Absorbance Techniques for Determining Dihydrotachysterol in Pharmaceutical Preparations," Journal—Association of Official Analytical Chemists 60(1), 48-51 (1977).

www.allabout-solgar-vitamins.com, May 12, 2003 (2 pages).

www.bioceuticsinternational.com/products/epo090.htm, May 12, 2003 (2 pages).

www.worldwideshoppingmall.co, May 12, 2003 (2 pages).

www.vitapure.com, May 12, 2003 (1 page).

www.healthaid.co, May 12, 2003 (4 pages).

http://vitaminlady.com/Jarrow/Allcaps.asp, May 12, 2003 (2 pages).

www.health-store.co.uk, May 12, 2003 (2 pages).

www.vitamer.com/vit_ad.asp, May 12, 2003 (4 pages).

www.vitaminretailer.com, May 12, 2003 (6 pages).

www.health.egnet.net, May 12, 2003 (4 pages).

www.egyfit.com, May 12, 2003 (4 pages).

International Search Report which was cited in a corresponding PCT counterpart application (PCT/US2005/017413), completed on Jun. 13, 2008 and published on Apr. 2, 2009.

International Preliminary Report on Patentability and a Written Opinion of the International Searching Authority which was cited in a corresponding PCT counterpart application (PCT/US2005/017413), completed on Jun. 13, 2008 and issued on Mar. 3, 2009.

DHA as Brain Food, http://web.archive.org/wb/20010827172018/http:///www.askdrsears.com/html/4/t040900.asp, accessed online May 17, 2009.

Dr. Decuypere's Nutrient Chart, Fruit Chart.

\* cited by examiner

COMPOSITIONS COMPRISING EDIBLE OILS AND VITAMINS AND/OR MINERALS AND METHODS FOR MAKING THE COMPOSITIONS

This application is a continuation-in-part patent application of non-provisional patent application U.S. Ser. No. 11/040,953, filed on Jan. 21, 2005 now U.S. Pat. No. 8,075,910, which is a utility patent application that was filed from, and claims the benefit of, prior Provisional Patent Application U.S. Ser. No. 60/572,787, filed on May 20, 2004 ("the first provisional patent application"), and prior Provisional Patent Application U.S. Ser. No. 60/584,655, filed on Jun. 30, 2004 ("the second provisional patent application").

This continuation-in-part patent application claims the benefits of prior Provisional Patent Application U.S. Ser. No. 60/572,787, prior Provisional Patent Application U.S. Ser. No. 60/584,655 and prior non-provisional Patent Application U.S. Ser. No. 11/040,953. Each of these three patent applications is hereby incorporated into this continuation-in-part patent application in its entirety by reference.

BACKGROUND OF THE INVENTION

1. Field of the Invention

The present invention is directed to methods and compositions that combine nutritional, health and/or medical benefits provided to mammals by edible oils, particularly by omega-3 fatty acids, with nutritional, health and/or medical benefits provided to mammals by vitamins and/or minerals, particularly by B vitamins.

The present invention relates to compositions for an oral administration to mammals in an oral dosage form, or in a form of a suppository, comprising one or more edible oils, one or more water-soluble vitamins and/or minerals, one or more edible suspending agents that include phytosterols, phytosterol esters, plant stanols or plant stanol esters, or a combination thereof, and, optionally, one or more other components, such as antioxidants, emulsifiers, diluents and/or oil-soluble vitamins and/or minerals. The one or more edible oils preferably include one or more omega-3 fatty acids, and are uniformly combined. The one or more vitamins and/or minerals preferably include one or more water-soluble and oil-insoluble B vitamins, and more preferably include vitamin B6 (pyridoxine), vitamin B9 (folic acid or folate) and/or vitamin B12 (cyanocobalamin, cobalamin, cobalamin bound to recombinant intrinsic factor (rhIF) and/or reduced forms of cobalamin), which may be present in any combination. The one or more vitamins and/or minerals preferably are present in a solid state, and in the form of a uniform mixture, and are uniformly suspended within the one or more edible oils, or are present in an aqueous solution that is a continuous or disperse phase of an emulsion including the one or more edible oils. The one or more edible suspending agents preferably include a combination of CardioAid™-M phytosterols and CardioAid™-S phytosterol esters.

The present invention also relates to methods for producing such compositions, and to methods for using such compositions to provide one or more nutritional, health and/or medical benefits to a mammal, or to enhance one or more of such benefits in a mammal.

Examples of water-soluble vitamins that may be present in the compositions of the invention include the B-vitamins, and more particularly, at least one of vitamin B6, vitamin B9, and vitamin B12, or any combination thereof. The water-soluble vitamins and/or minerals are, optionally, present in a solid-state form such as an amorphous powder or a milled material, for example, a finely milled crystalline material, but can also be present in an aqueous or other solution that is a continuous or disperse phase of an emulsion including the one or more edible oils.

Water-soluble vitamins and/or minerals present in solid form in compositions of the invention preferably become at least temporarily suspended in, and coated with, the one or more edible oils. For example, in one embodiment of the invention, a solid form including a uniform mixture of the water-soluble B vitamins B6, B9 and B12 is coated with, and suspended within, an omega-3 oil. While not wishing to be bound by any theory, it is presently believed that, as a result of the vitamins and/or minerals, or particles thereof, being coated with one or more edible oils, or mixture thereof, compositions within the present invention may have an enhanced ability to transport water-soluble (or other) vitamins and/or minerals through the stomach of a mammal, which generally has a highly acid environment that is maintained by a secretion of hydrochloric acid, without being degraded, or substantially degraded, and, thus, permitting some or all of the water-soluble (or other) vitamins and/or minerals to be delivered to the intestinal tract of the mammal, where they can be absorbed and delivered to other parts of the mammal's body, such as the capillaries, the lymphatic system and the circulatory system, and produce one or more beneficial effects.

Compositions within the invention may be employed to provide, or enhance, nutritional, medical and/or other health benefits to mammals, whether in satisfactory health or having, or suffering from, one or more conditions, illnesses, diseases or disorders, including, but not limited to, depression, dementia, Alzheimer's disease, schizophrenia, rheumatoid arthritis, non-specific arthritis, osteoarthritis, osteoporosis, diabetes, neurological development, neurological degeneration, allergic disorders, immunologic disorders, cancer, pregnancy, lactation and disease states effected, or characterized, by elevated blood pressure, low HDL, arrhythmia, elevated levels of homocysteine, triglycerides and/or c-reactive protein and/or low levels of one or more of the components of the compositions of the invention.

Nutritional and Medical Benefits Provided by Edible Oils and Fatty Acids

Edible fats and oils generally provide nutritional, health and/or medical benefits to mammals. Fats are one of the three main classes of food, and are the most concentrated form of metabolic energy available to humans. Fats and oils are sources of essential fatty acids, an important dietary requirement, as well as other nutritious fatty acids.

Clinical studies have shown that certain edible oils containing DHA (an "omega-3" fatty acid) and other fatty acids can provide significant medical benefits to mammals, particularly to human beings. For example, both omega-3 and omega-6 fatty acids are associated with a lower risk of coronary heart disease. [Frank B. Hu, M. D. et al., "Types of Dietary Fat and Risk of Coronary Heart Disease: A Critical Review," J Am Coll Nutr. 20(1): 5-19 (2001).]

Other publications that discuss the nutritional, health and/or medical benefits provided by edible oils include Elda Hauschildt, "Alpha-Linolenic Acid may help Prevent Heart Disease," Am J Clin Nutr. Vol. 75, 221-227 (2002); Yvonne E. Finnegan et al., "Plant- and Marine-Derived n-3 Polyunsaturated Fatty Acids have Differential Effects on Fasting and Postprandial Blood Lipid Concentrations and on the Susceptibility of LDL to Oxidative Modification in Moderately Hyperlipidemic Subjects," Am J Clin Nutr., Vol. 77, 783-795 (2003); Rozenn N. Lemaitre et al., "n-3 Polyunsaturated Fatty Acids, Fatal Ischemic Heart Disease, and Nonfatal Myocardial Infarction in Older Adults: the Cardiovascular Health Study," Am J Clin Nutr., Vol. 77, 319-325 (2003); Dayong Wu et al., "Effect of Dietary Supplementation with Black Currant Seed Oil on the Immune Response of Healthy Elderly Subjects," Am J Clin Nutr. Vol. 70(4), 536-543 (1999); Frank B. Hu et al., "Dietary Intake of α-Linolenic Acid and Risk of Fatal Ischemic Heart Disease Among Women," Am J Clin Nutr. Vol. 69, 890-897 (1999); and EH Temme et al., "Comparison of the Effects of Diets Enriched in Lauric, Palmitic, or Oleic Acids on Serum Lipids and Lipoproteins in Healthy Women and Men," Am J Clin Nutr., Vol 63, 897-903 (1996).

Fatty acids, such as "omega-3" fatty acids (also known as "n-3" fatty acids), "omega-6" fatty acids, "omega-9" fatty acids and essential fatty acids are generally present in high levels in various edible oils. "Omega-3 fatty acids" are the n-3 family of polyunsaturated fatty acids, and are called "n-3 fatty acids" because the first double bond occurs in the third carbon bond counting from the end or omega position of the fatty acid. Omega-3 fatty acids have many nutritional, health and/or medical benefits associated with them, and thus, can provide numerous beneficial effects to human beings and a wide variety of animals that ingest them, whether the consumers are healthy or have one or more conditions, illnesses, diseases or disorders. Although omega-3 fatty acids can be obtained from other sources, such as plant oils, fish have a unique ability to provide high levels of various specific fatty acids, such as the omega-3 fatty acids docosahexaenoic acid (DHA) and eicosapentaenoic acid (EPA). Omega-3 fatty acids include, for example, docosahexaenoic acid (DHA), docosapentaenoic acid, alpha-linolenic acid (ALA), eicosapentaenoic acid (EPA), eicosatetraenoic acid, moroctic acid and heneicosapentenoic acid. Omega-3 fatty acids are precursors of eicosanoids (prostaglandins, thromboxanes and leukotrienes), which are signal substances (cell messengers) that can have a widely different effect upon biological activity. Many of these signal substances regulate physiological and immunological reactions.

Omega-3 fatty acids have been shown to be beneficial in the prevention of cardiovascular pathology, the reversal of atherosclerosis, the inhibition of tumor formation and the development and regulation of serum cholesterol. Prospective cohort studies and secondary prevention trials have provided strong evidence that an increased intake of n-fatty acids from fish or plant sources substantially lowers a risk of cardiovascular mortality. [Frank B. Hu, M. D. et al., "Types of Dietary Fat and Risk of Coronary Heart Disease: A Critical Review," supra.] Other research suggests the therapeutic value of oils rich in omega-3 unsaturated fatty acids for disorders related to blood hyperviscosity, including the lowering of serum cholesterol and the suppression or reduction of plasma triglycerides, inflammatory autoimmune disorders, tumors and various other disorders. [D. F. Horrobin, "Clinical uses of Essential Fatty Acids," Eden. Press, London, 1982.] The omega-3 fatty acids also suppress the production of the proinflammatory cytokines tumor necrosis factor (TNF), particularly TNF alpha, interleukin-1 (IL-1) and thromboxanes. The protective effects of n-3 fatty acids are likely a result of multiple mechanisms, including reducing triglyceride levels, reducing platelet aggregation and antiarrhythmic effects.

Omega-3 fatty acids are also essential for the normal development of an unborn baby's brain, especially during the third trimester, when the size of a baby's brain increases threefold. If a baby's mother fails to have a sufficient quantity of omega-3 fatty acids in her diet, the fetus will generally depend upon the mother's brain tissue and tissue storage of these omega-3 fatty acids. Lab tests have shown that new mothers have approximately one half of the normal blood levels of omega-3 fatty acids.

Linolenic acid, a polyunsaturated fatty acid having three double bonds, is a precursor to EPA and DHA, and is considered to be a dietary essential fatty acid. Because the body is not capable of synthesizing linolenic acid, it must be acquired from a dietary source, such as food or supplements.

DHA is an omega-3 long-chain fatty acid that is the primary structural fatty acid in the gray matter of the brain, and in the retina of the eye, and accumulates during the fetal period and the first year after birth. DHA is essential for normal visual and neurological (nervous system) development in infants, and for normal brain and eye function in adults. It is necessary for brain and eye development, growth and learning ability in children. [A. P. Simopoulos, "Omega-3 Fatty Acids in Health and Disease and in Growth and Development," American Journal of Clinical Nutrition 54, No. 3, 438-463 (1991).]

The human body only synthesizes small quantities of DHA. As a result, it is generally necessary to obtain DHA from dietary sources. The primary source of DHA is fatty fish, such as mackerel, salmon, herring, sardines, black cod, anchovies and albacore tuna, and oils from the tissues of such fish.

DHA and EPA, which is associated with vascular regeneration, can alter eicosanoid and cytokine production, providing an improved immunocompetence (strengthening immune system activity) and a reduced inflammatory response to injury. The contributions of DHA and EPA in reducing the incidence of numerous inflammatory/circulatory disorders, cardiac problems and premature births, and in enhancing cognitive ability in children and mental well being, has been well documented.

ALA is an essential omega-3 fatty acid for humans. Adequate intake of ALA and long-chain omega-3 fatty acids is especially important for infants, young children and patients requiring parenteral and enteral nutrition. Experimental studies have suggested an antiarrhythmic effect of ALA, and beneficial effects of ALA on cardiovascular disease. [Frank B. Hu, M. D. et al., "Types of Dietary Fat and Risk of Coronary Heart Disease: A Critical Review," supra.]

"Omega-6" fatty acids include gamma-linolenic acid (GLA), which is present in Black Current Seed Oil, linoleic acid, which is present in many vegetable oils, and arachidonic acid, which is present in many animal fats and in algae oil. GLA is an n 18:3 omega-6 polyunsaturated fatty acid that has been used in the amelioration of various diseases, such as eczema, rheumatoid arthritis and premenstrual syndrome, and that has been shown to improve the effectiveness of cancer chemotherapy. Arachidonic acid (ARA or AA) is an omega-6 polyunsaturated fatty acid that has been shown to play a role in early neurological and visual development, and is a precursor in the biosynthesis of some prostaglandins.

"Omega-9" fatty acids include, for example, oleic acid, which is present in sunflower oil, olive oil, avocados, canola oil and in many animal fats.

Marine oils (including "fish oils") are oils that are obtained from aquatic lifeforms, either directly or indirectly, particularly from oily fish. Marine oils include, for example, herring oil, cod oil, anchovy oil, tuna oil, sardine oil, menhaden oil and algae oil. Fish that are employed to produce marine oils include, for example, farm-raised or wild, fresh-water or salt-water, fish and shellfish, such as herring, salmon, salmonoids, gadoids, shrimp, cod, carp, tilapia, perch, trout, sturgeon, krill, tuna, flat fish, anchovies, sardines, menhaden, shrimp, Mackerel, eels and seals. Marine oils may also be obtained from marine organisms, such as calanus (*Calanus finmarchi-*

*cus*), a 3-4 mm copepod, algae and microalgae, for example, diatoms and dinoflagellates. Peru is currently the world's largest producer of fish oil.

Although omega-3 fatty acids can be obtained from other sources, such as plant oils, fish have a unique ability to provide high levels of the omega-3 fatty acids DHA and EPA. Fish and fish oils are also sources of the "omega-3" fatty acids docosapentaenoic acid, eicosatetraenoic acid, moroctic acid and heneicosapentenoic acid. Marine oils having a total "omega-3" fatty acid content of greater than about 20 weight percent include those derived from menhaden oil, herring, capelin, anchovy, cod liver, salmon oil, sardine oil and mixtures thereof. Oils containing omega-3 fatty acids, such as marine oils and DHA, are also referred to as "omega-3" oils or "n-3" oils.

A low rate of cardiovascular disease in populations that have a high intake of fish, such as Alaskan Native Americans, Greenland Eskimos and Japanese living in fishing villages, suggests that fish oil may be protective against artherosclerosis. [Frank B. Hu, M. D. et al., "Types of Dietary Fat and Risk of Coronary Heart Disease: A Critical Review," supra.] Additionally, research into the blood chemistry of Eskimos, who consume large quantities of fish, showed low levels of low-density lipoproteins (LDL cholesterol) and high levels of high-density cholesterol (HDL cholesterol) in the blood despite a rich diet of fatty fish and seals. [Dyerberg et al., "Fatty Acid Composition of Plasma Lipids in Greenland Eskimos," American Journal of Clinical Nutrition 28, 958-966 (1975).]

It is known that an oral administration of fish oil, which contains omega-3 fatty acids, has beneficial effects on cardiovascular and/or brain function, and has other health benefits. One article reports "a significant, graded, independent inverse association between base-line fish consumption and the 30-year risk of fatal myocardial infarction, particularly non-sudden death from myocardial infarction [that] accounted for the [observation of] lower rates of death from all coronary causes, all cardiovascular causes, and all causes in association with higher fish consumption . . . " [Daviglus, M. L., et al., N Engl J Med 1997; 336(15): 1046-53.]

Another study found that, "dietary intake of omega-3 fatty acids, approximately 1.5 g/l for 2 years, modestly mitigated the course of human coronary atherosclerosis, as assessed by angiography. Fewer cardiovascular events were noted." [Von Schacky, C., et al, Ann Intern Med. 1999; 130:554-62.] Yet, another study found that omega-3 fatty acids found in fish oil reduced the risk of sudden death in men without evidence of prior cardiovascular disease. [Albert, C. M., et al., N Engl J Med 2002; 346(15): 1113-18.]

There is growing evidence to suggest that fish oil may improve endothelial dysfunction, an early marker of atherosclerosis. In vitro studies have consistently shown that n-3 fatty acids decrease expression of adhesion molecules on the endothelium, and also decrease leukocyte/endothelium interactions. Further, clinical experimental studies have shown that n-3 fatty acid supplementation improves endothelial-dependent vasomotor function. [Frank B. Hu, M. D. et al., "Types of Dietary Fat and Risk of Coronary Heart Disease: A Critical Review," supra.]

Various modified or unmodified fungi, such as filamentous fungi, also have an ability to produce lipids having high levels of fatty acids, such as GLA. Modified fungi have been employed to ferment DHA oil. Fungi can be isolated from soil and subsequently fermented using known techniques and conventional shake flasks or fermentation systems.

Many plant oils (including vegetable oils and plant seed oils), such as Evening Primrose oil, Black Currant seed oil, Borage oil, Borage seed oil, safflower oil, sunflower oil, peanut oil, olive oil, corn oil, soybean oil, coconut oil, palm oil, palm kernel oil, rapeseed oil, flaxseed (linseed) oil and cotton seed oil, contain high levels of fatty acids, such as GLA, as well as other fatty acids. For example, flaxseed oil, rapeseed oil and soybean oil contain a large quantity of ALA (about 20% in flaxseed oil and about 7% in unhydrogenated soybean oil). GLA is present in Evening Primrose oil, Black Currant seed oil and Borage seed oil, with the highest level of GLA being present in Borage seed oil. Safflower oil and sunflower oil are rich in linoleic acid. Olive oil contains a significant amount of oleic acid.

Numerous metabolic studies have shown strong cholesterol-lowering effects for vegetable oils that are rich in linoleic oil when substituted for dietary saturated fat. In addition, animal studies have suggested an anti-arrhythmic effect when sunflower oil (rich in linoleic acid) was consumed. [Frank B. Hu, M. D. et al., "Types of Dietary Fat and Risk of Coronary Heart Disease: A Critical Review," supra.]

Plant oils can be extracted from plants or seeds using techniques that are known by those of skill in the art. For example, the highest quality Borage seed oil is generally extracted without hexane or the use of other chemical solvents. Rather, the Borage seed oil is "cold processed" using an expeller-press method of extraction, which simply squeezes the oil out from the seed without the use of heat.

With respect to neurological function, Morris, M. C., et al., Arch Neurol 2003: 60: 940-6, have shown that the omega-3 polyunsaturated fatty acids have "profound effects on membrane functions, leading to change in nerve conduction, neurotransmitter release, neurotransmitter reuptake, and postsynaptic transmitter effects. A large number of animal studies have demonstrated that dietary n-3 fatty acids increased learning acquisition and memory performance . . . " See also, Horrocks, L. A. and Young, K. Y., Pharmacological Research 1999; 40(3): 211-25. ("Low levels of DHA are also associated with senile dementia (Alzheimer's disease) and schizophrenia," and "Chronic alcohol intoxication depletes DHA from membranes of the neurons, leading to the common secondary depression in alcoholism.")

Zanarini, M. C. and Frankenburg, F. R, Am J Psychiatry 2003; 160: 167-9, report results from a double-blind, placebo-controlled study that are "consistent with the findings of recent reports concerning omega-3-fatty acids as an effective adjunctive treatment for bipolar disorder and recurrent depression."

Thus, there is substantial evidence that omega-3 fatty acids can beneficially affect a variety of diseases. See e.g., Conner, W. E., Am J Clin Nutr 2000; 71 (suppl): 171S-5S (omega-3 fatty acids "favorably affect atherosclerosis, coronary heart disease, inflammatory disease, and perhaps even behavioral disorders.").

Nutritional and Medicinal Benefits Provided by B-Vitamins and Other Water-Soluble Vitamins and Minerals High levels of homocysteine (an amino acid) have been reported to be associated with cardiovascular diseases. Refsum, H. and Ueland, P. M., Annu Rev Medicine 1998; 49:31-62 report that "[a]n elevated level of total homocysteine (tHcy) in blood, denoted hyperhomocysteinemia, is emerging as a prevalent and strong risk factor for atherosclerotic vascular disease in the coronary, cerebral, and peripheral vessels, and for arterial and venous thromboembolism." Similarly, Schnyder, G., et al., N Engl J Med 2001: 345(22): 1593-1600, report that the level of plasma homocysteine can be reduced significantly with a daily dose of folic acid in an amount of at least 500 micrograms, in combination with vitamin B6 (pyridoxine) and vitamin B 12 (cyanocobalamin, cobalamin, and/ or reduced forms of cobalamin). "Roughly one half of US adults on a given day consume less than the newly lowered recommended dietary allowance for folate, and an estimated 88% consume less than the levels needed to produce low, stable homocysteine levels." Morrison, H. I., et al. Serum Folate and Risk of Fatal Coronary Heart Disease JAMA 1996; 275(24): 1893-6.

Vitamin B9 (folic acid/folate) is thought to be crucial for proper brain function, and plays an important role in mental and emotional health. It aids in the production of DNA and RNA, the body's genetic material, and is especially important during periods of high growth, such as infancy, adolescence and pregnancy. Folic acid also works closely together with vitamin B12 to regulate the formation of red blood cells, and to help iron function properly in the body.

Vitamin B9 works closely with vitamins B6 and B12, as well as with the nutrients betaine and S-adenosylmethionine (SAM), to control blood levels of the amino acid homocysteine. Elevated levels of this substance appear to be linked to certain chronic conditions, such as heart disease and, possibly, depression and Alzheimer's disease. Some researchers have even speculated that there is a connection between high levels of this amino acid and cervical cancer, but the results of studies regarding this issue have been inconclusive.

Vitamin B 12 (cyanocobalamin, cobalamin, cobalamin bound to recombinant intrinsic factor (rhIF) and/or reduced forms of cobalamin) functions as a methyl donor and works with folic acid in the synthesis of DNA and red blood cells and is vitally important in maintaining the health of the insulation sheath (myelin sheath) that surrounds nerve cells. The classical vitamin B12 deficiency disease is pernicious anemia, a serious disease characterized by large, immature red blood cells. It is now clear, though, that a vitamin B12 deficiency can have serious consequences long before anemia is evident. Many elderly people are also deficient because their production of the intrinsic factor needed to absorb the vitamin from the small intestine declines rapidly with age.

Vitamin B12 plays an important role in maintaining a low blood concentration of homocysteine by participating in reactions that recycle homocysteine into methionine. In cases of a deficiency of vitamin B12, the conversion of homocysteine to methionine is inhibited. The resulting raised level of homocysteine has been estimated to be a greater risk factor and predicator for cardiovascular diseases than an increased level of cholesterol, high blood pressure, cigarette smoking, and elevated lipoproteins and hypertension. A B12 deficiency has also been suggested to be an independent risk factor for neural tube birth defects. Neural tube defects (NTDs) are a failure of closure of the neural tube, which includes the spinal cord and the brain, and is among the most devastating of all birth defects. A deficiency of vitamin B12 is thought to result in a lack of methionine, which is the sole precursor to the "universal methylator" (S-adenosylmethionine). S-adenosylmethionine participates in almost all methylation processes in the human body. A lack of S-adenosylmethionine slows the growth and/or closure of the neural tube and, thereby, increases the risk of NTDs. Lower plasma levels of vitamin B12 have also been associated with breast cancer. Vitamin B12, along with folate and vitamin B6, functions as a coenzyme in the building of components for DNA synthesis. Inadequate levels of vitamin B12 may cause misincorporation of uracil, normally found in RNA, into DNA, which may result in chromosome breaks and disruption of DNA repair. Additionally, a deficiency of vitamin B12 may cause aberrant DNA methylation, which has been observed in human tumors. Vitamin B12 deficiency is particularly associated with cognitive impairment and widespread pathology in the central nervous system in the elderly. In cells, vitamin B12 is converted to coenzymes, which influence brain function through the one carbon metabolism/methylation cycle. Vitamin B12 is required for the synthesis of methionine and S-adenosylmethionine, which the brain relies on to metabolize homocysteine. Furthermore, S-adenosylmethionine dependant reactions include the formation of neurotransmitters, phospholipids and myelin. Thus, vitamin B12 deficiency may cause nervous system dysfunction in the elderly. A severe and progressive consequence of a deficiency of vitamin B12 is the degeneration of the spinal cord. Classical symptoms include symmetrical parasthesias in the hands and feet leading to numbness, muscle weakness and paralysis.

Need for a Dosage Form Incorporating Both Fatty Acids and B-Vitamins

In view of the significant nutritional, medical and/or other health benefits provided by many edible oils, such as the omega-3 fatty acids DHA, EPA AND ALA, AND BY WATER-SOLUBLE vitamins and/or minerals, such as B-vitamins, it would be beneficial to provide oral dosage forms for an oral administration to mammals, or suppository dosage forms, that include one or more edible oils and one or more water-soluble vitamins and/or minerals, such as B-vitamins, that properly disintegrate, thereby allowing the edible oils and water-soluble vitamins and/or minerals to become bioavailable, that may permit the edible oils and water-soluble vitamins and/or minerals to be absorbed by the body without being substantially or fully degraded in the acidic environment of the stomach, and that may have a long shelf life under room temperature conditions.

Compositions within the present invention provide oral dosage forms for an oral administration to mammals, and suppository dosage forms, that preferably include one or more edible oils, one or more water-soluble vitamins and/or minerals, such as B-vitamins, one or more suspending agents and, optionally, one or more other components, such as antioxidants, emulsifiers or diluents, that properly disintegrate, thereby allowing the edible oils and water-soluble vitamins and/or minerals to become bioavailable, that may permit the edible oils and water-soluble vitamins and/or minerals to be absorbed by the body without being substantially or fully degraded in the acidic environment of the stomach, and that may have a long shelf life under room temperature conditions.

In view of the foregoing benefits, compositions within the present invention may be effective for improving cardiovascular function, lowering the incidence of myocardial infarction, improving cardiac arrhythmia problems and/or lowering elevated homocysteine levels which, in turn, may have a benefit of lowering the incidence of heart disease and/or depression.

2. Description of the Related Art

The Physicians' Desk Reference (49$^{th}$ Edition, 1995, and 54$^{th}$ Edition, 2000) describes a prenatal vitamin and mineral tablet marketed by Lederle Laboratories (Wayne, N.J.) under the trademark name Materna® (pages 1264 and 1534, respectively).

U.S. Pat. No. 5,494,678 discloses multi-vitamin and mineral supplements for incorporation into tablets, powders, granules, beads, lozenges, capsules and liquids, and administration to a pregnant woman during her first, second and third trimesters of pregnancy. The supplements contain specific regimens of a calcium compound, vitamin D, folic acid, vitamin B12, vitamin B6, and vitamin B1.

U.S. Pat. No. 5,571,441 discloses nutritional supplement compositions containing vitamins, minerals, central nervous system bracers, such as caffeine, and flavenols, that are coadministered in the form of a tablet or capsule, as a powder, or as a liquid form.

U.S. Pat. No. 5,869,084 discloses multi-vitamin and mineral supplements for administration to lactating, non-lactating (but not pregnant) and menopausal women in the form of tablets, powders, granules, beads, lozenges, capsules or liquids.

U.S. Pat. No. 5,906,833 discloses nutritional supplements that contain vitamins.

SUMMARY OF THE INVENTION

The present invention provides compositions in an oral dosage form for an oral administration to a mammal, or in a form of a suppository, that include one or more edible oils and one or more water-soluble vitamins and/or minerals and, optionally, one or more other suitable components, wherein the compositions generally properly disintegrate, thereby allowing the edible oils and/or water-soluble vitamins and/or minerals present therein to become bioavailable, wherein the water-soluble vitamins and/or minerals are permitted to be absorbed by the body of the mammal without being substantially or fully degraded in the acidic environment of the stomach, and wherein the compositions have a long shelf life under room temperature conditions.

Each of the components that may be present in the compositions of the present invention, or that may be employed in the methods of the invention, may be exogenous to all of the other components that are present in the compositions (derived, or obtained, from an external source) or, in some cases, and if possible, may be endogenous to one or more of the other components that are present in the compositions (originating in, or produced by, one or more of the other components of the compositions). For example, if one or more edible oils that are employed in the methods or compositions of the invention is, contains, or functions as a suspending agent, the suspending agent will be endogenous to the one or more edible oils. However, one or more suspending agents that is derived, or obtained, from an external source (a source other than the one or more edible oils and the other components that are present in the compositions) may be employed in the methods and compositions of the invention.

In one aspect, the present invention provides a composition in an oral dosage form for an oral administration to a mammal, or in a form of a suppository, comprising:
  (a) one or more vitamins or minerals, or a combination thereof, in a combined amount that is effective for providing or enhancing one or more nutritional, medical or other health benefits, or a combination thereof, to a mammal, wherein the one or more vitamins or minerals, or combination thereof, are water-soluble and oil-insoluble, are initially in a solid-state form, are exogenous to one or more edible oils that may be included in the composition and are in a form that is capable of being mixed with one or more edible oils;
  (b) one or more edible oils, or a combination thereof, in a combined amount that is effective for permitting the one or more vitamins or minerals, or combination thereof, to be mixed with the one or more edible oils, or combination thereof, wherein the one or more edible oils, or combination thereof, includes one or more substances that can provide a nutritional, medical or other health benefit, or a combination thereof, to a mammal;
  (c) one or more edible suspending agents, or a combination thereof, in a combined amount that is effective for initiating, enhancing or maintaining a suspension of the one or more vitamins or minerals, or combination thereof, in the one or more edible oils, or combination thereof, and/or for providing a nutritional, medical or other health benefit, or a combination thereof, to a mammal, wherein the one or more edible suspending agents, or a combination thereof, include phytosterols, phytosterol esters, plant stanols or plant stanol esters, or a combination thereof;
  (d) optionally, one or more edible antioxidant agents, or a combination thereof, in a combined amount that is effective for preventing or reducing an oxidation, degradation or other decomposition of the one or more vitamins or minerals, or combination thereof, the one or more edible oils, or combination thereof, or one or more other components that are included in the composition, or any combination thereof;
  (e) optionally, one or more edible diluents, or a combination thereof, in a combined amount that is effective for diluting, rendering less potent, thinning, weakening or facilitating a physical separation of one or more components that are included in the composition;
  (f) optionally, one or more edible emulsifiers, or a combination thereof, in a combined amount that is effective for causing or enhancing a formation of an emulsion;
  (g) optionally, one or more edible surfactants, or a combination thereof, in a combined amount that is effective for reducing a surface tension when dissolved or otherwise included in an aqueous liquid or reducing an interfacial tension between two liquids, or between a liquid and a solid; and
  (h) one or more edible hollow oral dosage forms or hollow suppository forms;
wherein the one or more vitamins or minerals, or combination thereof, are admixed with the one or more edible oils, or combination thereof, and/or the one or more edible suspending agents, or combination thereof; and
wherein the one or more vitamins or minerals, or combination thereof, the one or more edible oils, or combination thereof, and the one or more edible suspending agents, or combination thereof, are present in the composition in a form of:
  (i) a suspension, wherein the one or more vitamins or minerals, or combination thereof, are at least temporarily suspended in the one or more edible oils, or combination thereof; or
  (ii) a dispersion, wherein the one or more vitamins or minerals, or combination thereof, are included in an aqueous liquid;
wherein the suspension or dispersion is inserted into the one or more edible hollow oral dosage forms or hollow suppository forms, or is formed into a solid suppository, to provide one or more unit dosage forms of the composition; and
wherein a substantially uniform quantity of the one or more vitamins or minerals, or combination thereof, and the one or more edible oils, or combination thereof, is present in the one or more unit dosage forms.

In another aspect, the present invention provides a composition in an oral dosage form for an oral administration to a mammal, or in a form of a suppository, comprising:
  (a) one or more water-soluble vitamins or minerals, or a combination thereof, in a combined amount that is effective for providing and/or enhancing one or more nutritional, medical and/or other health benefits to a mammal, wherein the one or more water-soluble vitamins or minerals, or combination thereof, are in a form that is capable of being mixed with one or more edible oils, or a combination thereof, such as a powder;

(b) one or more edible oils, or a combination thereof, in a combined amount that is effective for permitting the one or more water-soluble vitamins or minerals, or combination thereof, to be mixed with the one or more edible oils, or combination thereof;

(c) one or more anhydrous diluents, or a combination thereof, in a combined amount that is effective for diluting, rendering less potent, thinning, weakening and/or facilitating a physical separation of the one or more water-soluble vitamins or minerals, or combination thereof ("the powder phase"); and (d) optionally, one or more antioxidant agents, or a combination thereof, in a combined amount that is effective for preventing or reducing an oxidation, degradation or other decomposition of the one or more water-soluble vitamins or minerals, or combination thereof and/or the one or more edible oils, or combination thereof.

In another aspect, the present invention provides a composition in an oral dosage form for an oral administration to a mammal, or in a form of a suppository, comprising:

(a) one or more solid-state particles of one or more water-soluble vitamins or minerals, or a combination thereof, in a combined amount that is effective for providing or enhancing a nutritional, medical and/or other health benefit to the mammal; and (b) one or more edible oils, or a combination thereof, that include one or more fatty acids, or a combination thereof, wherein the one or more fatty acids are omega-3 fatty acids, omega-6 fatty acids and/or omega-9 fatty acids, and wherein the one or more edible oils and/or the one or more fatty acids is present in a combined amount that is effective for permitting the one or more solid-state particles to be at least temporarily suspended in the one or more edible oils and/or the one or more fatty acids;

wherein the one or more solid-state particles are admixed with, or at least temporarily suspended in, the one or more edible oils and/or the one or more fatty acids.

In another aspect, the present invention provides a composition in an oral dosage form for an oral administration to a mammal, or in a form of a suppository, comprising:

(a) one or more solid-state particles of one or more water-soluble vitamins wherein the one or more water-soluble vitamins are vitamin B6, vitamin B9 or vitamin B12, or a combination thereof, and wherein the one or more water-soluble vitamins, or combination thereof, are in a combined amount that is effective for providing or enhancing a nutritional, medical and/or other health benefit to the mammal; and (b) one or more edible oils, or a combination thereof, including one or more omega-3 fatty acids, or a combination thereof, in a combined amount that is effective for providing or enhancing a nutritional, medical and/or other health benefit to the mammal;

wherein the one or more solid-state particles are mixed with the one or more edible oils, or combination thereof, or are at least temporarily suspended therein.

In another aspect, the present invention provides a composition in an oral dosage form for an oral administration to a mammal, or in a form of a suppository, comprising:

(a) one or more water-soluble vitamins or minerals, or a combination thereof, in a combined amount that is effective for providing or enhancing a nutritional, medical and/or other health benefit to the mammal, wherein the one or more water-soluble vitamins or minerals, or combination thereof, are combined with an amount of water that is sufficient to form an aqueous solution;

(b) one or more edible emulsifiers, or a combination thereof, in a combined amount that is effective to cause or enhance a formation of an emulsion; and (c) one or more edible oils, or a combination thereof, in a combined amount that is effective for forming an oil phase of an emulsion;

wherein the aqueous solution is combined with the one or more emulsifiers, or combination thereof, and the one or more edible oils, or combination thereof, in a manner that forms an emulsion, preferably a water-in-oil (w/o) emulsion or an oil-in-water (o/w) emulsion.

After compositions within the invention in a form for an oral administration to a mammal are consumed by a mammal, at least some of the water-soluble or other vitamins and/or minerals present therein, or particles thereof, generally have an enhanced ability to travel through an acidic environment of a stomach of the mammal without being substantially or fully degraded and into an intestinal tract of the mammal, and to be absorbed into the mammal's body, in comparison with other compositions for oral administration that contain the same water-soluble or other vitamins and/or minerals.

Compositions within the present invention also generally have an enhanced stability and/or shelf life in comparison with other compositions for an oral administration to a mammal, or in a form of a suppository, that contain the same water-soluble or other vitamins and/or minerals.

In another aspect, the present invention provides a method for producing a composition in an oral dosage form for an oral administration to a mammal, or in a form of a suppository, comprising:

(a) providing one or more vitamins or minerals, or a combination thereof, in a combined amount that is effective for providing or enhancing one or more nutritional, medical or other health benefits, or a combination thereof, to a mammal, wherein the one or more vitamins or minerals, or combination thereof, are water-soluble and oil-insoluble, are initially in a solid-state form, are exogenous to one or more edible oils that may be included in the composition and are in a form that is capable of being mixed with one or more edible oils;

(b) providing one or more edible oils, or a combination thereof, in a combined amount that is effective for permitting at least some of the one or more vitamins or minerals, or combination thereof, to be mixed therewith, or at least temporarily suspended therein, or for forming a continuous or disperse phase of a dispersion, wherein the one or more edible oils, or combination thereof, includes one or more substances that can provide a nutritional, medical or other health benefit, or a combination thereof, to a mammal;

(c) providing one or more edible suspending agents, or a combination thereof, in a combined amount that is effective for initiating, enhancing or maintaining a suspension of the one or more vitamins or minerals, or combination thereof, in the one or more edible oils, or combination thereof, and/or for providing a nutritional, medical or other health benefit, or a combination thereof, to a mammal, wherein the one or more edible suspending agents, or a combination thereof, include phytosterols, phytosterol esters, plant stanols or plant stanol esters, or a combination thereof;

(d) optionally, providing one or more edible antioxidant agents, or a combination thereof, in a combined amount that is effective for preventing or reducing an oxidation, degradation or other decomposition of the one or more vitamins or minerals, or combination thereof, the one or more edible oils, or combination thereof, or of one or more other components that are present in the composition, or any combination thereof;

(e) optionally, providing one or more edible diluents, or a combination thereof, in a combined amount that is effective for diluting, rendering less potent, thinning, weakening or facilitating a physical separation of one or more components that are included in the composition;

(f) optionally, providing one or more edible emulsifiers, or a combination thereof, in a combined amount that is effective for causing or enhancing a formation of an emulsion;

(g) optionally, providing one or more edible surfactants, or a combination thereof, in a combined amount that is effective for reducing a surface tension when dissolved or otherwise included in an aqueous liquid or reducing an interfacial tension between two liquids, or between a liquid and a solid;

(h) providing one or more edible hollow oral dosage forms or hollow suppository forms;

(i) optionally, mixing the one or more vitamins or minerals, or combination thereof, for a period of time and under conditions that are effective for producing a substantially uniform mixture of the one or more vitamins or minerals, or combination thereof;

(j) optionally, mixing the one or more vitamins or minerals, or combination thereof, with an amount of an aqueous liquid, and for a period of time and under conditions, that are effective for forming an aqueous solution;

(k) optionally, mixing the one or more edible oils, or combination thereof, for a period of time and under conditions that are effective for producing a uniform mixture of the one or more edible oils, or combination thereof;

(l) optionally, mixing the one or more edible suspending agents, or combination thereof, for a period of time and under conditions that are effective for producing a uniform mixture of the one or more edible suspending agents;

(m) optionally, combining the antioxidant agents, diluents, emulsifiers, surfactants or other optional ingredients, or combination thereof, with the one or more vitamins or minerals or the one or more edible oils, or with any combination thereof;

(n) combining the one or more vitamins or minerals, or combination thereof, with the one or more edible oils, or combination thereof, or the one or more edible suspending agents, or combination thereof, or both, for a period of time and under conditions that are effective for:

(i) producing a suspension of at least some of the one or more vitamins or minerals, or particles or combination thereof, in the one or more edible oils, or combination thereof, wherein the one or more vitamins or minerals, or particles or combination thereof, and the one or more edible oils, or combination thereof, remain in suspension for at least a period of time that is sufficient to enable the one or more edible hollow dosage forms or hollow suppository forms to be partially or fully filled with the suspension; or (ii) producing a dispersion; and (o) inserting the suspension or dispersion into the one or more edible hollow oral dosage forms or hollow suppository forms, or forming a solid suppository therewith, in an amount that is effective for partially or fully filling the one or more edible hollow oral dosage forms or hollow suppository forms, or forming a solid suppository, so as to form one or more unit dosage forms, wherein substantially the same quantity of each of the components that are present in the composition becomes present in each of the one or more unit dosage forms.

In another aspect, the present invention provides a method for preparing a composition in an oral dosage form for an oral administration to a mammal, or in a form of a suppository, comprising:

(a) providing one or more solid state particles of one or more water-soluble vitamins and/or minerals, or combination thereof;

(b) providing one or more edible oils, or a combination thereof, wherein the one or more edible oils includes one or more fatty acids, or a combination thereof, and wherein the one or more edible oils, or combination thereof, is in a combined amount that is effective for permitting at least some, and preferably all, of the one or more water-soluble vitamins or minerals, or particles or combination thereof, to be at least temporarily suspended therein;

(c) optionally, mixing the one or more water-soluble vitamins or minerals, or combination thereof, for a period of time and under conditions that are sufficient to produce a uniform mixture of the one or more water-soluble vitamins or minerals, or combination thereof;

(d) optionally, mixing the one or more edible oils, or combination thereof, for a period of time and under conditions that are sufficient to produce a uniform mixture of the one or more edible oils;

(e) suspending, at least temporarily, an amount of the one or more water-soluble vitamins or minerals, or combination thereof, within an amount of the one or more edible oils, or combination thereof, that is effective for producing a suspension of at least some, and preferably all, of the solid-state particles of the one or more water-soluble vitamins or minerals, or combination thereof, within the one or more edible oils, or mixtures thereof; and (f) injecting or otherwise inserting a suspension resulting from step (e) into one or more edible hollow oral dosage forms or hollow suppository forms, or forming a solid suppository therewith, wherein the edible hollow oral dosage forms or hollow suppository forms are hard or soft capsules, gelatin capsules, caplets or gelatin caplets.

In another aspect, the present invention provides a method for preparing a composition in an oral dosage form for an oral administration to a mammal, or in a form of a suspension, comprising:

(a) providing one or more solid-state particles of one or more water-soluble vitamins or minerals, or combination thereof;

(b) mixing the solid-state particles in an amount of water that is sufficient to form an aqueous solution;

(c) providing one or more edible emulsifiers, or a combination thereof;

(d) providing one or more edible oils, or combination thereof, wherein the one or more edible oils, or combination thereof, include one or more fatty acids;

(e) optionally, mixing the one or more edible oils, or combination thereof, for a period of time and under conditions that are sufficient to produce a uniform mixture of the one or more edible oils, or combination thereof;

(f) mixing the aqueous solution with the one or more edible emulsifiers, or combination thereof, and the one or more edible oils, or combination thereof, under conditions that are sufficient to form an emulsion; and (g) injecting the emulsion into one or more hollow oral dosage forms or hollow suppository forms that are soft or hard capsules, gelatin capsules, caplets or gelatin caplets.

In yet another aspect, the present invention provides a method for enhancing the quantity of one or more water-soluble vitamins and/or minerals that are absorbed by an intestinal tract of a mammal and delivered to the mammal's body after the mammal consumes one or more water-soluble or other vitamins and/or minerals and/or edible oils comprising orally administering to the mammal a composition of the present invention in an oral form and in an amount that is effective for enhancing the quantity of one or more water-soluble or other vitamins and/or minerals that are absorbed by the intestinal tract of the mammal and delivered to the mammal's body after the mammal consumes the composition.

In still another aspect, the present invention provides a method for enhancing the nutrition, health and/or medical condition of a mammal comprising administering to the mammal, either orally or in a form of a suppository, a composition of the present invention in an amount that is effective for enhancing the nutrition, health and/or medical condition of the mammal.

The water-soluble or other vitamins and/or minerals that may be present in the compositions of the invention may be present alone or in any desired combination of two or more water-soluble or other vitamins and/or minerals. For example, the compositions may include the vitamins B6, B9 and B12, or other B vitamins, alone or in any desired combination, and in any desired quantity that is safe for consumption by a particular mammal, which may readily be determined by those of skill in the art. The water-soluble or other vitamins and/or minerals employed in the compositions of the invention are, optionally, in solid-state forms and subsequently partially or fully suspended, at least temporarily, in one or more edible oils, or a combination thereof, to produce a suspension in which the solid-state vitamins and/or minerals are preferably coated with the one or more edible oils, or a combination thereof. The water-soluble or other vitamins and/or minerals can also be present in the compositions in the form of an aqueous solution, preferably in combination with one or more emulsifiers, wherein an emulsion (oil-in-water emulsion, water-in-oil emulsion or the like) is formed with the one or more edible oils. The compositions of the present invention are suitable for an oral administration to a mammal, or in a form of a suppository, and are typically, and preferably, provided as gelatin capsules, such as soft-gel or hard-gel capsules, but may be provided in any other suitable oral dosage form, or suppository form, such as those that are known by those of skill in the art.

Edible oil suspensions of solid-state B and/or other vitamins and/or minerals can be prepared by mixing powdered (e.g., micronized or milled) vitamins and/or minerals so as preferably to form a substantially uniform mixture, and subsequently suspending such mixture in one or more edible oils, or a mixture thereof, to produce a suspension that is preferably homogeneous, and is preferably capable of remaining as a homogenous suspension at least for a period of time that is required to perform a filling step of a process for preparing gel capsules (or other oral dosage forms or suppository forms) with the suspension (i.e. filling the gel capsules with the suspension), so as to maximize content uniformity in the various filled gel capsules (or other oral dosage forms or suppository forms).

The stability of water-soluble or other vitamins and/or minerals present in compositions within the present invention may generally be enhanced in comparison with other oral dosage or suppository forms containing the same or similar water-soluble or other vitamins and/or minerals, for example, those that are prepared in a different manner (i.e. those that do not have one or more solid-state water-soluble or other vitamins and/or minerals suspended within, or otherwise combined with, one or more edible oils). Such an improved stability generally results in the compositions of the invention having an enhanced stability and/or a longer shelf life than would otherwise be achievable, and is likely a result of the solid-state water-soluble or other vitamins and/or minerals becoming coated with the one or more edible oils and, thus, protected from degradation. Further, for the same reasons, compositions within the present invention generally result in an enhanced absorption of the B vitamins, or other vitamins and/or minerals, by the body of the mammal. When compositions of the invention are administered to a mammal orally, oil coated vitamins and/or minerals may generally be delivered into the intestinal tract of the mammal before being substantially solubilized, which generally prevents or limits the acidic environment of the mammal's stomach from fully degrading, or otherwise substantially diminishing the effectiveness of, the water-soluble or other vitamins and/or minerals.

DETAILED DESCRIPTION OF THE PREFERRED EMBODIMENTS

The present invention may be understood more readily by reference to the following detailed description of the preferred embodiments.

For purposes of clarity, various terms and phrases used throughout this specification and the appended claims are defined in the manner set forth below. If a term or phrase used in this specification, or in the appended claims, is not defined below, or otherwise in this specification, the term or phrase should be given its ordinary meaning.

Definitions

The phrase "aqueous liquid" as used herein means a liquid that includes water (i.e., water-based), such as a liquid that includes 100% water.

The phrase "aqueous solution" as used herein means a solution in which water functions as, or is, a dissolving medium or solvent.

The phrase "antioxidant agent" as used herein means an agent that can prevent or reduce an oxidation, degradation and/or other decomposition that would otherwise occur to components or ingredients of the compositions of the invention, such as water-soluble vitamins and/or minerals and/or edible oils. Antioxidant agents include, but are not limited to, ascorbyl palmitate, various tocopherol mixtures, acids, such as citric acid and ascorbic acid, herbal extracts, such as a Rosemary, Sage, Oregano, Ginger, Marjoram or Rosemary Oleoresins extract, plant phenols, such as Vanillin, ellagic acid and Resveratrol, and synthetic antioxidants, such as tertiary butylhydroquinone (TBHQ), butylated hydroxyamisole (BHA) or butylated hydroxytoluene (BHT), or mixtures thereof. A wide variety of antioxidant agents are commercially available from sources known by those of skill in the art.

The phrase "capable of being mixed with one or more edible oils" as used herein in connection with one or more water-soluble vitamins and/or minerals means that the one or more water-soluble vitamins and/or minerals has an ability to be mixed with one or more edible oils, or a combination thereof, for example, as is described herein, and preferably has an ability to at least temporarily be uniformly distributed in, or suspended within, the one or more edible oils (i.e., the particles of the one or more water soluble-vitamins and/or minerals preferably do not settle out, or form clumps, masses, agglomerates or precipitates, when combined with one or more edible oils).

The phrase "cardiovascular disease" as used herein means disease of the heart and/or circulatory system, including the blood vessels (arteries, veins and/or capillaries), for example, high blood pressure, a stroke, an aneurysm, a heart attack, coronary artery disease or coronary heart disease. Cardiovascular disease currently is the leading cause of death for human beings in the United States, and is a serious problem for people around the world. Elevated cholesterol has been linked with an increased risk of cardiovascular disease. A lipid profile is a conventional blood test that measures total cholesterol, triglycerides and HDL cholesterol. LDL cholesterol is then calculated from the results. A lipid profile is one measure of a human's risk of cardiovascular disease. According to the American Heart Association ("AHA"), 102 million Americans currently have borderline high or high cholesterol and, therefore are at an increased risk for heart disease. The AHA indicates that a 10% decrease in cholesterol levels can reduce the risk of heart disease by up to 30%.

The term "cholesterol" as used herein means a soft, waxy substance that is generally found among the lipids (fats) in the bloodstream, and in the cells, of mammals. Cholesterol can be an important part of a healthy body because it is used to form cell membranes and some hormones, and is generally necessary for other functions. However, a high level of cholesterol in the blood (hypercholesterolemia) is a major risk factor for coronary heart disease, which generally leads to heart attacks. Cholesterol cannot dissolve in the blood. Is has to be transported to, and from, cells by special carriers (lipoproteins). There are several kinds of cholesterol, which include low-density lipoprotein (LDL) and high-density lipoprotein (HDL). Established parameters for total blood cholesterol levels are set forth below.

Total Blood Cholesterol Levels

Healthy (Desirable) Cholesterol Level: Less than 200 mg/dL
Borderline High Risk Cholesterol Level: 200-239 mg/dL
High Risk Cholesterol Level: 240 mg/dL and above If the total cholesterol level of a human being is less than 200 mg/dL, a risk of having a heart attack is generally relatively low (unless other risk factors exist). Human beings that have a cholesterol level from 200-239 mg/dL are borderline high risk, and have a greater risk of having a heart attack and/or stroke. Human beings that have a cholesterol level of 240 mg/dL or above have a still greater risk of having a heart attack and/or stroke. Generally, human beings who have a total cholesterol level of 240 mg/dL have twice the risk of having a heart attack as human beings that have a total cholesterol level of 200 mg/dL. Currently, about 20% of the U.S. population has a high-risk blood cholesterol level.

The phrase "cold temperature" as used herein means a temperature that generally ranges from about 2° C. to about 8° C. (from about 36° F. to about 46° F.).

The term "component" as used herein in connection with a composition of the invention means an ingredient, or combination of ingredients, used to prepare the composition, or a portion, part, element, layer, surface or area of the composition, depending upon the context in which this term is used, which may readily be determined by those of skill in the art. Components of compositions of the invention may include, for example, water- or oil-soluble vitamins and/or minerals, edible oils, suspending agents, antioxidants, diluents, emulsifiers and other ingredients.

The term "composition" as used herein means a product that results from the combining of more than one ingredient.

The phrase "cool temperature" as used herein means a temperature that generally ranges from about 8° C. to about 15° C. (from about 46° F. to about 59° F.).

The phrase "Daily Reference Value" (DRV) as used herein means a label reference value set by the U.S. Food and Drug Administration ("FDA") for use in declaring the nutrient content of a food or other edible composition on its label or labeling.

The phrase "Daily Value" (DV) as used herein means a value set by the FDA for assisting consumers in understanding the relative significance of information about the amount of certain water-soluble vitamins and/or minerals in a food or other edible composition in the context of a total daily diet. This value assists consumers in comparing the nutritional values of food products. The Daily Value is determined by the FDA by combining the Reference Daily Intakes (RDIs) and the Daily Reference Values (RDAs) label reference values. The term "Daily Value," thus, refers to the combined set of label reference values.

The phrase "diluent" as used herein means one or more substances, agents or compositions that has an effect of diluting, rendering less potent, thinning, weakening and/or facilitating a physical separation of one or more substances, agents or compositions, such as one or more water-soluble vitamins and/or minerals. Diluents may be water or oil soluble. Diluent materials that are suitable for human consumption generally include complex polysaccharides, carbohydrates, smaller sugars (dextrose, sucrose and the like), dicalcium phosphate, tricalcium phosphate, maltodextrin and water. "Anhydrous diluents" as used herein means diluents that preferably do not contain any water (or contain substantially no water), for example, anhydrous ascorbic acid. A wide variety of diluents and anhydrous diluents are commercially available from sources known by those of skill in the art.

The term "dispersion" as used herein means a two-phase system in which one phase generally consists of substantially finely-divided particles, which may be in the colloidal size range, that are typically distributed throughout a bulk substance, the particles being the "disperse" or "internal" phase and the bulk substance being the "continuous" or "external" phase. Under natural conditions, the distribution may not be uniform. Under controlled conditions, however, the uniformity can generally be increased by an addition of wetting or dispersing agents (surfactants), such as one or more fatty acids, or a combination thereof. Dispersions include, for example, liquid/liquid forms (emulsions) and solid/liquid forms (solutions or colloidal dispersions).

The term "edible" as used herein means capable of being eaten, consumed and/or ingested by a mammal, or otherwise introduced into a body of a mammal, for example, in a form of a suppository, without being toxic or otherwise harmful to the mammal or, if the mammal is pregnant or lactating, to a developing fetus or a breast-feeding baby of the mammal.

The phrase "edible oils" as used herein means oils, or components thereof, such as fatty acids, that are edible, and that may be employed in pharmaceutical or other compositions for an oral administration, or for administration in a form of a suppository. Edible oils include, but are not limited to, vegetable oils, including, Evening Primrose oil, Black Currant seed oil, Borage oil, Borage seed oil, safflower oil, safflower seed oil, sunflower oil, sunflower seed oil, sesame seed oil, peanut oil, walnut oil, almond oil, olive oil, olive seed oil, avocado oil, avocado seed oil, pumpkin seed oil, corn oil, cod liver oil, soy oil, soybean oil, coconut oil, palm oil, palm kernel oil, rapeseed oil, flaxseed (linseed) oil, cotton seed oil, tung oil, palmolein oil, mustard seed oil, oiticica oil and castor oil, and marine oils (including "fish oils"), such as those that are obtained from aquatic life forms, either directly or indirectly, particularly oily fish and components thereof, and combinations thereof. Other edible oils are known by those of skill in the art. A wide variety of edible oils are commercially available from sources known by those of skill in the art.

The phrase "effective amount" and "in an amount that is effective for" as used herein in connection with one or more vitamins, minerals, edible oils and/or compositions generally means an amount of the one or more vitamins, minerals, edible oils and/or compositions that is effective to provide, or enhance, a nutritional, health and/or medical benefit to a mammal, such as a human being. Using the information that is provided herein, and information that is known, those of ordinary skill in the art can readily determine an amount of one or more vitamins, minerals, edible oils and/or compositions that would be effective for providing, or enhancing, a nutritional, health and/or medical benefit to a wide variety of mammals under a wide variety of different nutritional, health or medical situations.

The phrases "emulsifier" and "emulsification agent" as used herein mean any substance, agent or composition that causes, or aides in, a formation of an emulsion. Edible emulsifiers include, for example, egg yolk, egg lecithin, soy lecithin and mono- and di-glycerides. A wide variety of edible emulsifiers are commercially available from sources known by those of skill in the art.

The term "emulsion" as used herein means any mixture of two liquids that do not normally mix (i.e., they may be immiscible between themselves), such as one or more edible oils, or a combination thereof, and water (or a water-containing substance or composition). Preferably, these emulsions are mixtures that are stable and/or homogeneous. However, they can be true colloids or less stable mixtures, which tend to separate. Emulsions are generally comprised of a continuous phase and a disperse phase. For example, in an "oil-in-water" (o/w) emulsion, generally water (or a water-containing substance or composition) is the continuous phase and oil and/or fat (or an oil- and/or fat-containing substance or composition) is the disperse phase. In contrast, in a "water-in-oil" (w/o) emulsion, oil and/or fat (or an oil- and/or fat-containing substance) is the continuous phase and water (or a water-containing substance or composition) is the disperse phase. (A "water-in-oil" emulsion is a mixture of two or more immiscible liquids that are generally held in suspension by one or more emulsifiers, and in which one or more oils constitutes the "continuous phase" and water or an aqueous solution is the "disperse phase.") The diameters of disperse phase droplets commonly range from about 1 to about 10 μm. Some emulsions can be broken down (i.e. the liquids separated) by factors such as mechanical manipulation, chemical effects and/or time.

The phrase "essential fatty acids" as used herein means fatty acids that are necessary for mammals, but that are not synthesized by the body, for example, linoleic, linolenic and arachidonic acids. Essential fatty acids are commercially available from sources known by those of skill in the art.

The term "excipient" as used herein means a substance that can be used as a "filling agent" in a medication, such as a suppository. One or more active ingredients of a composition may be dissolved in, or mixed with, an excipient. For example, some suppositories may be made using known methods and equipment with a greasy excipient, such as cocoa butter, in which one or more active substances are diluted.

The term "fat" as used herein means any of the various saturated and/or unsaturated (including monounsaturated and polyunsaturated), hydrogenated or unhydrogenated, soft solid, semisolid and/or solid organic compounds that generally comprise the glyceride esters of fatty acids and associated phosphatides, sterols, alcohols, hydrocarbons, ketones and/or related compounds, and includes components of fats, such as fatty acids, glycerides and ethyl esters containing fatty acids, or components thereof, and mixtures or other combinations of one or more fats. There is generally no chemical difference between fats and oils, with the only distinction being that fats are generally solid at room temperature and oils are generally liquid at room temperature. Components of fats and oils include, but are not limited to, fatty acids, glycerides (mono-, di- and tri-), ethyl and other esters of fatty acids, as well as components thereof and combinations thereof. A wide variety of edible fats are commercially available from sources known by those of skill in the art.

The phrase "fatty acids" as used herein means carboxylic acids that generally are derived from, or contained in, an animal, vegetable or other fat or oil, whether saturated, unsaturated, monounsaturated, polyunsaturated, aromatic, essential, nonessential, in a cis or trans form, in the ethyl esters, mono-, di- or tri-glycerides, free fatty acids or other forms, and components and combinations of the foregoing. Fatty acids include, but are not limited to, omega-3 fatty acids, omega-6 fatty acids and omega-9 fatty acids, and the specific fatty acids identified below:

| Common Name | Number of Carbon Atoms | Number of Double Bonds | Fat or Oil Source |
|---|---|---|---|
| FATTY ACIDS | | | |
| Butyric Acid | 4 | 0 | Butterfat |
| Caproic Acid | 6 | 0 | Butterfat |
| Caprylic Acid | 8 | 0 | Coconut Oil |
| Capric Acid | 10 | 0 | Coconut Oil |
| Lauric Acid | 12 | 0 | Coconut Oil |
| Myristic Acid | 14 | 0 | Palm Kernel Oil |
| Palmitic Acid | 16 | 0 | Palm Oil |
| Palmitoleic Acid | 16 | 1 | Animal Fats |
| Stearic Acid | 18 | 0 | Animal Fats |
| Oleic Acid | 18 | 1 | Olive Oil |
| Linoleic Acid | 18 | 2 | Corn Oil |
| Alpha-Linolenic Acid (ALA) | 18 | 3 | Flaxseed (Linseed) Oil |
| Gamma-Linolenic Acid (GLA) | 18 | 3 | Borage Oil |
| Gadoleic Acid | 20 | 1 | Fish Oil |
| Arachidonic Acid (ARA or AA) | 20 | 4 | Liver Fats, Peanut Oil, Fish Oil |
| Eicosapentaenoic Acid (EPA) | 20 | 5 | Fish Oil |
| Behenic Acid | 22 | 0 | Rapeseed Oil |
| Erucic Acid | 22 | 1 | Rapeseed Oil |
| Docosahexaenoic Acid (DHA) | 22 | 6 | Fish Oil |
| Lignoceric Acid | 24 | 0 | Most Fats |

Other fatty acids are known by those of skill in the art. A wide variety of fatty acids are commercially available from sources known by those of skill in the art. Also, edible oils can be separated into their component fatty acids on a capillary column in a gas chromatograph, and the relative fatty acid contents measured. Additional information concerning fatty acids is readily available from the Fatty Acid Producer's Council (New York, N.Y.).

The phrase "fill material" as used herein means a substance, material or composition that is injected or inserted into one or more hollow oral dosage forms or hollow suppository forms.

The phrase "freezing temperature" as used herein means a temperature that generally ranges from about −25° C. to about −10° C. (from about −13° F. to about 14° F.).

The phrase "fungal oil" as used herein means an oil that is derived, or obtained, from a fungal source, whether modified or unmodified, such as Mucor javanicus, either directly or indirectly. As used herein, the phrase "fungal oil" includes, but is not limited to, one or more individual components present in fungal oil, such as DHA, arachidonic acid or other fatty acids. A wide variety of fungal oils are commercially available from known sources, such as Martek Corp. (Columbia, Md.).

The phrase "hollow oral dosage forms" as used herein means edible dosage forms for oral administration, such as hard or soft gel capsules, gelcaps or other capsules, microcapsules or caplets (which include gelatin or some other suitable or conventional material, such materials being known by those of skill in the art), which have not yet been partially of fully filled with a substance, material or composition to be enclosed, contained or included therein (i.e. shells that do not yet contain all of the substance or composition to be enclosed, contained or included within the oral dosage forms, and which may be empty). A wide variety of hollow oral dosage forms are commercially available from sources known by those of skill in the art.

The phrase "hollow suppository forms" as used herein means dosage forms for an administration to a mammal in a rectal, vaginal, urethral or other orifice of the body, such as hard or soft gel capsules, gelcaps or other capsules, microcapsules or caplets (which include gelatin or some other suitable or conventional material, such materials being known by those of skill in the art), which have not yet been partially of fully filled with a substance, material or composition to be enclosed, contained or included therein (i.e. shells that do not yet contain all of the substance or composition to be enclosed, contained or included within the hollow suppository form, and which may be empty). A wide variety of hollow suppository forms are commercially available from sources known by those of skill in the art.

The term "hydrogenation" as used herein means a chemical process by which hydrogen is added to unsaturated fatty acids to produce partially or fully hydrogenated oils. Hydrogenation converts unsaturated bonds in the oil into saturated bonds. Some of the double bonds may be eliminated, while others may be incompletely transformed. These double bonds may be transformed from the natural "cis" configuration to the "trans" configuration.

The phrase "initially" as used herein means at the beginning or start, for example, of a process, or step thereof, but not necessarily thereafter, such as at the end of a process, or step thereof.

The term "mammal" as used herein means a member of the class Mammalia, and includes, but is not limited to, developing fetuses, human beings (babies, infants, children, adults, pregnant woman, lactating women, women having childbearing potential that are attempting to become pregnant and the like) and animals.

The phrase "marine oil" as used herein has the meaning described above, and includes, but is not limited to, "fish oil" and one or more individual components of marine oil, such as an omega-3 fatty acid, including DHA, EPA, ALA, or a combination thereof. Marine oils include, for example, herring oil, cod oil, anchovy oil, tuna oil, sardine oil, menhaden oil and algae oil. Aquatic lifeforms that are employed to produce marine oils include, for example, farm-raised or wild, freshwater or salt-water, fish and shellfish, such as herring, salmon, salmonoids, gadoids, shrimp, cod, carp, tilapia, perch, trout, sturgeon, krill, tuna, flat fish, anchovies, sardines, menhaden, shrimp, eels and seals. Marine oils may also be obtained from marine organisms, such as calanus (*Calanus finmarchicus*), a 3-4 mm copepod, algae and microalgae, for example, diatoms and dinoflagellates. A wide variety of marine oils are commercially available from sources known by those of skill in the art.

The term "medicament" as used herein means a substance, agent or composition that promotes or enhances a recovery from an injury, illness, disease or disorder (i.e., that improves the medical condition of a mammal).

The term "minerals" as used herein means minerals that are edible, and includes those in an elemental, salt or other form. Examples of minerals include, but are not limited to, calcium, copper, fluorine, iodine, iron, magnesium, manganese, molybdenum, potassium, phosphorous, selenium and zinc, in an elemental form, or in the form of carbonates, oxides, phosphates, silicates, sulfates, sulfides or other forms. Many minerals are inorganic compounds that are necessary for life and good nutrition, such as calcium, copper, iron, magnesium, potassium and zinc. Additional information about minerals, including an extensive list of minerals, is present at the web site http://en.wikipedia.org/wiki/Minerals. A wide variety of minerals are commercially available from sources known by those of skill in the art.

The term "nutrient" as used herein means an agent, substance or composition that is preferably soluble in water and insoluble in oil, and that is beneficial to the growth, development and/or health of a mammal, or that provides or enhances a nutritional, medical and/or other health benefit to a mammal, and includes, but is not limited to, vitamins, minerals, medicaments and other active agents.

The term "oil" as used herein means a fat that generally is viscous, liquid or liquefiable at room temperature, and includes mixtures and other combinations of one or more oils and/or components of oils, such as fatty acids, glycerides and/or ethyl esters of fatty acids (or components thereof). Oils may be derived, or obtained, from animal, marine, algae, fungal, mineral, plant (including vegetables and plant seeds), fruit, nut, synthetic or other sources, and are generally composed largely of glycerides of the fatty acids, particularly oleic, palmitic, stearic and linolenic. Oils may be hydrogenated or non-hydrogenated, and saturated or unsaturated (including monounsaturated and polyunsaturated). Plant sources of oil include, but are not limited to, hydrogenated and non-hydrogenated vegetable oils and plant seed oils, Evening Primrose oil, Black Currant seed oil, Borage oil, Borage seed oil, safflower oil, safflower seed oil, sunflower oil, sunflower seed oil, sesame seed oil, peanut oil, olive oil, olive seed oil, corn oil, avocado oil, avocado seed oil, pumpkin seed oil, soy oil, soybean oil, coconut oil, palm oil, palm kernel oil, rapeseed oil, flaxseed (linseed) oil, cotton seed oil, tung oil, oiticica oil and castor oil. Examples of fats derived from marine sources include fish oil and algae oil. Other oils are known by those of skill in the art. A wide variety of edible oils are commercially available from sources known by those of skill in the art.

The phrase "oil-insoluble" as used herein in connection with vitamins and/or minerals (and/or other components of the compositions of the invention) means that the vitamins and/or minerals (and/or other components) are substantially oil-insoluble (i.e., that most or all of the vitamins and/or minerals, or particles thereof, are not able to form a true solution with one or more oils, or a combination thereof).

The phrase "oil-soluble" as used herein in connection with vitamins and/or minerals (and/or other components of the compositions of the invention) means that the vitamins and/or minerals (and/or other components) are substantially soluble in oil (i.e., that most or all of the vitamins and/or minerals, or particles thereof, are able to form a true solution with one or more oils, or a combination thereof).

The phrase "oral dosage forms" as used herein means edible dosage forms that are suitable for an oral administration to a mammal, such as hard or soft gel or other capsules, microcapsules and caplets, and the like. Such oral dosage forms may include in their outer structure gelatin or some other suitable or conventional material. Such materials are known by those of skill in the art, and are commercially available from sources known by those of skill in the art.

The terms "phytosterols" and "plant sterols" as used herein means a group of naturally occurring substances (sterols or fatty alcohols) that typically are found in, and may be derived from (using methods and equipment known by those of skill in the art), fruits, vegetables, vegetable oils (including corn oils), plants, nuts, grains, seeds, wood pulp, leaves, cereals, rice bran, wheat germ, soybeans and/or other sources, and are poorly absorbed by mammals. Plant sterols have a chemical structure that is similar to that of cholesterol. They can be used as individual sterols, stanols and their esters, or in combinations, as may be found in plant products. Plant sterols have a role in plants that is similar to that of cholesterol in mammals, e.g. forming cell membrane structures. Plant sterols fall into one of three categories: 4-desmethylsterols (containing no methyl groups); 4-monomethylsterols (containing one methyl group) and 4,4-dimethylsterols (containing two methyl groups). The most common plant sterols are β-sitosterol, campesterol and stigmasterol and, structurally, these compounds are very similar to cholesterol, belonging to the class of 4-desmethylsterols. Preferably, plant sterol mixtures contain a combined weight of at least about 80 percent β-sitosterol, campesterol and stigmasterol. Plant sterols generally have an ability reduce an intestinal absorption of cholesterol by mammals (i.e. they may function as serum cholesterol-lowering agents in mammals). They may function by interfering with the body's absorption of dietary cholesterol during digestion and/or by promoting a release of cholesterol, thus, helping to maintain healthy cholesterol levels. [Mayo Clin Proc 78:965-78 (2003) and AJCN 74:33-43 (2001).] As a result, plant sterols may reduce a risk of cardiovascular disease in mammals. Plant sterols include, but are not limited to, β-sitosterol, β-sitostanol, stigmasterol, Δ5-avenasterol, campesterol, campestanol and brassicasterol, and may be hydrogenated or non-hydrogenated. Other plant sterols are known by those of skill in the art. A typical plant sterol mixture would be about 70% sitosterol, 20% stigmasterol and 10% campesterol. Plant sterols are commercially available from sources known by those of skill in the art. For example, CardioAid™-M phytosterols are commercially available from Archer Daniels Midland Company (Decatur, Ill.) under ADM product code 040550.

The phrases "phytosterol esters" and "plant sterol esters" as used herein mean fatty acid or other esters of phytosterols. Phytosterol esters may be produced, for example, using Rapeseed oil, DHA oil, EPA oil, other omega-3 oils and/or other triglycerides (chains of high-energy fatty acids) or edible oils, and by an esterification of plant sterols and/or stanols with fatty acids, which are preferably food-grade (by the attachment of fatty acids). Phytosterol esters include, but are not limited to, fatty acid esters of β-sitosterol, β-sitostanol, stigmasterol, Δ5-avenasterol, campesterol, campestanol and brassicasterol. Other phytosterol esters are known by those of skill in the art. Phytosterol esters are commercially available from sources known by those of skill in the art. For example, CardioAid™-S phytosterol esters are commercially available from Archer Daniels Midland Company (Decatur, Ill.) under ADM product code 040087. Plant sterol esters may be measured by the known method entitled, "Determination of the Sterol Content in Margarines, Halvarines, Dressings, Fat Blends and Sterol Fatty Acid Ester Concentrates by Capillary Gas Chromatography," which was developed by Unilever United States, Inc., and is dated Feb. 1, 2000.

The phrase "plant seed oil" as used herein means an oil that is extracted, or otherwise obtained, from a seed of a plant, either directly or indirectly, particularly oily seeds, including one or more individual components thereof and mixtures thereof. Plant seed oils include, but are not limited to, Black Currant seed oil, Borage seed oil, safflower seed oil, sunflower seed oil, sesame seed oil, avocado seed oil, pumpkin seed oil, olive seed oil, coconut seed oil, rapeseed oil, flaxseed (linseed) oil, cottonseed oil and tung oil. Other plant seed oils are known by those of skill in the art. Plant seed oils are commercially available from sources known by those of skill in the art.

The phrase "plant oil" as used herein means an oil that is extracted, or otherwise obtained, from a plant, either directly or indirectly, particularly oily plants, including one or more individual components thereof, and mixtures thereof. Plant oils include, but are not limited to, Evening Primrose oil, Borage oil, safflower oil, sunflower oil, peanut oil, walnut oil, almond oil, avocado oil, olive oil, corn oil, soy oil, soybean oil, coconut oil, palm oil, palm kernel oil and castor oil. Other plant oils are known by those of skill in the art. Plant oils are commercially available from sources known by those of skill in the art.

The phrases "plant stanols" and "stanols" as used herein mean naturally occurring substances that are hydrogenated compounds of the respective plant sterols, typically by an addition of two hydrogen atoms. Plant stanols generally are saturated plant sterols, such as β-sitostanol, campestanol and stigmastanol, and occur in nature at lower concentrations than sterols. Plant stanol esters may be produced using plant stanols in the same manner described hereinabove in connection with phytosterol esters. Additional information concerning plant stanols, and esters thereof, is present in Cater N. B., "Plant Stanol Ester: Review of Cholesterol-Lowering Efficacy and Implications for Coronary Heart Disease Risk Reduction," Preventative Cardiology 2000; 3, 121-130.

The phrase "plant stanol esters" as used herein mean fatty acid or other esters of plant stanols. Plant stanol esters may be prepared, for example, by esterifying a mixture of plant stanols derived from one or more edible oils or byproducts of the kraft paper pulping process with fatty acids, which are preferably food-grade. A plant stanol ester mixture preferably contains a combined weight of at least about 80 percent sitostanol and campestanol. Plant stanol esters may be measured by the following known methods, which were developed by McNeil Consumer Healthcare dated Feb. 15, 2000: (1) "Determination of Stanols and Sterols in Benecol Tub Spread;" (2) "Determination of Stanols and Sterols in Benecol Dressing;" (3) "Determination of Stanols and Sterols in Benecol Snack Bars;" or (4) "Determination of Stanols and Sterols in Benecol Softgels."

The term "plurality" as used herein means more than one, such as two, three, four, five, six, seven, eight, nine, ten, fifteen, twenty or the like.

The phrase "properly disintegrate" as used herein in connection with compositions of the invention means that the compositions at least partially, and preferably fully, disintegrate (decompose or break down), thereby releasing one or more, and preferably all, of the substances that are present in the compositions, such as those that can provide or enhance a nutritional, medical or other health benefit to a mammal, for example, vitamins, minerals and fatty acids (i.e., the one or more substances are generally no longer partially or fully enclosed, or otherwise contained, within an enclosing or other material, composition or vehicle, such as an outer shell of a gel capsule.)

The phrase "Reference Daily Intakes" (RDIs) as used herein means a label reference value set by the FDA for use in declaring the nutrient content of a food or other edible composition on its label or labeling. The FDA has replaced label reference values created in 1973 that are known as "U.S. Recommended Daily Allowances" (U.S. RDAs) with RDIs.

The phrase "room temperature" as used herein means the temperature in a room, which generally ranges from about 15° C. to about 30° C. (from about 59° F. to about 86° F.), and more usually ranges from about 21° C. to about 23° C. (from about 70° F. to about 74° F.). The "ambient temperature" of a room is "room temperature."

The phrase "safe for consumption" in connection with compositions of the invention, or components thereof, such as vitamins, minerals, edible oils, emulsifiers, diluents, antioxidant agents, suspending agents and the like, means that the compositions, and the components contained therein, in reasonable quantities administered for reasonable periods of time (such as those quantities and periods of time described herein, or as otherwise recommended for a particular mammal by a physician, veterinarian or other skilled clinician, which may vary for different types of mammals (and different types of human beings), and according to size, weight, sex, medical status and other factors, do not cause, or present a reasonable risk of causing, harm, illness, disease, injury, disorder or deformity to a mammal.

The phrase "shelf life" as used herein means an ability of a composition of the invention to remain "fresh" (i.e. to not have, or develop, one or more off flavors or tastes, or other undesirable tastes and/or odors), generally under room temperature conditions. For example, commercially available food products can lose some or all of their "freshness" when an edible fat or oil, or another ingredient thereof, undergoes an oxidation, degradation and/or decomposition.

The phrase "soft gel capsule" as used herein typically means a one-piece, hermetically sealed soft gelatin shell that is filled with a material, substance or compositions (a "fill"). The soft gel shell is generally comprised of a film-forming material, such as gelatin, for example type A and/or type B, and water-dispersible or water-soluble plasticizers (to impart flexibility). Soft gel capsules may be produced using known methods and conventional machinery.

The phrases "solid-state" and "solid-state form" as used herein mean having a form that is substantially a soft solid, a semisolid or a solid (i.e. not liquid), including size-reduced solids, for example, powders (finely divided powders, amorphous powders, milled crystalline powders and the like), granules, particles and milled materials. Methods are known by those of skill in the art for size reducing solids, such as milling, grinding, cutting and like methods. Solid-state vitamins and/or minerals, for example, preferably have a size ranging from about 10 microns to about 40 mesh, and typically are under 100 mesh.

The phrase "solution" as used herein means a mixture of two or more substances, agents and/or compositions in which at least one of the substances, agents and/or compositions has partially, substantially or fully (preferably fully) dissolved in at least one of the other substances, agents and/or compositions. Preferably, the resulting solution is a homogeneous mixture of two or more substances, agents and/or compositions. Typically, when a first substance (solute) dissolves in a second substance (a solvent), the first substance may lose its crystalline form and become molecularly or ionically dispersed in the solvent to form a true solution. A true solution is a uniformly dispersed mixture at the molecular or ionic level of one or more substances (solutes) in one or more other substances (the solvent). These two parts of the solution are called phases.

The terms "substantial" and "substantially" as used herein, unless stated otherwise, mean considerable or large in quantity, extent, value, degree or importance, and include most (mostly) or an entirety (full or fully) of an amount, extent, value, degree or importance.

The phrase "substantially degraded" as used herein in connection with vitamins and/or minerals, or particles or mixtures thereof, means that the vitamins and/or minerals, or particles or mixtures thereof, are sufficiently degraded (broken down or otherwise reduced to a less complex form or structure) that they cannot reasonably provide any medical, nutritional, health and/or other benefit to a mammal.

The term "suppository" as used herein means a mass that may have a nutritional, medical and/or other health benefit to a mammal, and that is generally introduced into a rectal, vaginal, urethral or other orifice of the mammal's body. Generally, suppository bases (outer material thereof) are solid at room temperature, but melt or dissolve at body temperature. Commonly used bases include cocoa butter, glycerinated gelatin, hydrogenated vegetable oils, polyethylene glycols of various molecular weights and fatty acid esters of polyethylene glycol. Suppositories may be in a solid form or in a form of a hollow shell that is filled with a fill.

The phrase "suspending agent" as used herein means a substance, material or composition that has an ability to initiate, permit, promote, enhance or maintain a suspension of one or more soft-solid, semi-solid or solid components in a semi-liquid or liquid vehicle and, optionally, to provide a nutritional, medical or other health benefit, or a combination thereof, to a mammal. Examples of suspending agents include, for example, phytosterols, phytosterol esters, plant stanols, plant stanol esters, lecithin, yellow beeswax and sunflower oil. A wide variety of suspending agents are commercially available from sources known by those of skill in the art.

The term "suspension" as used herein means an incorporation of one or more solid-state components into a semi-liquid or liquid vehicle, and includes colloidal and other types of suspensions. Preferably, a suspension is a uniform suspension (i.e. the components are uniformly or evenly present within a semi-liquid or liquid vehicle). If the particle sizes of component particles are larger than colloidal dimensions (i.e., they are not small enough to pass through filter membranes), the component particles may have a tendency to precipitate (if they are heavier than the suspending medium) or agglomerate and rise to the surface (if they are lighter than the suspending medium). In both cases, the component particles may "settle out" of the suspension.

The phrase "temporarily suspended" as used herein in connection with one or more vitamins and/or minerals and one or more edible oils means that the one or more vitamins and/or minerals are substantially or fully (preferably fully) suspended in the one or more edible oils for a period of time that is sufficient to permit the one or more vitamins and/or minerals and the one or more edible oils preferably to be uniformly inserted into one or more (preferably two or more) hollow oral dosage forms or hollow suppository forms, such as hollow gel capsules, gelcaps, or caplets (i.e., in a manner that substantially the same amount of the one or more vitamins, minerals and/or edible oils becomes inserted into the one, two or more hollow oral dosage forms or hollow suppository forms). Such a period of time may vary depending upon a wide variety of factors, such as the numbers and types of the vitamins and/or minerals and edible oils being employed, the number of hollow oral dosage forms or hollow suppository forms being filled and the like, and can readily be determined by those of skill in the art.

The phrase "uniformly inserted into" when used herein in connection with one or more water-soluble vitamins and/or minerals, or particles thereof, one or more edible oils and/or one or more hollow oral dosage forms or hollow suppository forms means that approximately the same quantities of the one or more water-soluble vitamins and/or minerals and/or the one or more edible oils are generally placed into each of the one or more hollow oral dosage forms or hollow suppository forms being filled (whether they are being partially or completely filled). For example, if one hundred hollow soft gel capsules, gelcaps, or caplets are being filled with one or more edible oils having one or more water-soluble vitamins and/or minerals suspended therein, approximately the same quantities of the one or more water-soluble vitamins and/or minerals and the one or more edible oils will generally be present in each of the soft gel capsules, gelcaps, or caplets after the filling operation.

The phrase "uniformly distributed in" when used herein in connection with one or more water-soluble vitamins and/or minerals, or particles thereof, one or more edible oils, hollow oral dosage forms, hollow suppository forms and/or compositions of the invention means that the one or more water-soluble vitamins and/or minerals, or particles thereof, are generally, and at least temporarily, evenly distributed or suspended within, or throughout, the one or more edible oils.

The phrase "uniform mixture" as used herein in connection with a mixture of two or more water-soluble vitamins and/or minerals and/or two or more edible oils means a mixture (a combination, blend or other association of substances, agents or compositions) that has one or more of its components generally uniformly or evenly dispersed therein. Liquids that are uniformly dispersed may be solutions.

The phrase "uniform quantity" as used herein in connection with one or more water-soluble vitamins and/or minerals, or particles thereof, one or more edible oils, one or more other components of the compositions of the invention, hollow oral dosage forms, hollow suppository forms, oral dosage forms and/or compositions of the invention means that substantially or completely the same quantity of the one or more water-soluble vitamins and/or minerals, or particles thereof, one or more edible oils and/or one or more other components of the compositions of the invention is injected or inserted into, or otherwise included in, two or more hollow oral dosage forms, oral dosage forms or hollow suppository forms. For example, a uniform quantity as this term may be employed in connection with 50 oral dosage forms of the compositions of the invention means that all, or substantially all, of the 50 oral dosage forms include approximately or fully the same quantities of the same components of the compositions of the invention, or at least those components of the compositions that provide or enhance a medical, nutritional and/or other health benefit to a mammal, such as the one or more water-soluble vitamins and/or minerals and the one or more edible oils.

The phrase "unit dosage form" as used herein means one individual dosage form for an administration to a mammal, either orally or in a form of a suppository, such as one hard or soft gel capsule containing a composition of the invention. Compositions of the invention in the form of one or more unit dosage forms generally at least initially contain a suspension or dispersion that is injected or otherwise inserted into one or more oral hollow dosage forms or hollow suppository forms, wherein the oral hollow dosages or hollow suppository forms are sealed (i.e. the contents thereof generally are not exposed to air or oxygen).

The term "vitamin B6" means know chemical forms of vitamin B6 including, but not limited to pyridoxine, pyridoxamine, and pyridoxal, all of which are commercially available from sources known by those of skill in the art.

The term "vitamin B9" means folic acid folate or one or more natural isomers of reduced folate, including but not limited to L-methylfolate, L-5-methyl-tetrahydrofolate, L-5-methyl-tetrahydrofolic acid, (6S)-tetrahydrofolic acid, (6S)-5-methyl-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, (6S)-5-methyl-tetrahydrofolic acid and polyglutamyl derivatives of tetrahydrofolate acid, which are commercially available from sources known by those of skill in the art.

The term "vitamin B12" means known chemical forms of vitamin B12 including, but not limited to, cyanocobalamin, cobalamin, and reduced forms of cobalamin, and also includes all forms both bound and unbound to recombinant intrinsic factor, which are commercially available from sources known by those of skill in the art.

The phrase "without being degraded" as used herein in connection with water-soluble vitamins, minerals and/or edible oils means that no degradation, or substantially no degradation, preferably occurs. When substantially no degradation occurs, some minimal degradation may still occur, but the amount of such degradation is generally insufficient to prevent or reduce the nutritional, medical or other health benefits provided by the nutrient or edible oil to the mammal.

The phrase "water-soluble" as used herein in connection with water-soluble vitamins and/or minerals means that the vitamins and/or minerals dissolve partially or fully (and preferably fully) in water, and preferably form an equilibrium concentration of at least about 0.001 mg/mL at 25° C.

Edible Oils

Any one or more of a wide variety of edible oils, or combinations thereof, may be employed in the compositions of the invention, including, but not limited to, those specifically discussed herein. Because of the nutritional, medical and/or other health benefits that they can provide to mammals, edible oils that are preferred for use in the compositions of the invention are those that are, or are rich in (contain large quantities of), essential fatty acids, omega-3 fatty acids, omega-6 fatty acids and/or omega-9 fatty acids, particularly DHA, EPA, ARA, AA, ALA or GLA, ocosapentaenoic acid, eicosatetraenoic acid, moroctic acid, heneicosapentenoic acid, gamma-linolenic acid, linoleic acid, arachidonic acid and oleic acid. As a result of an enhanced stability, such fatty acids are preferably present in their ethyl esters or triglycerides forms. The most preferred edible oils for use in the compositions of the invention are those that are, or are rich in, omega-3 fatty acids and/or essential fatty acids, such as DHA.

The edible oils that may be employed in the compositions of the invention are commercially available from sources known by those of skill in the art. Sources for these edible fats and oils include, for example, Martek Corp. (Columbia, Md.), Ocean Nutrition Canada, Ltd. (Bedford, Nova Scotia, Canada), DSM (Heerlen, NL), Pronova Biocare AS (Lysakar, Norway), Napro AS (Brattvaag, Norway), Berg Lipotech AS (Norway), ADM Food Oils (Decatur, Ill.), and Oilseeds International, Ltd. (San Francisco, Calif.).

Edible oils, such as omega-3 marine oils, are generally commercially available in the ethyl esters, triglycerides or free fatty acids forms. The ethyl esters form of edible oils result from breaking apart the original triglyceride molecules through the known process of "ethylation," which is performed to increase or concentrate the level of omega-3 fatty acids, while removing the less desirable fatty acids. Ethyl esters of EPA and DHA are available from DSM (Heerlen, NL) under the name Ropufa® 75 n-3 EE, and from other oil suppliers described herein.

The triglycerides form of edible oils generally consists either of an unconcentrated fish oil (about 18% EPA and about 12% DHA), or of a concentrated fish oil that has been reconverted (re-esterified) back to the tri-glycerides form. In the processing of marine and other edible oils, the objective is generally to remove existing free fatty acids, monoglycerides and diglycerides to form more stable compositions of the fatty acids, which is the triglycerides or ethyl esters forms of the fatty acids.

The fatty acids form of edible oils generally results from saponification and neutralization of the triglycerides, using known techniques, whereby the glycerol backbone of the triglycerides is generally severed, leaving only the free fatty acid form. Such processing techniques preferably result in the edible oils having an acid value below about 5.0 mg KOH/g and unsaponified matter below about 1.5% w/w.

Methods are also known by those of skill in the art for extracting oil from fish. For example, raw fish can be placed into a cooker and heated to a temperature of about 95°. This temperature can be reached by heating the fish meat directly, or indirectly, with steam. Such heating aids in the coagulation of proteins in the fish meat. As the proteins coagulate, the heating also helps recover fat and water from the fish meat. The cooked fish meat can be collected and conveyed to screw presses, which aid in the removal of any remaining oil and/or water from the fish. The resulting liquid, which is called "pressliquor," undergoes a series of known decanting and separating techniques. Decanters are employed to separate solid fish meat from the liquid. The pressliquor can be pumped into cylindrical bowls and conveyers to rotate. The rotation of the decanter helps to force the solids to the outside of the bowl, where they are collected. The remaining liquid continues through the process. After decanting, the pressliquor can be pumped through a separator. A high-speed rotation of separator plates results in the separation of the oil from the water, resulting in a fish oil. Marine oil can be extracted from aquatic lifeforms other than fish in a similar manner. All of the equipment and techniques employed in extracting marine oil from fish and other aquatic lifeforms are known and/or commercially available.

Methods are also known by those of skill in the art for extracting oil from seeds, including the known solvent extraction and mechanical extraction (cold processing) methods.

Oils that are extracted from fish, plants and other sources may have a pronounced color, flavor and aroma. If the refining of such oils does not cause the amount of water-soluble vitamins and/or minerals present therein to be reduced or eliminated, it is, thus, preferable that edible oils that are employed in the compositions of the invention, and that are extracted from such sources, be refined, deodorized and substantially free of fish meat, flesh, seeds or other solids. Such refinement methods are known by those of skill in the art, and generally result in a clean, "finished" oil product. When some oils, such as Evening Primrose oil, are refined, however, water-soluble vitamins or minerals present in the oils are significantly reduced by the refinement process. Those of skill in the art know which edible oils have their water-soluble vitamins or minerals reduced by refinement processes. Unrefined oils are sometimes referred to as "virgin" or "extra virgin" oils.

Marine (and other) oils employed in the compositions and methods of the invention may preferably be refined and deodorized using methods known in the art. For example, methods for processing marine and other edible fats and oils are described in "Fish Oils: Their Chemistry, Technology, Stability, Nutritional Properties and Uses" (The Avi Publishing Company, Inc., 1967); Marschner et al. U.S. Pat. No. 4,804,555, entitled "Simultaneous Deodorization and Cholesterol Reduction of Fats and Oils;" and A. P. Bimbo, "Production of Fish Oil," *Fish Oils in Nutrition*, Chapter 6, 141-180 (M. E. Stansby ed., New York, Van Nostrand Reinhold); the disclosures of which are expressly incorporated by reference herein.

Both physical refining and chemical refining can generally be employed to refine oils that can be employed in compositions for oral administration or for administration as a suppository. Physical methods include the known filtering, deodorizing and winterization processes. Chemical methods include the known degumming, neutralization and bleaching processes. Additional information concerning the refinement of oils for use in compositions for oral administration is present at the web site www.sanmarkltd.com/processing-.htm.

Marine oil purification is a process in which crude oils are refined to remove fish meat and flesh, as well as other substances that may contribute to off flavor, off odor, undesirable color or keeping quality. The oils can be purified, or fatty acids can be removed from the oils, by degumming the oils (by washing the oils generally using water, salts and acids in order to remove waxes, phosphates and other impurities therefrom). After the impurities are removed from the oils through degumming, the oils can undergo a neutralization process. Alkali can be mixed with the oils to remove free fatty acids, which can contribute to rancidity. A resulting soap/oil mixture can be heated to, for example, 180° F., and pumped through a separator that removes the soap from the oil.

After the above "chemical" refinements have been made, the oils can be subjected to "physical" refinements. The first of these physical refinements is generally the removal of odor compounds from the oils. This can be accomplished by applying a vacuum steam distillation process to the oils. Steam distillation can be followed by winterization, which involves a cooling of the oils. As a result of this cooling process, some oils become crystallized, and can thereafter be removed from other oils using filtration techniques. This results in the oils being more uniform. After winterization, the oils can be bleached and hydrogenised, which processes can stabilize the oils. Bleaching involves the use of clay to remove color and impurities from the oils. The oils can be bleached by heating, for example, to about 130° F., and mixing them with clay. The mixture can be held for several minutes, and then the hot oil can be filtered from the clay and cooled. Hydrogenation can be completed, following bleaching, by pumping pressurized hydrogen into an agitated tank filled with the oils. This is generally done in the presence of a catalyst metal, such as nickel. Hydrogenation can be performed at a temperature, for example, of about 204° C., and a pressure of, for example, 60 psig.

Similar known methods to those described above can be employed with other types of edible oils. Further, other methods known by those of skill in the art can also be employed to purify marine and other types of edible oils, or to remove fatty acids from such oils. Methods for processing marine and other edible fats and oils are well known in the art. (See, for example, "Fish Oils: Their Chemistry, Technology, Stability, Nutritional Properties and Uses" (The Avi Publishing Company, Inc., 1967); Marschner et al. U.S. Pat. No. 4,804,555, entitled "Simultaneous Deodorization and Cholesterol Reduction of Fats and Oils;" A. P. Bimbo, "Production of Fish Oil," *Fish Oils in Nutrition*, Chapter 6, 141-180 (M. E. Stansby ed., New York, Van Nostrand Reinhold).

In order to permit edible oils employed in the compositions of the invention to provide maximum nutritional, health and/or medical benefits, it is preferred that the edible fats and oils not be hydrogenated. As discussed hereinabove, the hydrogenation of marine or other edible oils by decreasing polyunsaturation, including n-3 fatty acid components, generally correspondingly decreases the health value of such oils.

In the United States, there are currently no Reference Daily Intakes (RDIs), Daily Reference Values (DRVs) or Daily Values (DVs) for essential fatty acids or other edible oils. However, the World Health Organization recommends that pregnant and lactating women consume 5% of their daily caloric intake as essential fatty acids. It is recommended that healthy adults consume 4% to 10% of their daily caloric intake as essential fatty acids.

The amount of one or more edible oils that may be included in the compositions of the invention is an amount that is preferably effective for providing or enhancing one or more nutritional, health, medical and/or other benefits to the mammal, and that is safe for consumption by the mammal (i.e., it would not be harmful to the mammal). Those of skill in the art can readily determine such amounts for a wide variety of different edible oils, or combinations thereof. This amount generally ranges from about 0.01 to about 90 weight percent of the total weight of the compositions, and preferably ranges from about 10 to about 80 weight percent, with about 65.15 weight percent being more preferred.

DHA may, for example, optionally be included as a component of the compositions of the invention in an amount that is effective for providing, or increasing the supply of DHA to developing fetuses or babies through, for example, placentas or breast milk, or to other mammals, and that is not harmful to developing fetuses or breast-feeding babies, or to other mammals. The amount of DHA that is preferably present in these compositions ranges from about 0.05 to about 3 weight percent of the total weight of the compositions, and more preferably ranges from about 0.2 to about 0.6 weight percent, with about 0.3 weight percent being most preferred (for pregnant women, lactating women, and women having childbearing potential that are attempting to become pregnant, or for other mammals).

Edible oils are susceptible to oxidation, degradation and decomposition, particularly when they are exposed to oxygen (present in the air or otherwise), or when they are in contact with substances that initiate or catalyze (accelerate the rate of) the oxidation, degradation and/or other decomposition of edible oils, such as free radicals or certain minerals. Free radicals are highly reactive molecular fragments that have one or more unpaired electrons and generally act as initiators or intermediates in oxidation reactions. Minerals, particularly copper, iron, magnesium, manganese, molybdenum and zinc, generally catalyze an oxidation and/or degradation of edible oils. Those of skill in the art know which vitamins, minerals and other water-soluble vitamins initiate or catalyze the oxidation, degradation and/or other decomposition of edible oils. It is, thus, preferred that the compositions of the invention comprise vitamins, minerals and other water-soluble vitamins and/or minerals that do not initiate or catalyze an oxidation, degradation or other decomposition of edible oils.

The amount of oxidation, degradation and decomposition that occurs to an edible oil, or to a composition containing one or more edible oils, can be determined by tests known by those of skill in the art. The most commonly used measure for testing an oxidation of an edible fat or oil, or of a solid or liquid food product containing one or more edible fats or oils, is the Peroxide Value Test, which measures the concentration of the immediate products of oxidation (peroxides). However, these initial peroxide products are themselves degraded over time to various aldehydes, and these aldehyde secondary products are not detected by the Peroxide Value Test. A second known test, the Anisidine Test, may be used to detect the secondary products. Thus, the Peroxide Value Test measures the degree to which oxidation is taking place at the present moment, and the Anisidine Test measures the amount of historical oxidation over the life of a edible fat, oil or food product. These two measures may be combined to give a total oxidation (or TOTOX) value, which is calculated as:

TOTOX=Anisidine Value+(2×Peroxide Value).

Known organoleptic testing procedures can also be employed to test the taste and smell of edible fats and oil, and food products containing one or more edible fats and/or oils.

Edible oils include vegetable-based oils, such as soybean, corn, cottonseed, peanut, safflower, sunflower, canola and olive oil. In addition, edible oils include marine oils (including "fish oils"), such as those that are obtained from aquatic lifeforms, either directly or indirectly, particularly oily fish. Marine oils generally contain high levels of omega-3 fatty acids. Marine oils having a total omega-3 fatty acid content of greater than about 5 weight percent include those derived from menhaden oil, herring, capelin, anchovy, cod liver, salmon oil, sardine oil and mixtures thereof.

As those of skill in the art will appreciate, any one or more of a wide variety of edible fats and/or oils, and preferably those that contain omega-3 fatty acids, including DHA and/or EPA, may be employed in the compositions and methods of the present invention, including, but not limited to, the marine oils, fungal oils, plant oils and plant seed oils and combinations thereof. Edible fats and oils that are preferred for use in the methods of the invention are those that are rich in omega-3 fatty acids, such as DHA. The most preferred edible fats and oils for use in the methods of the invention are those containing at least about 5 percent by weight DHA, more preferably from about 10 percent by weight DHA to about 80 percent by weight DHA and most preferably about 20 percent by weight DHA to about 70 percent by weight DHA. DHA may be independently isolated and added to an omega-3 oil, or an omega-3 oil may be otherwise enriched in DHA content as is known in the art. Omega-3 oils additionally or alternatively may contain amounts of other omega-3 fatty acids, such as EPA.

The compositions of the invention may contain any number, and any combination, of edible oils, such as essential and non-essential fatty acids. In a preferred embodiment of the invention, only one edible oil is present in the compositions, and the edible oil comprises a beneficial fatty acid, preferably an omega-3 fatty acid, such as docosahexaenoic acid (DHA). In this embodiment, the DHA content is about 45 to 70 weight percent.

The DHA content of the compositions of the invention is preferably greater than about 5 weight percent of the total weight of the edible oils, and more preferably, greater than about 10 weight percent of the total weight of the edible oils, and still more preferably greater than about 25 weight percent of the total weight of the edible oils, such as a DHA content of about 50 weight percent of the total weight of the edible oils, or greater.

Vitamins and Minerals

A wide variety of oil- and/or water-soluble vitamins, minerals, and combinations thereof, may be used in the methods and compositions of the invention in varying quantities.

A primary aspect of the invention is that water-soluble vitamins and/or minerals will be present in the compositions. However, it is also contemplated that oil-soluble vitamins and minerals can be present in the compositions in addition, or alternatively, to water-soluble vitamins and/or minerals. The oil-soluble vitamins and/or minerals that may, optionally, be employed in the methods and compositions of the invention can be dissolved in one or more edible oils or be present in its own phase, or in mixtures thereof. Oil-soluble vitamins and/or minerals can, optionally, be added to one or more other edible oils or may be naturally occurring in one or more edible oils.

Water-soluble vitamins and minerals that can be used in the methods and compositions of the invention include, but are not limited to, Vitamin B1 (as Thiamin or Thiamine Mononitrate), Vitamin B2 (as Riboflavin), Vitamin B3 (as Niacin), Vitamin B6 (as Pyridoxine or Pyridoxine Hydrochloride), Vitamin B9/M (Folic Acid or Folate) or of reduced Folate, including but not limited to L-methylfolate, L-5-methyltetrahydrofolate, L-5-methyl-tetrahydrofolic acid, (6S)-tetrahydrofolic acid, (6S)-5-methyl-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and polyglutamyl derivatives of tetrahydrofolate acid, Vitamin B12 (cyanocobalamin, cobalamin, and reduced forms of cobalamin), Biotin, Vitamin C (Ascorbic Acid), Folacin, Niacinamide, Calcium (as Calcium Carbonate), Iron (as Ferrous Fumarate), Phosphorus, Pantothenic Acid (as Calcium Pantothenate), Iodine (as Potassium Iodide), Magnesium (as Magnesium Oxide), Zinc (as Zinc Oxide), Selenium (as Sodium Selenate), Copper (as Cupric Oxide), Manganese (as Manganese Sulfate), Chromium (as Chromium Chloride), Molybdenum (as Sodium Molybdate), Choline, Fluoride, Chloride, Potassium, Sodium, Biotin and various mixtures or other combinations thereof. L-methylfolate, or Metafolin™ (Merck-Eprova AG Schaffhausen, Switzerland), may also be used in place of or in addition to folic acid or folate. Recombinant Intrinsic Factor (rhIF) with bound Cobalamin (Cobento Biotech A/A, Science Park, Aarhus, Denmark) may be used in place of or in addition to vitamin B12.

Recombinant Intrinsic Factor is thought to be vital for the transport of vitamin B12 within the body. Intrinsic factor is normally present in the stomach. More specifically it is a glycoprotein secreted by parietal (humans) cells of the gastric mucosa. In humans, it has an important role in the absorption of vitamin B12 in the intestine.

Oil-soluble vitamins and minerals that may be employed in the methods and compositions of the invention include, but are not limited to, Vitamin A, Vitamin D, Vitamin E (as dl-Alpha Acetate or d-alpha Nat'l), Vitamin K and Tocopherol.

Compositions of the invention may be formulated using any pharmaceutically-acceptable forms of the vitamins and/or minerals described above, including their salts, which are known by those of skill in the art. For example, useful pharmaceutically-acceptable calcium compounds include any of the well-known calcium supplements, such as Calcium Carbonate, Calcium Sulfate, Calcium Oxide, Calcium Hydroxide, Calcium Apatite, Calcium Citrate-Malate, Bone Meal, Oyster Shell, Calcium Gluconate, Calcium Lactate, Calcium Phosphate, Calcium Levulinate, and the like. Pharmaceutically acceptable magnesium compounds include Magnesium Stearate, Magnesium Carbonate, Magnesium Oxide, Magnesium Hydroxide and Magnesium Sulfate. Pharmaceutically-acceptable iron compounds include any of the well-known Iron II (ferrous) or Iron III (ferric) supplements, such as Ferrous Sulfate, Ferric Chloride, Ferrous Gluconate, Ferrous Lactate, Ferrous Tartrate, Iron-Sugar-Carboxylate complexes, Ferrous Fumarate, Ferrous Succinate, Ferrous Glutamate, Ferrous Citrate, Ferrous Pyrophosphate, Ferrous Cholinisocitrate, Ferrous Carbonate, and the like. The vitamins and/or minerals that may be included in compositions of the invention may be microencapsulated in a coating of fat, microcrystalline cellulose or similar material in order to prevent their degradation under various conditions.

The vitamins and/or minerals that are preferred for use in the methods and compositions of the invention are those that have Daily Values (DVs), Reference Daily Intakes (RDIs) and/or Daily Reference Values (DRVs) described by the U.S. Food and Drug Administration (FDA) in its regulations or publications, such as the Code of Federal Regulations or Federal Register, Vol. 58, No. 3 (1993), for the following five categories of persons: (1) infants (persons not more than 12 months of age); (2) children under 4 years of age (persons 13 through 47 months of age); (3) adults and children that are 4 or more years of age; (4) pregnant women; and (5) lactating women. The most preferred vitamins and/or minerals for use in the methods and compositions of the invention are vitamin B6, vitamin B9 and vitamin B12.

One or more vitamins and/or minerals may be employed in the compositions of the invention in any quantity that is effective for providing, or enhancing, a nutritional, medical and/or other health benefit to a particular mammal, and that is safe for consumption by, or an administration to, the particular mammal, such as pregnant women, lactating women or women having childbearing potential that are attempting to become pregnant or their developing fetuses or babies (i.e., a quantity that would not cause harm to a woman consuming the composition, or to her developing fetus or breast-feeding baby). This quantity may vary depending upon the particular vitamins and/or minerals chosen for use, the age, size, weight and health condition of the mammal and like considerations, but generally ranges from about 2.5 to about 50 weight percent of the total weight of the compositions, and more preferably ranges from about 5 to about 25 weight percent, with about 10 weight percent being most preferred. The DVs described by the FDA, for example, in Federal Register, Vol. 58, No. 3 (1993) or in 21 CFR 101.9, for the different categories of human beings described above may be employed to determine such quantity for different mammals, and are set forth below.

| | | | DAILY VALUES | | | |
|---|---|---|---|---|---|---|
| | Units | Infants | Children Under 4 Years | Pregnant Women | Lactating Women | Persons that are 4 Years or Older |
| Vitamins | | | | | | |
| Vitamin A | IU | 1,500 | 2,500 | 8,000 | 8,000 | 5,000 |
| Vitamin C | mg | 35 | 40 | 60 | 60 | 60 |
| Vitamin D | IU | 400 | 400 | 400 | 400 | 400 |
| Vitamin E | IU | 5 | 10 | 30 | 30 | 30 |
| Vitamin K | µg | *** | *** | *** | *** | 80 |
| Vitamin B1 | mg | 0.5 | 0.7 | 2.5 | 2.5 | 1.5 |
| Vitamin B2 | mg | 0.6 | 0.8 | 2.0 | 2.0 | 1.7 |
| Vitamin B3 | mg | 8 | 9 | 20 | 20 | 20 |
| Vitamin B6 | mg | 0.4 | 0.7 | 2.5 | 2.5 | 2.0 |
| Vitamin B9 | mg | 1 | 0.2 | 0.8 | 0.8 | ** |
| Folate * | mg | *** | *** | *** | *** | 0.4 |
| Vitamin B12 | µg | 2 | 3 | 8 | 8 | 6 |
| Biotin | mg | 0.05 | 15 | 0.3 | 0.3 | 0.3 |
| Minerals | | | | | | |
| Pantothenic Acid | mg | 3 | 5 | 10 | 10 | 10 |
| Calcium | g | 0.6 | 0.8 | 1.3 | 1.3 | 1 |
| Phosphorus | g | 0.5 | 0.8 | 1.3 | 1.3 | 1 |
| Iodine | µg | 45 | 70 | 150 | 150 | 150 |
| Iron | mg | 15 | 10 | 18 | 18 | 18 |
| Magnesium | mg | 70 | 200 | 450 | 450 | 400 |
| Copper | mg | 0.6 | 1.0 | 2.0 | 2.0 | 2.0 |
| Zinc | mg | 5 | 8 | 15 | 15 | 15 |
| Selenium | µg | *** | *** | *** | *** | 70 |
| Manganese | mg | *** | *** | *** | *** | 2.0 |
| Chromium | µg | *** | *** | *** | *** | 120 |
| Molybdenum | µg | *** | *** | *** | *** | 75 |
| Chloride | mg | *** | *** | *** | *** | 3,400 |

* Folate is the anion form of folic acid (currently known as folacin or Vitamin B9 and formerly known as vitamin M). Vitamin B9 can be present as folic acid or one or more natural isomers of reduced Folate, including but not limited to L-methylfolate, L-5- methyltetrahydrofolate, L-5-methyl-tetrahydrofolic acid, (6S)-tetrahydrofolic acid, (6S)-5-methyl-tetrahydrofolic acid, 5-methyl-(6S)-tetrahydrofolic acid, 5-formyl-(6S)- tetrahydrofolic acid, 10-formyl-(6R)-tetrahydrofolic acid, 5,10-methylene-(6R)- tetrahydrofolic acid, 5,10-methenyl-(6R)-tetrahydrofolic acid, 5-formimino-(6S)- tetrahydrofolic acid, (6S)-5-methyltetrahydrofolic acid and polyglutamyl derivatives of tetrahydrofolate.
** Information not present in 21 CFR 101.9.
*** Information not present in Federal Register, Vol. 58, No. 3 (1993).

Additional information is available at the web site www.nal.usda.gov.

It is important that the quantity of each vitamin and/or mineral used in a method or composition of the invention be safe for consumption by, or an administration to, pregnant women, lactating women or women having childbearing potential that are attempting to become pregnant, and is safe for their developing fetuses or babies, or is safe for consumption by, or an administration to, other mammals that consume or use the composition. Larger quantities of certain vitamins and/or minerals may cause damage to a developing fetus or baby, or to other mammals. Those of skill in the art know the quantities of vitamins and minerals above the U.S. DVs for pregnant women, lactating women or women having childbearing potential that are attempting to become pregnant, or for other mammals, that would be harmful for the mammal consuming or using the composition, or for their developing fetuses or babies.

Set forth hereinbelow are the approximate preferred ranges of the daily quantities of the various vitamins and minerals that may generally be used in one composition of the invention (or divided between more than one composition of the invention for consumption or other administration during a one-day period) for mammals, including pregnant women, lactating women or women having childbearing potential that are attempting to become pregnant (from about one quantity to about another quantity), as well as more preferred ranges, and the most preferred quantities for pregnant and lactating women.

| | | PREFERRED RANGES | | | |
|---|---|---|---|---|---|
| | Units | More Preferred Range | Most Preferred Range | Most Preferred Quantity for Pregnant Women | Quantity for Lactating Women |
| Vitamin | | | | | |
| Vitamin A | IU | 0-9,000 | 1,500-8,000 | 8,000 | 8,000 |
| Vitamin C | mg | 0-1,000 | 35-500 | 60 | 60 |
| Vitamin D | IU | 0-800 | 200-400 | 400 | 400 |

-continued

PREFERRED RANGES

| | Units | More Preferred Range | Most Preferred Range | Most Preferred Quantity for Pregnant Women | Quantity for Lactating Women |
|---|---|---|---|---|---|
| Vitamin E | IU | 0-1,500 | 5-400 | 30 | 30 |
| Vitamin K | μg | 0-80 | 10-80 | 10 | 10 |
| Vitamin B1 | mg | 0-50 | 0.5-10 | 2.5 | 2.5 |
| Vitamin B2 | mg | 0-50 | 0.5-25 | 2.0 | 2.0 |
| Vitamin B3 | mg | 0-60 | 5-40 | 20 | 20 |
| Vitamin B6 | mg | 0-50 | 0.4-30 | 2.5 | 2.5 |
| Vitamin B9 | mg | 0-2 | 0.2-1.0 | 0.8 | 0.8 |
| Vitamin B12 | μg | 0-1,000 | 2.0-18 | 8 | 8 |
| Biotin | mg | 0-15 | 0.05-15 | 0.3 | 0.3 |
| Mineral | | | | | |
| Pantothenic Acid | mg | 0-20 | 3-15 | 10 | 10 |
| Calcium | g | 0-3 | 0.2-2.0 | 1.3 | 1.3 |
| Phosphorus | g | 0-2 | 0.1-1.5 | 1.3 | 1.3 |
| Iodine | μg | 0-200 | 45-150 | 150 | 150 |
| Iron | mg | 0-100 | 5-50 | 18 | 18 |
| Magnesium | mg | 0-600 | 50-500 | 450 | 450 |
| Copper | mg | 0-2 | 0.1-2 | 2 | 2 |
| Zinc | mg | 0-30 | 1-25 | 15 | 15 |
| Selenium | μg | 0-400 | 60-100 | 60 | 70 |
| Manganese | mg | 0-5 | 0.1-5 | 5 | 5 |
| Chromium | μg | 0-150 | 0.1-120 | 25 | 25 |
| Molybdenum | μg | 0-75 | 20-75 | 25 | 25 |
| Chloride | mg | 0-3,400 | 2,000-3,400 | Not Established | Not Established |
| Choline | mg | 0-1,000 | 300-600 | 450 | 550 |
| Fluoride | mg | 0-5 | 1-4 | Not Established | Not Established |
| Potassium | mg | 0-80 | 10-80 | Not Established | Not Established |
| Sodium | mg | 0-2,400 | 10-1,000 | Not Established | Not Established |

One composition of the invention may contain one or more of the above (or other) vitamins and/or minerals in their preferred or other quantity range (or in their more preferred range, or in the most preferred quantity for pregnant women, lactating women or women having childbearing potential that are attempting to become pregnant, or for other mammals). Alternatively, one composition may include each of these vitamins and/or minerals in one half, one third, one forth, one fifth, one sixth, and so forth, of these quantities. Varying combinations of a wide variety of vitamins and/or minerals may also be employed.

Vitamins and minerals are commercially available from sources known by those of skill in the art, such as Hoffmann-LaRoche Inc. (Nutley, N.J.), or may be derived from various food products, such as those described hereinbelow, using techniques known by those of skill in the art. For example, vitamin A can be derived from dark green, dark yellow and orange vegetables, such as carrots and sweet potatoes and colored fruits, such as peaches, oranges, and apple. Vitamin B1 may be derived from wheat germ, nutritional yeast, cooked beans and peas, collard greens, raisins, oranges, nuts, and whole grains. Vitamin B2 may be derived from dark green leafy vegetables, avocado, wheat germ, and whole grains. Vitamin B3 (Niacin) may be derived from cooked dried beans, and peas, nuts, whole wheat and grains, potato, and nutritional yeast. Vitamin B6 (Pyridoxine) may be derived from cooked dried beans and peas, nutritional yeast, wheat germ, nuts, bananas, avocados, leafy greens, cabbage, cauliflower, potatoes, whole grains, and dried fruit. Vitamin B7 (Biotin) may be derived from oatmeal, nutritional yeast, legumes, soybeans, mushrooms, bananas, nuts, and whole grains. Vitamin B12 (cyanocobalamim cobalamin, and/or reduced forms of cobalamin) may be derived from nutritional yeast, fortified foods and beverages such as cereals, soymilk and orange juice. Folate (Folic Acid) may be derived from dark green-leafy vegetables, nutritional yeast, beans, avocados, wheat germ, various fruits like banana, orange, and whole grains. Pantothenic Acid may be, derived from legumes, soybeans, avocados, mushrooms, green vegetables, bananas, oranges; whole grains and wheat germ. Vitamin C (Ascorbic Acid) may be derived from fresh fruits and vegetables, green pepper, broccoli, citrus fruits, tomatoes, guava and strawberries. Vitamin D may be derived from sunlight, fortified foods and beverages. Vitamin E (Tocopherol) may be derived from vegetable oils, seeds, nuts, wheat germ, spinach, peaches, avocados, broccoli, dried prunes and whole wheat. Vitamin K may be derived from green or leafy vegetables, broccoli, turnip greens, cabbage, cauliflowers and avocados.

Although a wide variety of vitamins and/or minerals may be employed in the methods and compositions of the invention, compositions of the invention preferably include vitamin B6, vitamin B9 and/or vitamin B12. Vitamin B6 (as Pyridoxine or Pyridoxine Hydrochloride) may, for example, be present in the composition in an amount that preferably ensures the presence of from at least about 1 mg to about 50 mg per unit dosage form. Vitamin B9/M (Folic Acid) may, for example, be present in the composition in an amount that preferably ensures the presence of from at least about 100 μg to about 1000 μg per unit dosage form. Vitamin B12 (cyanocobalamin, cobalamin, and/or reduced forms of cobalamin) may, for example, be present in an amount that preferably ensures the presence of from at least 200 μg to about 2000 μg per units dosage form. A variety of vitamins and minerals, including vitamin B6, vitamin B9 and vitamin B12, are commercially available from sources known by those of skill in the art, such as Hoffmann-LaRoche Inc. (Nutley, N.J.). Preferably, solid-state vitamins are provided as finely divided powders, such as amorphous powders or very finely milled crystalline powders. This generally ensures content uniformity and inhibits agglomeration of the vitamins and/or minerals in the compositions of the invention.

Optional Components

In addition to vitamins, minerals and/or edible oils, the compositions of the invention may, optionally, contain one or more additional pharmaceutically-acceptable and edible compounds, drugs, substances, ingredients and/or materials, in an amount that is safe for consumption by, or other administration to, mammals, which may readily be determined by those of skill in the art.

Wetting agents, emulsifiers, lubricants, coloring agents, release agents, coating agents, sweetening agents, flavoring agents, preservatives, suspending agents, antioxidant agents, additional carriers and other suitable agents may also, optionally, be included within the compositions of the invention. However, such materials should be compatible with other ingredients that are present in the compositions, and not harmful to mammals.

Antioxidant Agents

In addition to those described elsewhere herein, edible and pharmaceutically-acceptable antioxidant agents that may, optionally, be included in the methods and compositions of the invention include, for example: (a) water soluble antioxidants, such as ascorbic acid, cysteine hydrochloride, sodium bisulfate, sodium metabisulfite, sodium sulfite and the like; (b) oil-soluble antioxidants, such as ascorbyl palmitate, butylated hydroxytoluene (BHT), lecithin, propyl gallate, alpha-tocopherol and the like; and (c) metal chelating agents, such as citric acid, ethylenediamine tetraacetic acid (EDTA), sorbitol, tartaric acid, phosphoric acid and the like. A wide variety of edible antioxidant agents are commercially available from sources known by those of skill in the art.

The amount of one or more antioxidant agents, or combination thereof, that may be employed in the methods and compositions of the invention is a combined amount that is effective for preventing or reducing an oxidation, degradation and/or other decomposition that would otherwise occur to components or ingredients of the compositions of the invention, such as water-soluble vitamins and/or minerals and/or edible oils, and, optionally, for producing or enhancing one or more other beneficial effects, and that is safe for consumption or use by mammals. Such an amount may vary depending upon a variety of factors, such as the type of mammal consuming or using the compositions, the size, weight, sex and medical status of the mammal, the type of ingredients employed in the compositions, the amounts thereof, and like factors, and may readily be determined by those of skill in the art. The amount (combined) of one or more antioxidants that are preferably employed in the compositions and methods of the invention ranges from about 0 to about 90 weight percent of the total weight of the compositions when present in, or as, an edible oil, such as vitamin E, and from about 0 to about 2 weight percent when not present in, or as, an edible oil, and most preferably is about 0.046 weight percent.

Suspending Agents

One or more edible or pharmaceutically-acceptable suspending agents are preferably included in the compositions and methods of the invention and include phytosterols, phytosterol esters, plant stanols and/or plant stanol esters. Optionally, they may additionally include one or more other edible suspending agents, such as lecithin, yellow beeswax, sunflower oil, ethoxylated isostearyl alcohols, polyoxyethylene sorbitol, sorbitan esters and microcrystalline cellulose, and combinations thereof.

Phytosterols, phytosterol esters, plant stanols and plant stanol esters, as well as a wide variety of other suitable suspending agents for use in the compositions and methods of the invention, are commercially available from sources known by those of skill in the art.

Coronary heart disease (one of the most common and serious forms of cardiovascular disease, which includes diseases of the heart muscle and supporting blood vessels) is a major public health concern in the United States. It accounts for more deaths than any other disease or group of diseases. High blood total and LDL cholesterol are major modifiable risk factors in the development of coronary heart disease. Scientific evidence demonstrates that diets that include plant sterol/stanol esters may reduce a risk of coronary heart disease. The scientific evidence establishes that including plant sterol/stanol esters in the diet helps to lower blood total and LDL cholesterol levels. Daily dietary intake levels of plant sterol and stanol esters that have been associated with reduced risk are:

(1) 1.3 g or more per day of plant sterol esters; or
(2) 3.4 g or more per day of plant stanol esters.

CardioAid™-M phytosterols are in a form of an off-white, ultra-fine powder, which is solid at room temperature and has a melting point of from about 275° F. to about 293° F., are derived from vegetable oils and have the typical chemical and physical properties set forth below.

| Typical Chemical and Physical Properties | |
| --- | --- |
| Phytosterol | Quantity or Quality |
| Total phytosterols | Minimum 95.0 |
| Beta-sitosterol | 40-58* |
| Campesterol | 20-30* |
| Stigmasterol | 14-22* |
| Brassicasterol | 0-6* |
| Sitostanol | 0-5* |
| Appearance | Granular Solid |
| Odor | Slight |
| Tocopherols | 0-15 mg/g |
| Melting Point | 135-145° C. |
| Heavy Metals | Maximum 10 ppm |
| Solubility in Water | Insoluble |
| Particle Size Distribution | Less than 10 Microns Minimum 90.0 |

*As percent of total sterols.

It is recommended by Archer Daniels Midland Company (Decatur, Ill.) that CardioAid™-M phytosterols be stored in closed packaging under dry conditions.

CardioAid™-S phytosterol esters are in a form of a creamy white to pale yellow paste, which is a semi-solid at room temperature, are derived by esterifying sterols with canola oil fatty acids and have the typical chemical and physical properties set forth below.

| Typical Chemical and Physical Properties | |
| --- | --- |
| Phytosterol | Quantity or Quality |
| Total phytosterols | Minimum 56.0 |
| Total phytosterol esters | Minimum 90.0 |
| Free Sterols | Maximum 5.0 |
| Beta-sitosterol | 40-58* |
| Stigmasterol | 14-22* |
| Brassicasterol | 0-6* |
| Sitostanol | 0-5* |
| Campesterol | 20-30* |
| Cholesterol | Maximum 1.0* |
| Appearance | Creamy White to Pale Yellow Solid |

-continued

Typical Chemical and Physical Properties

| Phytosterol | Quantity or Quality |
|---|---|
| Flavor and Odor | Bland |
| Melting Point | 25-30° C. |
| Acid Value | Maximum 1.0 mg KOH/g |
| Peroxide Value | Maximum 5.0 meq/kg |
| Moisture | Maximum 0.1% |

*As percent of total sterols.

The amount of one or more edible suspending agents, or combination thereof, that may be employed in the methods and compositions of the invention is a combined amount that is safe for consumption or use by mammals, that has an ability to fit within a hollow oral dosage form, or hollow suppository form, that is effective for initiating, enhancing and/or maintaining a suspension of one or more soft-solid, semi-solid, solid or other components in a semi-liquid, liquid or other vehicle, for example, one or more solid-state vitamins and/or minerals in one or more edible oils and, preferably, that is also effective for providing or enhancing one or more nutritional, medical and/or health benefits to a mammal, such as providing, enhancing or maintaining a normal or healthy cholesterol level, or preventing or reducing a risk of cardiovascular disease, in a mammal. Such an amount may vary depending upon a variety of factors, such as the type of mammal consuming or using the compositions, the size, weight, sex and medical status of the mammal, the type of ingredients employed in the compositions, the amounts thereof, and like factors, and may readily be determined by those of skill in the art. Such an amount (combined) will preferably range from about 1 to about 60 weight percent of the total weight of the compositions, and will more preferably be about 32.16 weight percent.

It is preferred that at least about 800 mg per day of a combined amount of phytosterols, plant stanols and/or esters thereof are administered to a mammal. Such an amount may be administered to a mammal in one or more unit dosage forms of a composition of the invention in a wide variety of manners. For example, if one unit dosage form of a composition of the invention, such as a soft-gel capsule, contains a combined amount of about 200 mg of phytosterols, plant stanols and/or esters thereof, four of these unit dosage forms may be administered to a mammal per day to provide 800 mg per day of the phytosterols, plant stanols and/or esters thereof. As another example, if one unit dosage form of a composition of the invention contains a combined amount of about 100 mg of phytosterols, plant stanols and/or esters thereof, eight of these unit dosage forms may be administered to a mammal per day to provide 800 mg per day of the phytosterols, plant stanols and/or esters thereof.

Suspending agents, such as phytosterols, phytosterol esters, plant stanols, plant stanol esters, yellow beeswax and/or lecithin, when added to one or more edible oils (or other ingredients) that are employed in the compositions of the invention, or are otherwise employed in these compositions, can prevent, or reduce the likelihood of, vitamins and/or minerals (or other ingredients) from settling out from the compositions when the compositions are in the form of a suspension during a period of time that the compositions may have to wait in a hopper (or similar device) of an apparatus that is employed to fill one or more hollow oral dosage forms or hollow suppository forms, such as hollow soft-gel capsules, with the suspension, or to otherwise produce one or more hollow oral dosage forms or hollow suppository forms.

The formulation and manufacture of liquid capsule (or other) products with a powder (or other sized-reduced solid) that is a non-soluble powder in the liquid component employed in the capsule typically requires an addition of one or more suspending agents in the liquid phase. The suspending agents have the effects of: (a) increasing the viscosity of the liquid phase; and (b) slowing the Stokes settling velocity of the powder during compounding and encapsulation (or other filling) processes. The result of achieving the most preferable (correct) viscosity in the formulation is a homogeneous distribution of the powder ingredient in each capsule during the encapsulation (or other filling) processes. Suspending agents that are typically employed are waxes, which are solids at room temperature. The liquid inside the capsule are a therapeutic or nutritive entity or a solution of a therapeutic or nutritive entity. These entities are typically heat sensitive and, therefore, cannot be heated to the melting point of the wax in order to incorporate them together. Therefore, the wax is preferably heated and melted separately, and added to a vegetable oil (or other edible oil), which is a liquid at room temperature. The resulting combination has a lower melting point and, therefore, can be added to the liquid nutritive entity or a solution of a therapeutic or nutritive entity while minimizing the heat effects, and developing the necessary viscosity for the addition of the insoluble powder phase to the capsule fill. The use of the wax and vegetable oil combination as a suspending agent takes up from about 15% to about 40% of the weight of the capsule fill, thus limiting the active ingredients that can be formulated per capsule.

In addition to phytosterols, phytosterol esters, plant stanols and/or plant stanol esters, preferred suspending agents for use in the compositions and methods of the invention include lecithin, yellow beeswax and sunflower oil. Because of the significant nutritional, medical and/or health benefits that they can provide in connection with providing, enhancing or maintaining a normal or healthy cholesterol level, or preventing or reducing a risk of cardiovascular disease, in a mammal, as is described herein, which is in addition to, and can be simultaneously with, their ability to function as suspending agents, and because of their ability to fit within unit oral dosage forms or hollow suppository forms of the compositions of the invention along with active ingredients present therein, phytosterols, phytosterol esters, plant stanols and plant stanol esters, and combinations thereof, are included in the compositions and methods of the invention.

CardioAid™-M phytosterols independently, CardioAid™-S phytosterol esters independently, or a combination of the two, may be employed in the compositions and methods of the invention. The M is a micronized form, and is the same as the granular form designated without the M. Either form can be employed. However, it is preferred that a combination of CardioAid™-M phytosterols and CardioAid™-S phytosterol esters be employed in the compositions and methods of the invention. When such a combination is employed, the ratio of these two suspending agents may vary from about 0% CardioAid™-M phytosterols and about 100% CardioAid™-S phytosterol esters to about 100% CardioAid™-M phytosterols and about 0% CardioAid™-S phytosterol esters. The desired ratio of these two suspending agents may depend upon the viscosity that is determined to be necessary to maintain one or more solids in suspension, which may readily be determined by those of skill in the art.

Emulsifiers

In addition to those described elsewhere herein, edible emulsifiers that may, optionally, be included in the methods and compositions of the invention include, for example, egg yolk, egg lecithin, soy lecithin and mono- and di-glycerides.

A wide variety of edible emulsifiers are commercially available from sources known by those of skill in the art.

The amount of one or more emulsifiers, or combination thereof, that may be employed in the methods and compositions of the invention is a combined amount that is effective for causing, or aiding in, a formation of an emulsion, for example, a water-in-oil emulsion in which one or more edible oils, or a combination thereof, is the continuous phase and a solution of one or more water-soluble vitamins and/or minerals, or a combination thereof, is the disperse phase, and, optionally, producing or enhancing one or more other beneficial effects, and that is safe for consumption or use by mammals. Such an amount may vary depending upon a variety of factors, such as the type of mammal consuming or using the compositions, the size, weight, sex and medical status of the mammal, the type of ingredients employed in the compositions, the amounts thereof, and like factors, and may readily be determined by those of skill in the art. Such an amount (combined) will preferably range from about 0 to about 30 weight percent of the total weight of the compositions, and will preferably range from about 0.1 to about 15 weight percent, and will more preferably be about 0.912 weight percent.

Diluents

In addition to those described elsewhere herein, edible diluents that may, optionally, be included in the methods and compositions of the invention include, for example, complex polysaccharides, carbohydrates, smaller sugars (dextrose, sucrose and the like), dicalcium phosphate, tricalcium phosphate, maltodextrin and water. Anhydrous diluents are preferred for use in the compositions of the invention with one or more water-soluble vitamins and/or minerals. A wide variety of edible diluents and anhydrous diluents are commercially available from sources known by those of skill in the art.

The amount of one or more diluents, or combination thereof, that may be employed in the methods and compositions of the invention is a combined amount that is effective for causing or enhancing a dilution, decrease in potency, thinning, weakening and/or a physical separation of one or more substances, agents or compositions, such as one or more water-soluble vitamins and/or minerals, and, optionally, producing or enhancing some other beneficial effect, and that is safe for consumption or use by mammals. Such an amount may vary depending upon a variety of factors, such as the type of mammal consuming or using the compositions, the size, weight, sex and medical status of the mammal, the type of ingredients employed in the compositions, the amounts thereof, and like factors, and may readily be determined by those of skill in the art. The amount (combined) of one or more diluents that may be employed in the compositions and methods of the invention generally ranges from about 0 to about 90 weight percent of the total weight of the compositions, and preferably is about 0.912 weight percent. In some instances, one or more diluents may, for example, be present in a vitamin and mineral powder pre-mix.

Water

The amount of water, or water-containing composition, that may optionally be employed for forming an aqueous solution with one or more water-soluble vitamins and/or minerals generally ranges from the smallest quantity of water that may permit the formation of such an aqueous solution to the largest amount of water that may fit within an oral dosage form of the composition of the invention. Such an amount of water may vary depending upon a variety of factors, such as the size of the oral or suppository dosage form of the composition, the number of components that are present in the composition, the quantities of the components that are present in the composition, and like factors, and may readily be determined by those of skill in the art. The amount of water that may be employed in a formation of an aqueous solution preferably ranges from just above 0 to about 30 weight percent, and most preferably is about 10 weight percent.

The more preferred compositions of the invention do not employ water or an aqueous solution (i.e. they include suspensions, rather than emulsions). Further, when water is employed in the compositions of the invention, it is preferable that the inside of the one or more hollow oral dosage forms or hollow suppository forms employed are coated with one or more moisture barriers, or a combination thereof. A wide variety of such moisture barriers are known by those of skill in the art.

The temperature of the water employed to produce an aqueous solution of the water-soluble vitamins and/or minerals generally should be no higher than about 130° F. In addition, the water used should be in a liquid state (i.e., not frozen). Thus, the temperature of the water employed in the process of the invention should generally range from about ambient temperature to about 130° F., with ambient temperature being most preferred.

Unit Dosage Forms of Compositions

A unit dosage form of the compositions of the invention will typically comprise a soft or hard gel capsule, gelcap, caplet or other oral dosage form or suppository form containing a combined amount of from about 0.25 ml to about 5 ml of one or more edible oils, an effective amount of one or more vitamins and/or minerals, which are preferably water soluble, as is described herein, and an effective amount of one or more suspending agents. The unit dosage may, optionally, also contain one or more antioxidant agents, emulsification agents, diluents and/or other optional ingredients or components as practically needed, or as desired, in quantities that are beneficial for a mammal, which quantities may readily be determined by those of ordinary skill in the art.

A preferred unit dose of a composition of the invention includes a combined amount of about 700 mg of oils, of which 500 mg is preferably omega-3 oil, including 350 mg of DHA and 35 mg EPA. Each unit dose of the one or more edible composition also preferably comprises about 12.5 mg of vitamin B6, about 500 μg of vitamin B12, about 1000 mg of folic acid (vitamin B9), about 105.3 mg of CardioAid™-M phytosterols, about 178.6 mg of CardioAid™-S phytosterol esters, as well as a trace amount of tocopherol (an antioxidant), as is known in the art. If CardioAid™-M phytosterols and CardioAid™-S phytosterol esters are not present in a unit dose of a composition of the invention, yellow beeswax and/or lecithin are preferably included in the compositions of the invention, and are preferably added to the one or more edible oils to act as suspending agents so that the vitamins and/or minerals do not settle during their wait in a hopper for encapsulation. In this unit dose, it is preferred to administer two gel capsules (or other unit dosage form) each day (either two gel capsules together once per day or spaced apart in any desire time interval, such as 1, 2, 3, 4, 5, 6, 7 or 8 hours during the day).

The size of a unit dosage form of a composition of the present invention preferably ranges from the smallest size that has an ability to contain desired quantities of desired components to the largest size that can be consumed or used (inserted into a body orifice) by a mammal without a significant risk of choking, gagging, vomiting and/or experiencing pain, discomfort or one or more other adverse effects. More preferably, a unit dosage form of a composition of the invention will have a size that has an ability to contain desired quantities of desired components, and that may be conveniently and readily swallowed or used by a mammal. The size of a unit dosage form of a composition of the present may vary depending upon a variety of factors, such as the type of the mammal that is to consume or use the composition, the number of components that are present in the composition, the quantities of the components that are present in the composition, and like factors, and may readily be determined by those of skill in the art.

Preferably, a unit dosage form of a composition of the invention for an oral administration is a hard or soft capsule that ranges in size from about a #10 oval to about a #24 oblong, and that contains a contents ranging from about 400 mg to about 1,600 mg. Most preferably, such a unit dosage form has a size of about a #20 oblong, and holds about 1,100 mg of contents.

A composition of the invention in a form of a rectal suppository may, for example, be about 5 mm in diameter and from about 1 to about 1.5 inches in length.

Method of Production

The compositions of the invention may be produced by admixing or otherwise combining the above-described ingredients to form a suspension, emulsion or other desired form, of the one or more vitamins and/or minerals, the one or more edible oils, the one or more suspending agents and, optionally, one or more other ingredients using, for example, methods, conditions and equipment known by those of skill in the art, followed by an injection or other insertion of the resulting mixture (suspension, emulsion or the like) into hollow oral dosage forms or hollow suppository forms, such as empty gelatin capsules, gelcaps or caplets (shells).

For example, the compositions of the invention may be produced using a method comprising the following steps (in any convenient or possible order):

(a) providing one or more vitamins or minerals, or a combination thereof, in a combined amount that is effective for providing or enhancing one or more nutritional, medical or other health benefits, or a combination thereof, to a mammal, wherein the one or more vitamins or minerals, or combination thereof, are water-soluble and oil-insoluble, are initially in a solid-state form, are exogenous to one or more edible oils that may be included in the composition and are in a form that is capable of being mixed with one or more edible oils;

(b) providing one or more edible oils, or a combination thereof, in a combined amount that is effective for permitting at least some of the one or more vitamins or minerals, or combination thereof, to be mixed therewith, or at least temporarily suspended therein, or for forming a continuous or disperse phase of a dispersion, wherein the one or more edible oils, or combination thereof, includes one or more substances that can provide a nutritional, medical or other health benefit, or a combination thereof, to a mammal;

(c) providing one or more edible suspending agents, or a combination thereof, in a combined amount that is effective for initiating, enhancing or maintaining a suspension of the one or more vitamins or minerals, or combination thereof, in the one or more edible oils, or combination thereof, and/or for providing a nutritional, medical or other health benefit, or a combination thereof, to a mammal, wherein the one or more edible suspending agents, or a combination thereof, include phytosterols, phytosterol esters, plant stanols or plant stanol esters, or a combination thereof;

(d) optionally, providing one or more edible antioxidant agents, or a combination thereof, in a combined amount that is effective for preventing or reducing an oxidation, degradation or other decomposition of the one or more vitamins or minerals, or combination thereof the one or more edible oils, or combination thereof, or of one or more other components that are present in the composition, or any combination thereof;

(e) optionally, providing one or more edible diluents, or a combination thereof, in a combined amount that is effective for diluting, rendering less potent, thinning, weakening or facilitating a physical separation of one or more components that are included in the composition;

(f) optionally, providing one or more edible emulsifiers, or a combination thereof, in a combined amount that is effective for causing or enhancing a formation of an emulsion;

(g) optionally, providing one or more edible surfactants, or a combination thereof, in a combined amount that is effective for reducing a surface tension when dissolved or otherwise included in an aqueous liquid or reducing an interfacial tension between two liquids, or between a liquid and a solid;

(h) providing one or more edible hollow oral dosage forms or hollow suppository forms;

(i) optionally, mixing the one or more vitamins or minerals, or combination thereof, for a period of time and under conditions that are effective for producing a substantially uniform mixture of the one or more vitamins or minerals, or combination thereof;

(j) optionally, mixing the one or more vitamins or minerals, or combination thereof, with an amount of an aqueous liquid, and for a period of time and under conditions, that are effective for forming an aqueous solution;

(k) optionally, mixing the one or more edible oils, or combination thereof, for a period of time and under conditions that are effective for producing a uniform mixture of the one or more edible oils, or combination thereof;

(l) optionally, mixing the one or more edible suspending agents, or combination thereof, for a period of time and under conditions that are effective for producing a uniform mixture of the one or more edible suspending agents;

(m) optionally, combining the antioxidant agents, diluents, emulsifiers, surfactants or other optional ingredients, or combination thereof, with the one or more vitamins or minerals or the one or more edible oils, or with any combination thereof;

(n) combining the one or more vitamins or minerals, or combination thereof, with the one or more edible oils, or combination thereof, and the one or more edible suspending agents, or combination thereof, for a period of time and under conditions that are effective for:

(i) producing a suspension of at least some of the one or more vitamins or minerals, or particles or combination thereof, in the one or more edible oils, or combination thereof, wherein the one or more vitamins or minerals, or particles or combination thereof, and the one or more edible oils, or combination thereof, remain in suspension for at least a period of time that is sufficient to enable the one or more edible hollow dosage forms or hollow suppository forms to be partially or fully filled with the suspension; or (ii) producing a dispersion; and (o) inserting the suspension or dispersion into the one or more edible hollow oral dosage forms or hollow suppository forms, or forming a solid suppository therewith, in an amount that is effective for partially or fully filling the one or more edible hollow oral dosage forms or hollow suppository forms so as to form one or more unit dosage forms, wherein substantially the same quantity of each of the components that are present in the composition becomes present in each of the one or more unit dosage forms.

General methods and equipment that may be employed to perform each of the above steps are known by those of skill in the art. With respect to methods, equipment and agents employed in the preparation of emulsions, see for example, Simon Benita, "Submicron Emulsions in Drug Targeting and Delivery" (CRC Press, ISBN 9057023490, 1999), Clyde Stauffer, "Emulsifiers" (AACC International, ISBN 1-891127-00-04, 1998) and R. L. Earle and M. D. Earle, "Unit Operations in Food Processing" (NZIFST, Inc, 1983). With respect to methods, equipment and agents employed in the preparation of suspensions, see for example, J. S. Van Duijneveldt, "Encyclopedia of Chemical Physics and Physical Chemistry" (ISBN 0750303131, 2001) and Arnold Grubenm, "Formulation Technology: Emulsions, Suspensions and Solid Forms" (ISBN 3527302018).

A wide variety of filling and production machines that may be employed to partially or fully fill, or produce, capsules, other oral dosage forms or suppositories, and related equipment, are commercially available, for example, from sources listed in the Packaging Digest web site www packagingdigest.com, and at the web sites www.sarong.it/inglese/saas9.asp and www.1pmie.net/txt/Injection.htm. Additionally, methods for producing soft, hard and other capsules are described, for example, in U.S. Pat. Nos. 6,077,531, 3,427, 378, 4,016,254, 4,931,284, 4,987,031, 5,916,591, 5,925,381, 6,190,694, 6,551,615 B1, 6,413,463, 6,506,406 and 6,280, 767, in published U.S. Patent Applications Nos. US 2003/0021839 A1 and US 2003/0012797 A1 and in EP 1 163 901 A1. Solid suppositories may be produced using conventional methods and equipment.

Because, in some cases, some or all of the one or more vitamins and/or minerals employed in a composition of the invention may settle out from a suspension, emulsion or other form after a short period of time, the composition is preferably mixed or agitated one or more times, using known or other mixing, circulating, looping, stirring, agitation or shaking techniques, prior to injecting or otherwise inserting the composition into the hollow gelatin capsules (or other hollow oral dosage forms or hollow suppository forms). Such mixing, which should permit the composition to be uniformly inserted into two or more of the hollow oral dosage forms or hollow suppository forms, is preferably performed immediately prior to such insertion. However, the mixing can be performed at any time prior to such insertion that is effective for permitting the composition to be uniformly inserted into two or more of the hollow oral dosage forms or hollow suppository forms. This period of time, and the number of times that the composition should be mixed, may vary depending upon a wide variety of circumstances, such as the number of hollow oral dosage forms or hollow suppository forms that are being filled and the number, and quantities of, water-soluble or other vitamins and/or minerals and edible oils that are present in the composition, or whether suspending agents are utilized, and may readily be determined by those of skill in the art. Once the composition is inserted into, or encapsulated within, the hollow oral dosage forms or hollow suppository forms, it generally is no longer necessary to have the one or more water-soluble or other vitamins and/or minerals suspended, or otherwise distributed, within the one or more edible oils. A mammal that consumes or uses one or more filled gelatin capsules (or other oral dosage forms or hollow suppository forms) should receive approximately the same amount of water-soluble or other vitamins and/or minerals and edible oils (and other components) once the capsules, gelcaps, caplets or other oral dosage forms or hollow suppository forms dissolve, disintegrate or otherwise decompose, whether the composition is present in the form of a suspension, an emulsion or some other form, or in the form of water-soluble vitamins and/or minerals that have settled out from a suspension.

EXAMPLES

The following examples describe and illustrate compositions within the present invention, and methods for preparing such compositions, and are intended to be merely illustrative of the present invention, and not limiting thereof in either scope or spirit. Those of skill in the art will readily understand that variations of certain of the conditions and/or steps employed in the procedures described in the examples can be used to prepare these compositions.

Example 1

Capsules Containing Suspending Agents Comprising Sunflower Oil and Yellow Beeswax A mixture containing edible oils, including fish oil and sunflower oil, and solid-state particles of vitamin B6, B9 and B12, with each of the three B vitamins present in the form of a finely divided uniformly mixed powder is prepared as follows. Sunflower oil is mixed with yellow beeswax and heated to 145° F. causing the beeswax to melt. The mixture of sunflower oil and melted beeswax is then transferred to a larger vessel, where it is blended with lecithin. The beeswax mixture and lecithin are present in quantities sufficient to enhance the ability of the solid-state vitamins to remain at least temporarily in suspension. This mixture is then blended into fish oil, including amounts of DHA and EPA such that the final mixture includes DHA in an amount which is about 50 weight percent of the total weight of edible oils and EPA in an amount which is about 5 weight percent of the total weight of the edible oils. The mixture is allowed to come to approximately 80° F. Thereafter, the solid-state particles of the vitamins are added to the blend of the edible oils and the beeswax and lecithin. This mixture is thoroughly blended, at approximately 70° F., so as to assure content uniformity, and added to a hopper of a conventional soft-gel capsule, gelcap, or caplet manufacturing device. Soft-gel ribbons are combined around unit doses of the mixture to produce a semi-finished capsule, gelcap, or caplet. Optionally, ascorbyl palmitate may be added at the time the vitamin particles are added. It is also anticipated that the vitamins may or may not be coated at the time they are added to the mixture. The vitamins may, for example, be coated with an edible oil, such as vegetable oil, prior to mixing. Furthermore, tocopherols or vitamin E may, optionally, be added to the fish oil, and vitamin B12 may be triturated with anhydrous ascorbic acid, which is used as a diluent for the vitamin mixture.

To minimize an oxidation of the fish oil and other edible oils that may be used in the compositions of the invention, nitrogen may be used. For example, nitrogen may be used to displace atmospheric oxygen in the head space within a container holding the oil. Also, a "nitrogen blanket" may be used, as is known to those of skill in the art, to further minimize an oxidation of the oil during the mixing stages, and during other steps in which it is otherwise being handled. Alternatively, the mixing could take place within a vacuum to minimize an oxidation of the oil.

In its raw form, gelatin is a thick, syrupy liquid. By the process of cooling and manipulating, it is turned into a ribbon and laid out on a sheet. This sheet is fed around the outer surfaces of two dyes and rolled together. Two dyes in the shape of a soft gel rotate and come together. As they come together, the fill material that is present in a hopper is injected. Heat and pressure form the capsule, gelcap, caplet or other oral dosage form into a hermetically sealed mold. The soft gels are very delicate when they come off the machine. A conventional drying process hardens them into the finished product.

Prior to packaging, the gel capsules, gelcaps, or caplets (or other unit dosage form) may, optionally, be irradiated in order to kill microorganisms that may have become present therein or thereon during production or otherwise. Such irradiation should be performed at a level, and for a period of time, that does not diminish or destroy the effectiveness of any of the edible oils or vitamins and/or minerals contained therein.

The resulting gelatin capsules, gelcaps, caplets or other unit dosage forms may then be packaged in any manner known by those of skill in the art for packaging vitamins, minerals, oils, oral dosage forms, pharmaceutical products or similar items.

Gel caps may be produced using known methods from a variety of different types of gelatin, for example, type A gelatin, type B gelatin or gelatin that is Kosher. Different types of gelatin can be obtained from commercial sources that are known by those of skill in the art, such as Post Apple Scientific (North East, Pa.), or may be produced using known methods.

Gelatin is a protein that can be extracted using standard extraction techniques from a product that results after a partial hydrolysis of collagenous raw material, which may be obtained from the skin, white connective tissue or bones of animals. For example, collagen, the precursor of gelatin, can be pretreated for about 10-30 hours with a 1-5% mineral acid for type A gelatin production or for about 35-90 days in a liming process with a lime slurry for type B gelatin production. Type A gelatin exhibits the isoionic point at pH 7.0-9.5, whereas type B gelatin, due to domination in the liming process, exhibits the isoionic point at 4.8-5.2. Type A gelatin can be manufactured from frozen or fresh edible-grade pigskins or from bone ossein. Most of type B gelatin comes from bones. While most edible gelatin is of type A, type B gelatin is also used. Pieces of bone generally are pretreated with either mineral acid (for type A gelatin) or lime (for type B gelatin) in the manner described above, and then demineralized in 4-7% hydrochloric acid for a period of about 7-14 days. The demineralized bone pieces then undergo a standard liming procedure and the resulting materials are washed, and subsequently subjected to about four or five extractions, which generally take from about 4 to 8 hours each, at increased temperatures, which generally range from about 131-212° F. The resulting extracts, which generally contain from about 3-7% gelatin, are then filtered, concentrated in a vacuum, evaporated, chilled, extruded as noodles, and dried at a temperature generally ranging from about 86-140° F. The resulting dry gelatin can then be ground and blended to required or desired specifications.

Example 2

Capsules Containing Suspending Agents Comprising CardioAid™-M Phytosterols and CardioAid™-S Phytosterol Esters Experiments were performed whereby compositions of the invention in the form of capsules were produced in the manner described in Example 1, with the exception that the suspending agents were replaced by suspending agents comprising a combination of CardioAid™-M phytosterols and CardioAid™-S phytosterol esters. As a result of this replacement, a required dose of phytosterols and/or phytosterol esters to meet FDA health claim requirements (described in 21 CFR §101.83), as well as a good suspension, were successfully achieved.

The combinations of CardioAid™-M phytosterols and CardioAid™-S phytosterol esters that achieved the foregoing results in three different trials are set forth below, with the optimum combination being that set forth under Trial No. 2, which had the desired suspension properties and flow characteristics for encapsulation, and met the FDA requirements for a health claim.

|  | Mg Per Capsule | | |
| --- | --- | --- | --- |
| Suspending Agent | Trial No. 1 | Trial No. 2 | Trial No. 3 |
| CardioAid ™-M Phytosterols | 57.7 | 105.3 | 158.0 |
| CardioAid ™-S Phytosterol Esters | 357.2 | 178.6 | 89.3 |

Example 3

Suppositories Containing Suspending Agents Comprising Phytosterols and Phytosterol Esters Compositions of the invention in the form of suppositories that contain phytosterols and phytosterol esters may be produced in the manner described below, which is a preferred method for producing compositions of the invention.

Phytosterols (M or Plain) are added to an electric heating kettle and heated to a temperature ranging between about 275° F. and about 293° F. Phytosterol esters are added to the heated phytosterols, and mixed therewith slowly until a melted and uniform mixture is produced, while maintaining a temperature of about 104° F.

Fish oil (edible oil) is added to a separate tank having a heating jacket, a nitrogen blanket and a propeller mixer, and then heated to a temperature ranging from about 80° F. to about 85° F. while mixing the oil. Antioxidants, emulsifiers and a powder pre-mix of vitamins and minerals are then added to the fish oil. The melted phytosterol/phytosterol ester blend is then slowly added to the mixture, and then mixed with the mixture for about 15 minutes.

The mixture is then transferred to a holding tank by pumping it through a homogenizer. The mixture is deaerated by placing the holding tank on a vacuum chamber for about 20 minutes at from about 20 to about 30 inches of mercury on the vacuum gage, and then permitted to cool to a temperature ranging from about 75° F. to about 80° F.

Using a commercially-available filling apparatus, hollow gel capsules are then filled with the above mixture while maintaining slow mixing and a nitrogen blanket to produce a series of suppositories.

Specific Preferred Embodiments

Other preferred embodiments of the compositions of the invention comprise specific combinations of two or more ingredients. These embodiments of the invention include, for example, the following combinations: (a) one fatty acid or other edible oil with one vitamin and/or mineral; (b) one fatty acid or other edible oil with more than one vitamin and/or mineral; (c) two or more fatty acids or other edible oils with one vitamin and/or mineral; (d) two or more fatty acids or other edible oils with two or more vitamins and/or minerals; or (e) any of (a)-(d), optionally, in combination with one or more other ingredients that are suitable for use in an oral pharmaceutical or other oral dosage composition, or in suppositories, and that do not prevent, or substantially reduce, the effectiveness of the compositions. Any one or more of the vitamins may be in a solid state, a solubilized state, or some other state, and various compositions of the invention may include both solid state and/or solubilized vitamins. In addition, the quantities of the one or more fatty acids and/or other edible oils and vitamins and/or minerals that may be employed in these compositions need not be the same. For example, the compositions may contain a larger quantity of EPA than DHA (or other fatty acids), a larger quantity of DHA than EPA (or other fatty acids), etc. As another example, the compositions may contain a larger quantity of one of the B vitamins, such as B6, B9 or B12, than another B or other vitamin, or more vitamin B6 than either vitamin B9 or B12, or any combination thereof.

As further examples, compositions within the invention may include one edible oil and vitamins B6, B9 and B12 (one edible oil and three different B vitamins), more than one edible oil and any one vitamin B, more than one edible oil and vitamins B6, B9, and B12 (more than one edible oil and three different B vitamins), or any combination thereof.

As still further examples, compositions within the invention may include one or more edible oils, for example fish oil and/or sunflower oil, with vitamin C alone or in combination with B6, B9, and/or B12 admixed therein, and with one or more oil soluble vitamins, for example vitamin A, dissolved in the fish oil or other edible oil. Other oil soluble vitamins may be dissolved in the edible oil, including but not limited to vitamins D, E, and K.

Emulsions

The compositions of the invention may also be in the form of an emulsion, such as a water-in-oil emulsion, an oil-in-water emulsion, an oil-in-water-in-oil emulsion, or the like, with at least one of the phases of the emulsion including the one or more vitamins and/or minerals suspended (if solid-state particles) or dissolved therein.

The compositions of the invention, in the form of emulsions, may be prepared using any edible or suitable emulsifier (any edible or suitable substance that aids in the formation and/or maintenance of an emulsion), such as egg yolk or egg lecithin, and standard emulsification techniques and equipment known by those of skill in the art. For example, water-in-oil emulsions may generally be formed by hand or mechanical stirring or whisking of the continuous and disperse phases of the emulsions for a period of time, and at strength, that permits the aqueous phase to break down into droplets, which are preferably small in size.

Other emulsions may be formed by slowly adding one or more ingredients employed in the compositions of the invention to one or more other ingredients while simultaneously mixing the ingredients rapidly. This disperses and suspends tiny droplets of one liquid throughout another liquid. The two liquids would generally rapidly separate if an emulsifier were not added to the mixture. Emulsifiers generally function as liaisons between two liquids and serve to stabilize the resulting mixture. Eggs and gelatin are among the foods that contain emulsifiers. Chemically, emulsions are colloids, heterogeneous mixtures composed of tiny particles suspended in another immiscible (unmixable) material. These particles are larger than molecules, but less than about one one-thousandth of a millimeter (0.001 mm). Particles having such a size generally do not settle out of an emulsion and can pass through filter paper. The particles in a colloid can be solid, liquid or bubbles of gas. The medium that they are suspended in can be a solid, liquid or gas (although gas colloids cannot be suspended in gas). Emulsions are liquid-liquid colloids, tiny liquid droplets suspended in another liquid. Emulsions are usually thick in texture and satiny in appearance. Microemulsions, which are special kinds of stabilized emulsions in which the dispersed droplets are extremely small (<100 nm), and which are thermodynamically stable, may also be used. A solid emulsion, which is a colloidal dispersion of a liquid in a solid, such as opal or pearl, may also be used.

Additional information concerning emulsification techniques, equipment and ingredients that may be employed to prepare compositions of the invention is present in S. Friberg et al., *Food Emulsions* (Marcel Dekker, $3^{rd}$ Rev. Ex Ed., 1997), and in V. Vaclavik et al., *Essentials of Food Science* (Kluwer Academic/Plenum Publishers, $2^{nd}$ Ed., 2003).

Packaging

The compositions of the invention are preferably packaged in a partially or totally opaque container. The package may include a label that indicates how to administer the compositions, for example, the daily dosage, the dosing regimen, whether to take the composition with food or on an empty stomach, whether to avoid taking the composition with alcoholic beverages, etc.

Shelf Life

Compositions within the present invention generally have a shelf life of about two years under room temperature conditions.

All of the edible oils, other materials and equipment employed in the example, and generally employed to make and use the compositions of the present invention, and to carry out the methods of the present invention, are commercially available from sources known by those of skill in the art, such as Cargill, Incorporated (Minneapolis, Minn.), BASF Corp. (Mt. Olive, N.J.), RFI Ingredients (Blauvelt, N.Y.), Hoffmann-LaRoche Inc. (Nutley, N.J.), Martek Corp. (Columbia, Md.), Ocean Nutrition Canada, Ltd. (Bedford, Nova Scotia, Canada), Pronova Biocare AS (Lysakar, Norway), Napro AS (Brattvaag, Norway), DSM (Heerlen, NL), Berg Lipotech AS (Norway), ADM Food Oils (Decatur, Ill.), Oilseeds International, Ltd. (San Francisco, Calif.), Post Apple Scientific (North East, Pa.) and the other sources described herein.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the invention be limited only by the scope of the claims which follow, and that such claims be interpreted as broadly as is reasonable.

Throughout this document, various books, patents, journal articles, web sites, federal regulations and other publications have been cited. The entireties of each of these books, patents, journal articles, web sites, federal regulations and other publications are hereby incorporated by reference herein.

What is claimed is:

1. A composition in an oral dosage form for an oral administration to a mammal, or in a form of a suppository, consisting essentially of:
    (a) one or more vitamins or minerals, or a combination thereof, in a combined amount that is effective for providing or enhancing one or more nutritional, medical or other health benefits, or a combination thereof, to a mammal, wherein the one or more vitamins are vitamin B6, vitamin B9 or vitamin B12, or combination thereof, are water-soluble and oil-insoluble, are initially in a solid-state form, are exogenous to one or more edible oils that may be included in the composition and are in a form that is capable of being mixed with one or more edible oils;

(b) one or more edible oils, or a combination thereof, in a combined amount that is effective for permitting the one or more vitamins or minerals, or combination thereof, to be mixed with the one or more edible oils, or combination thereof, said one or more edible oils substantially omega-3 fatty acids, omega-6, or omega-9 fatty acids, or a combination thereof, containing docosahexaenoic acid (DHA) in an amount greater than about 50 weight percent of the total weight of the edible oils, wherein said DHA is present in a triglyceride form and the one or more edible oils, or combination thereof, includes one or more substances that can provide a nutritional, medical or other health benefit, or a combination thereof, to a mammal;

(c) one or more edible suspending agents, or a combination thereof, in a combined amount that is effective for initiating, enhancing or maintaining a suspension of the one or more vitamins or minerals, or combination thereof, in the one or more edible oils, or combination thereof, or for providing a nutritional, medical or other health benefit, or a combination thereof, to a mammal, or both, wherein the one or more edible suspending agents, or a combination thereof, selected from the group consisting of phytosterols, phytosterol esters, plant stanols or plant stanol esters, or a combination thereof;

(d) one or more edible hollow oral dosage forms or hollow suppository forms;

wherein the one or more vitamins or minerals, or combination thereof, are admixed with the one or more edible oils, or combination thereof, or the one or more suspending agents, or combination thereof, or both; and wherein the one or more vitamins or minerals, or combination thereof, the one or more edible oils, or combination thereof, and the one or more edible suspending agents, or combination thereof, are present in the composition in a form of a suspension, wherein the one or more vitamins or minerals, or combination thereof, are at least temporarily suspended in the one or more edible oils, or combination thereof;

wherein the suspension or dispersion is inserted into the one or more edible hollow oral dosage forms or hollow suppository forms, or is formed into a solid suppository, to provide one or more unit dosage forms of the composition; and wherein a substantially uniform quantity of the one or more vitamins or minerals, or combination thereof, and the one or more edible oils, or combination thereof, is present in the one or more unit dosage forms, and wherein said composition is in a unit dosage form.

2. A composition of claim 1 wherein the one or more edible suspending agents include a combination of at least two or more of phytosterols, phytosterol esters, plant stanols and plant stanol esters.

3. A composition of claim 1 wherein the one or more edible suspending agents are beta-sitosterol, campesterol, stigmasterol, brassicasterol, or sitostanol, or a combination thereof.

4. A composition of claim 1 wherein the one or more edible suspending agents additionally include Sunflower oil, yellow or other beeswax or lecithin, or a combination thereof.

5. A composition of claim 1 wherein the one or more edible oils include one or more marine oils.

6. A composition of claim 1 wherein the one or more fatty acids are essential fatty acids.

7. A composition of claim 1 wherein the one or more fatty acids are omega-3 fatty acids.

8. A composition of claim 1 wherein the one or more fatty acids are DHA, eicosapentaenoic acid (EPA), alpha-linolenic acid (ALA), Arachidonic acid (ARA or AA) or gamma-linolenic acid (GLA), or a combination thereof.

9. A composition of claim 8 wherein the one or more omega-3 fatty acids are DHA, EPA or ALA, or a combination thereof.

10. A composition of claim 1 wherein the composition is an oral dosage form, and wherein the one or more vitamins or minerals, or combination thereof, have an ability to travel through an acidic environment of a stomach and into an intestinal tract of the mammal without being substantially degraded, and to be absorbed by the body of the mammal.

11. A composition of claim 1 wherein the one or more vitamins or minerals, or combination thereof, and the one or more edible oils, or combination thereof, are at least initially in the composition in a form of a suspension.

12. A composition of claim 11 wherein the suspension is substantially homogeneous, and is capable of remaining in a form of a substantially homogenous suspension at least for a period of time that is required to partially, substantially or fully fill one or more edible hollow oral dosage forms or hollow suppository forms with the suspension during a process for producing soft-gel, hard-gel or other capsules, other oral dosage forms or suppositories.

13. A composition of claim 1 wherein the one or more vitamins or minerals, or combination thereof, and the one or more edible oils, or combination thereof, are present in the composition in a form of a dispersion.

14. A composition of claim 1 wherein the composition additionally comprises one or more vitamins or minerals that are oil-soluble, or a combination thereof.

15. A composition of claim 14 wherein the one or more oil-soluble vitamins or minerals, or combination thereof, include vitamin D, vitamin E or vitamin K, or a combination thereof.

16. A composition of claim 15 wherein the one or more oil-soluble vitamins or minerals, or combination thereof, are exogenous to the one or more edible oils, and wherein the one or more oil-soluble vitamins or minerals, or combination thereof, are substantially dissolved in the one or more edible oils or are otherwise mixed therewith.

17. A composition of claim 1 wherein one or more edible antioxidant agents, or a combination thereof, are included in the composition, and wherein the one or more edible antioxidant agents, or combination thereof, are admixed with the one or more vitamins or minerals, or combination thereof, and the one or more edible oils, or combination thereof.

18. A composition of claim 1 wherein the vitamins or minerals, or combination thereof, are coated with one or more edible oils, or a combination thereof.

19. A composition of claim 1 wherein the composition includes Vitamin B9, and wherein the vitamin B9 is in the form of L-5-methyltetrahydrofolate, (6S)-tetrahydrofolic acid, 5 methyl-(6S)-tetrahydrofolic acid, 5 formyl-(6S)-tetrahydrofolic acid, 10 formyl-(6R)-tetrahydrofolic acid, 5,10-methylene-(6R)-tetrahydrofolic acid, 5,10-methenyl-(6R)- tetrahydrofolic acid, 5-formimino-(6S)-tetrahydrofolic acid, (6S)-5-methyltetrahydrofolic acid or a polyglutamyl derivative of tetrahydrofolate.

20. A composition of claim 1 wherein the composition includes vitamin B12, and wherein the vitamin B12 is in the form of cyanocobalamin, cobalamin or cobalamin bound to recombinant intrinsic factor.

21. A composition of claim 1 wherein the composition includes vitamin B12 and wherein the vitamin B12 is triturated with anhydrous ascorbic acid.

22. A composition of claim 1 wherein the one or more edible suspending agents include a combination of two or more of phytosterols, phytosterol esters, plant stanols and plant stanol esters.

23. A composition of claim 1 wherein the composition includes a substantially uniform mixture of two or more of vitamin B6, vitamin B9 or vitamin B12, in any combination, and wherein components or particles that are present in the substantially uniform mixture are coated with, and at least initially suspended within, one or more omega-3 oils, or a combination thereof.

24. A composition of claim 23 wherein the substantially uniform mixture of two or more of vitamin B6, vitamin B9 or vitamin B12, in any combination, is a finely divided substantially uniformly mixed powder.

25. A composition of claim 1 wherein the composition is in an oral dosage form, and wherein the oral dosage form is a soft-gel or hard-gel capsule.

26. A composition of claim 1 wherein the composition is in a form of a suppository.

27. A composition of claim 1 wherein the composition has a shelf life of about two years under room temperature conditions.

28. A composition of claim 1 wherein the one or more unit dosage forms include: (a) a combined amount of about 700 mg of the one or more edible oils, including about 500 mg of omega-3 oil, about 350 mg of which is DHA and about 35 mg of which is EPA; (b) about 12.5 mg of vitamin B6, about 500 μg of vitamin B12 and about 1000 μg of vitamin B9; 283.9 mg of a combination of beta-sitosterol, campesterol, stigmasterol, brassicasterol, and sitostanol; and (d) a trace amount of tocopherol.

29. A composition of claim 1 wherein the one or more edible oils, or combination thereof, are present in the composition in a combined amount ranging from about 0.01 to about 90 weight percent and the one or more suspending agents, or combination thereof, are present in the composition in an amount ranging from about 1 to about 60 weight percent.

30. A composition of claim 1 wherein the composition includes vitamin B6 in an amount ranging from about 1 mg to about 50 mg, vitamin B9 in an amount ranging from about 100 μg to about 1000 μg, and vitamin B12 in an amount ranging from about 200 μg to about 2000 μg.

31. A composition for an oral administration to a mammal consisting essentially of:
(a) one or more solid-state particles of one or more water-soluble vitamins or minerals, or a combination thereof, wherein the one or more vitamins are vitamin B6, vitamin B9 or vitamin B12, or a combination thereof, in a combined amount that is effective for providing or enhancing a nutritional, medical or other health benefit to the mammal;
(b) one or more edible oils, or a combination thereof, wherein the one or more edible oils substantially omega-3 fatty acids, omega-6 fatty acids or omega-9 fatty acids, or a combination thereof, and are in a combined amount that is effective for permitting the solid-state particles to be at least temporarily suspended therein, said one or more edible oils containing DHA in an amount greater than about 50 weight percent of the total weight of the edible oils and said DHA is present in a triglyceride form; and
(c) one or more edible suspending agents, or a combination thereof, in a combined amount that is effective for initiating, enhancing or maintaining a suspension of the one or more vitamins or minerals, or combination thereof, in the one or more edible oils, or for providing a nutritional, medical or other health benefit, or a combination thereof, to a mammal, or both, wherein the one or more edible suspending agents, or a combination thereof, selected from the group consisting of phytosterols, phytosterol esters, plant stanols or plant stanol esters, or a combination thereof; wherein the solid-state particles are admixed with the one or more edible oils, or combination thereof, or are at least temporarily suspended therein; and wherein said composition is in a unit dosage form.

32. A composition of claim 31 wherein the composition is included in a suppository.

33. A composition of claim 31 wherein the oral unit dosage form is a gelatin capsule.

34. A composition of claim 31 further comprising one or more antioxidant agents, or combination thereof, in an amount that is effective for preventing or reducing an oxidation, degradation or decomposition of the one or more water-soluble vitamins or minerals, or combination thereof, or the one or more edible oils, or combination thereof, wherein the one or more antioxidant agents, or combination thereof, are admixed with the one or more water-soluble vitamins or minerals, or combination thereof, and the one or more edible oils, or combination thereof.

35. A composition of claim 31 wherein the composition is in an oral unit dosage form, and wherein the water-soluble vitamins or minerals, or combination thereof, are coated with the one or more edible oils, or combination thereof, and have an enhanced ability to travel through a stomach to an intestinal tract of the mammal without being substantially degraded.

36. A composition of claim 31 further comprising one or more oil-soluble vitamins or minerals, or a combination thereof.

37. A composition for an oral administration, or an administration in a suppository, to a mammal consisting essentially of:
(a) one or more solid-state particles of one or more water-soluble vitamins wherein the one or more water-soluble vitamins are vitamin B6, vitamin B9 or vitamin B12, or a combination thereof, and wherein the one or more water-soluble vitamins, or combination thereof, are in a combined amount that is effective for providing or enhancing a nutritional, medical or other health benefit to the mammal;
(b) one or more edible oils, or a combination thereof, wherein the one or more edible oils substantially omega-3 fatty acids, omega-6 fatty acids or omega-9 fatty acids, in a combined amount that is effective for providing or enhancing a nutritional, medical or other health benefit to the mammal, said one or more edible oils containing DHA in an amount greater than about 50 weight percent of the total weight of the edible oils and said DHA is present in a triglyceride form; and
(c) one or more edible suspending agents, or a combination thereof, in a combined amount that is effective for initiating, enhancing or maintaining a suspension of the one or more solid-state particles of the one or more water-soluble vitamins, or combination thereof, in the one or more edible oils, or combination thereof, or for providing a nutritional, medical or other health benefit, or a combination thereof, to a mammal, or both, wherein the one or more edible suspending agents, or a combination thereof, selected from the group consisting of phytosterols, phytosterol esters, plant stanols or plant stanol esters, or a combination thereof;

wherein the solid-state particles are mixed with the one or more edible oils, or combination thereof, or are at least temporarily suspended therein; and wherein said composition is in a unit dosage form.

38. A composition of claim 37 wherein the composition is included within an oral unit dosage form.

39. A composition of claim 37 wherein the composition is included in a suppository.

40. A composition of claim 37 wherein the oral unit dosage form is a gelatin capsule.

41. A composition of claim 37 wherein the one or more omega-3 fatty acids is DHA, EPA or ALA, or a combination thereof.

42. A composition of claim 37 wherein the composition includes Vitamin B9, and wherein the vitamin B9 is in the form of L-5-methyltetrahydrofolate, (6S)-tetrahydrofolic acid, 5 methyl-(6S)-tetrahydrofolic acid, 5 formyl-(6S)-tetrahydrofolic acid, 10 formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, (6S)-5-methyltetrahydrofolic acid or a polyglutamyl derivative of tetrahydrofolate.

43. A composition of claim 37 wherein the composition includes vitamin B12, and wherein the vitamin B12 is in the form of cyanocobalamin, cobalamin or cobalamin bound to recombinant intrinsic factor.

44. A composition of claim 37 wherein the composition includes vitamin B12 and wherein the vitamin B12 is triturated with anhydrous ascorbic acid.

45. A composition of claim 37 wherein the one or more solid-state particles of the one or more water-soluble vitamins or minerals, or combination thereof, are coated with the one or more edible oils, or a combination thereof.

46. A composition of claim 37 wherein the composition includes a combination or two or more suspending agents.

47. A composition of claim 46 wherein the suspending agents additionally include Sunflower oil, yellow or other beeswax or lecithin, or a combination thereof.

48. A composition of claim 46 wherein the two or more suspending agents include a combination of two or more of phytosterols, phytosterol esters, plant stanols or plant stanol esters.

49. A composition of claim 37 wherein the composition is in an oral dosage form, and wherein the water-soluble vitamins or minerals, or combination thereof, have an enhanced ability to travel through a stomach to an intestinal tract of the mammal without being substantially degraded.

50. A composition of claim 37 further comprising one or more oil-soluble vitamins or minerals, or a combination thereof.

51. A composition of claim 37 wherein the composition includes vitamin B6 in an amount ranging from about 1 mg to about 50 mg, vitamin B9 in an amount ranging from about 100 µg to about 1000 µg, and vitamin B12 in an amount ranging from about 200 µg to about 2000 µg.

52. A method for producing a composition in an oral dosage form for an oral administration to a mammal, or in a form of a suppository, consisting essentially of:

(a) providing one or more vitamins or minerals, or a combination thereof, in a combined amount that is effective for providing or enhancing one or more nutritional, medical or other health benefits, or a combination thereof, to a mammal, wherein the one or more vitamins or minerals are vitamin B6, vitamin B9 or vitamin B12, or combination thereof, are water-soluble and oil-insoluble, are initially in a solid-state form, are exogenous to one or more edible oils that may be included in the composition and are in a form that is capable of being mixed with one or more edible oils;

(b) providing one or more edible oils, or a combination thereof, in a combined amount that is effective for permitting at least some of the one or more vitamins or minerals, or combination thereof, to be mixed therewith, or at least temporarily suspended therein, or for forming a continuous or disperse phase of a dispersion, wherein the one or more edible oils, or combination thereof, said one or more edible oils substantially omega-3 fatty acids, omega-6, or omega-9 fatty acids, or a combination thereof, containing DHA in an amount greater than about 50 weight percent of the total weight of the edible oils, wherein said DHA is present in a triglyceride form includes one or more substances that can provide a nutritional, medical or other health benefit, or a combination thereof, to a mammal;

(c) providing one or more edible suspending agents, or a combination thereof, in a combined amount that is effective for initiating, enhancing or maintaining a suspension of the one or more vitamins or minerals, or combination thereof, in the one or more edible oils, or combination thereof, or for providing a nutritional, medical or other health benefit, or a combination thereof, to a mammal, or both, wherein the one or more edible suspending agents, or a combination thereof, selected from the group consisting of phytosterols, phytosterol esters, plant stanols or plant stanol esters, or a combination thereof;

(d) providing one or more edible hollow oral dosage forms or hollow suppository forms;

(e) optionally, mixing the one or more vitamins or minerals, or combination thereof, for a period of time and under conditions that are effective for producing a substantially uniform mixture of the one or more vitamins or minerals, or combination thereof;

(f) optionally, mixing the one or more vitamins or minerals, or combination thereof, with an amount of an aqueous liquid, and for a period of time and under conditions, that are effective for forming an aqueous solution;

(g) optionally, mixing the one or more edible oils, or combination thereof, for a period of time and under conditions that are effective for producing a uniform mixture of the one or more edible oils, or combination thereof, (h) optionally, mixing the one or more edible suspending agents, or combination thereof, for a period of time and under conditions that are effective for producing a uniform mixture of the one or more edible suspending agents;

(i) combining the one or more vitamins or minerals, or combination thereof, with the one or more edible oils, or combination thereof, or the one or more edible suspending agents, or combination thereof, or both, for a period of time and under conditions that are effective for:

(i) producing a suspension of at least some of the one or more vitamins or minerals, or particles or combination thereof, in the one or more edible oils, or combination thereof, wherein the one or more vitamins or minerals, or particles or combination thereof, and the one or more edible oils, or combination thereof, remain in suspension for at least a period of time that is sufficient to enable the one or more edible hollow dosage forms or hollow suppository forms to be partially or fully filled with the suspension; or (ii) producing a dispersion; and (j) inserting the suspension or dispersion into the one or more edible hollow oral dosage forms or hollow suppository forms, or forming a solid suppository therewith, in an amount that is effective for partially or fully filling the one or more edible hollow oral dosage forms or hollow suppository forms so as to form one or more unit dosage forms, wherein substantially the same quantity of each of the components that are present in the composition becomes present in each of the one or more unit dosage forms.

53. A method of claim 52 wherein the one or more edible suspending agents include a combination of two or more of phytosterols, phytosterol esters, plant stanols or plant stanol esters.

54. A method of claim 52 wherein the one or more edible suspending agents are beta-sitosterol, campesterol, stigmasterol, brassicasterol, or sitostanol, or a combination thereof.

55. A method of claim 52 wherein the one or more edible suspending agents additionally include Sunflower oil, yellow or other beeswax or lecithin, or a combination thereof.

56. A method of claim 52 wherein the one or more edible oils includes one or more marine oils.

57. A method of claim 52 wherein the one or more fatty acids are essential fatty acids.

58. A method of claim 52 wherein the one or more fatty acids are omega-3 fatty acids.

59. A method of claim 52 wherein the one or more fatty acids are DHA, EPA, ALA, ARA, AA or GLA, or a combination thereof.

60. A method of claim 58 wherein the one or more omega-3 fatty acids are DHA, EPA or ALA, or a combination thereof.

61. A method of claim 52 wherein the composition is in an oral dosage form, and wherein the one or more vitamins or minerals, or combination thereof, have an enhanced ability to travel through an acidic environment of a stomach and into an intestinal tract of the mammal without being substantially degraded, and to be absorbed by the body of the mammal.

62. A method of claim 52 wherein the one or more vitamins or minerals, or combination thereof, and the one or more edible oils, or combination thereof, are combined in a manner that at least initially produces a suspension.

63. A method of claim 62 wherein the suspension is substantially homogeneous, and is capable of remaining in a form of a substantially homogenous suspension at least for a period of time that is required to partially, substantially or fully fill one or more edible hollow oral dosage forms or hollow suppository forms with the suspension during a process for producing soft-gel, hard-gel or other capsules, other oral dosage forms or suppositories.

64. A method of claim 52 wherein the one or more vitamins or minerals, or combination thereof, and the one or more edible oils, or combination thereof, are combined in a manner that produces a dispersion.

65. A method of claim 52 wherein the method additionally comprises the step of providing one or more vitamins or minerals that are oil-soluble, or a combination thereof.

66. A method of claim 65 wherein the one or more oil-soluble vitamins or minerals, or combination thereof, include vitamin D, vitamin E or vitamin K, or a combination thereof.

67. A method of claim 65 wherein the one or more oil-soluble vitamins or minerals, or combination thereof, are exogenous to the one or more edible oils, and wherein the one or more oil-soluble vitamins or minerals, or combination thereof, are substantially dissolved in the one or more edible oils or are otherwise mixed therewith.

68. A method of claim 52 wherein one or more edible antioxidant agents, or a combination thereof, are provided, and wherein the one or more edible antioxidant agents, or combination thereof, are admixed with the one or more vitamins or minerals, or combination thereof, and the one or more edible oils, or combination thereof.

69. A method of claim 52 wherein the vitamins or minerals, or combination thereof, are coated with one or more edible oils, or a combination thereof.

70. A method of claim 52 wherein the composition includes Vitamin B9, and wherein the vitamin B9 is in the form of L-5-methyltetrahydrofolate, (6S)-tetrahydrofolic acid, 5 methyl-(6S)-tetrahydrofolic acid, 5 formyl-(6S)-tetrahydrofolic acid, 10 formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, (6S)-5-methyltetrahydrofolic acid or a polyglutamyl derivative of tetrahydrofolate.

71. A method of claim 52 wherein the composition includes vitamin B12, and wherein the vitamin B12 is in the form of cyanocobalamin, cobalamin or cobalamin bound to recombinant intrinsic factor.

72. A method of claim 52 wherein the composition includes vitamin B12 and wherein the vitamin B12 is triturated with anhydrous ascorbic acid.

73. A method of claim 52 wherein the one or more edible suspending agents include a combination of two or more of phytosterols, phytosterol esters, plant stanols and plant stanol esters.

74. A method of claim 52 wherein the composition includes a substantially uniform mixture of two or more of vitamin B6, vitamin B9 or vitamin B12, in any combination, and wherein components or particles that are present in the substantially uniform mixture are coated with, and at least initially suspended within, one or more omega-3 oils, or a combination thereof.

75. A method of claim 74 wherein the substantially uniform mixture of two or more of vitamin B6, vitamin B9 or vitamin B12, in any combination, is a finely divided substantially uniformly mixed powder.

76. A method of claim 52 wherein the composition is in an oral dosage form, and wherein the oral dosage form is a soft-gel or hard-gel capsule.

77. A method of claim 52 wherein the composition is in a form of a suppository.

78. A method of claim 52 wherein the composition has a shelf life of about two years under room temperature conditions.

79. A method of claim 52 wherein the one or more unit dosage forms include:

(a) a combined amount of about 700 mg of the one or more edible oils, including about 500 mg of omega-3 oil, about 350 mg of which is DHA and about 35 mg of which is EPA;

(b) about 12.5 mg of vitamin B6, about 500 μg of vitamin B12 and about 1000 μg of vitamin B9;

(c) about 105.3 mg of a combination of beta-sitosterol, campesterol, stigmasterol, brassicasterol, and sitostanol; and (d) a trace amount of tocopherol.

80. A method of claim 52 wherein the components that are included in the composition, with the exception of the one or more edible hollow oral dosage forms or hollow suppository forms, are mixed, shaken or circulated together at least one time prior to inserting the components into the one or more edible hollow oral dosage forms or hollow suppository forms in a manner that permits substantially a uniform quantity of the components to be included in each of the one or more edible hollow oral dosage forms or hollow suppository forms.

81. A method of claim 52 wherein the one or more edible oils, or combination thereof, are present in the composition in a combined amount ranging from about 0.01 to about 90 weight percent and the one or more suspending agents, or combination thereof, are present in the composition in an amount ranging from about 1 to about 60 weight percent.

82. A composition of claim 52 wherein the composition includes vitamin B6 in an amount ranging from about 1 mg to about 50 mg, vitamin B9 in an amount ranging from about 100 µg to about 1000 µg, and vitamin B12 in an amount ranging from about 200 µg to about 2000 µg.

83. A method for preparing a composition for an oral administration to a mammal, or in a suppository, consisting essentially of:
    (a) providing one or more solid state particles of one or more water-soluble vitamins or minerals, or a combination thereof, wherein the one or more vitamins are vitamin B6, vitamin B9 or vitamin B12, or a combination thereof, in a combined amount that is effective for providing or enhancing a nutritional, medical or other health benefit to the mammal;
    (b) providing one or more edible oils, or a combination thereof, including one or more fatty acids in a combined amount that is effective for permitting the one or more water-soluble vitamins or minerals, or combination thereof, to be at least temporarily suspended therein said one or more edible oils substantially omega-3 fatty acids, omega-6, or omega-9 fatty acids, or a combination thereof, containing DHA in an amount greater than about 50 weight percent of the total weight of the edible oils, wherein said DHA is present in a triglyceride form and the one or more edible oils, or combination thereof;
    (c) providing one or more edible suspending agents, or a combination thereof, in a combined amount that is effective for initiating, enhancing or maintaining a suspension of the one or more solid state particles of the one or more water-soluble vitamins or minerals, or combination thereof, in the one or more edible oils, or combination thereof, or for providing a nutritional, medical or other health benefit, or a combination thereof, to a mammal, or both, wherein the one or more edible suspending agents, or a combination thereof, selected from the group consisting of phytosterols, phytosterol esters, plant stanols or plant stanol esters, or a combination thereof;
    (d) optionally, mixing the one or more water-soluble vitamins or minerals, or combination thereof, for a period of time and under conditions that are sufficient to produce a substantially uniform mixture of the one or more water-soluble vitamins or minerals, or combination thereof;
    (e) optionally, mixing the one or more edible oils, or combination thereof, for a period of time and under conditions that are sufficient to produce a substantially uniform mixture of the one or more edible oils, or combination thereof;
    (f) suspending, at least temporarily, an amount of the one or more water-soluble vitamins or minerals, or combination thereof, within an amount of the one or more edible oils, or combination thereof, that is effective for producing a suspension of the solid-state particles of the one or more water-soluble vitamins or minerals, or combination thereof, within the one or more edible oils, or mixtures thereof; and
    (g) injecting or inserting a resulting suspension into one or more oral dosage forms or hollow suppository forms, wherein the oral dosage forms are hard or soft capsules, gelatin capsules, caplets or gelatin caplets.

84. A method of claim 83 wherein vitamin B9 is provided and wherein the vitamin B9 is in the form of L-5-methyltetrahydrofolate, (6S)-tetrahydrofolic acid, 5 methyl-(6S)-tetrahydrofolic acid, 5 formyl-(6S)-tetrahydrofolic acid, 10 formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, (6S)-5-methyltetrahydrofolic acid or polyglutamyl derivatives of tetrahydrofolate.

85. A method of claim 83 wherein vitamin B12 is provided and wherein the vitamin B12 is in the form of cyanocobalamin, cobalamin or cobalamin bound to recombinant intrinsic factor.

86. A method of claim 83 wherein vitamin B12 is provided and wherein the vitamin B12 is triturated with anhydrous ascorbic acid.

87. A method of claim 83 wherein the one or more edible suspending agents, or combination thereof, is blended with the one or more edible oils, or combination thereof.

88. A method of claim 83 wherein the composition includes one or more omega-3 fatty acids and wherein the one or more omega-3 fatty acids are DHA, EPA or ALA, or combination thereof.

89. A method of claim 88 wherein the one or more edible suspending agents include a combination of two or more of phytosterols, phytosterol esters, plant stanols and plant stanol esters.

90. A method of claim 83 wherein the composition includes vitamin B6 in an amount ranging from about 1 mg to about 50 mg, vitamin B9 in an amount ranging from about 100 µg to about 1000 µg, and vitamin B12 in an amount ranging from about 200 µg to about 2000 µg.

91. A method for preparing a composition in an oral form for an oral administration to a mammal, or in a form of a suppository, consisting essentially of:
    (a) providing one or more solid-state particles of one or more water soluble vitamins or minerals, or a combination thereof, wherein the one or more vitamins are vitamin B6, vitamin B9 or vitamin B12, or a combination thereof, in a combined amount that is effective for providing or enhancing a nutritional, medical or other health benefit to the mammal;
    (b) mixing the solid-state particles in an amount of water that is sufficient to form an aqueous solution;
    (c) providing one or more edible emulsifiers, or a combination thereof;
    (d) providing one or more edible oils, or combination thereof, including one or more fatty acids, said one or more edible oils substantially omega-3 fatty acids, omega-6, or omega-9 fatty acids, or a combination thereof, containing DHA in an amount greater than about 50 weight percent of the total weight of the edible oils, wherein said DHA is present in a triglyceride form and the one or more edible oils, or combination thereof;
    (e) providing one or more edible suspending agents, or a combination thereof, in a combined amount that is effective for initiating, enhancing or maintaining a suspension of the one or more solid state particles of the one or more water-soluble vitamins or minerals, or combination thereof, in the one or more edible oils, or combination thereof, or for providing a nutritional, medical or other health benefit, or a combination thereof, to a mammal, or both, wherein the one or more edible suspending agents, or a combination thereof, selected from the group consisting of phytosterols, phytosterol esters, plant stanols or plant stanol esters, or a combination thereof;

(f) optionally, mixing the one or more edible oils, or combination thereof, for a period of time and under conditions that are sufficient to produce a uniform mixture of the one or more edible oils, or combination thereof;

(g) mixing the aqueous solution with the one or more edible emulsifiers, or combination thereof, and the one or more edible oils, or combination thereof, under conditions that are sufficient to form an emulsion; and (h) injecting or otherwise inserting the emulsion into one or more hollow oral dosage forms or hollow suppository forms, wherein the hollow oral dosage forms are soft or hard capsules, gelatin capsules, caplets or gelatin caplets.

92. A method for enhancing the quantity of one or more vitamins or minerals, or combination thereof, that are absorbed by an intestinal tract of a mammal and delivered to the mammal's body after the mammal consumes one or more vitamins or minerals, or combination thereof, comprising orally administering to the mammal a composition of claim 1 in an oral dosage form and in an amount that is effective for enhancing the quantity of one or more vitamins or minerals, or combination thereof, that are absorbed by the intestinal tract of the mammal and delivered to the mammal's body after the mammal consumes the composition.

93. A method for enhancing the nutrition, health or medical condition of a mammal comprising administering to the mammal orally, or in a suppository, a composition of claim 1 in an amount that is effective for enhancing the nutrition, health or medical condition of the mammal.

94. A method for enhancing the nutrition, health or medical condition of a mammal comprising:
   (a) providing an effective amount of a composition according to claim 1; and
   (b) administering the effective amount of a composition according to claim 1 to the mammal orally, or in a form of a suppository.

95. A method for enhancing the nutrition, health or medical condition of a mammal comprising:
   (a) providing an effective amount of a composition according to claim 37; and
   (b) administering the effective amount of the composition according to claim 37 to a mammal orally, or in a form of a suppository.

96. A composition in an oral dosage form for an oral administration to a mammal consisting essentially of:
   (a) one or more water-soluble vitamins or minerals, or a combination thereof, wherein the one or more vitamins are vitamin B6, vitamin B9 or vitamin B12, or a combination thereof, in a combined amount that is effective for providing or enhancing one or more nutritional, medical or other health benefits, or a combination thereof, to a mammal, wherein the one or more water-soluble vitamins or minerals, or combination thereof, are in a form that is capable of being mixed with one or more edible oils;
   (b) one or more edible oils, or a combination thereof, in a combined amount that is effective for permitting the one or more water-soluble vitamins or minerals, or combination thereof, to be mixed with the one or more edible oils, said one or more edible oils substantially omega-3 fatty acids, omega-6 fatty acids or omega-9 fatty acids, or a combination thereof, containing DHA in an amount greater than about 50 weight percent of the total weight of the edible oils and said DHA is present in a triglyceride form;
   (c) one or more edible suspending agents in a combined amount that is effective for initiating, enhancing or maintaining a suspension of the one or more water-soluble vitamins or minerals, or combination thereof, in the one or more edible oils, or for providing a nutritional, medical or other health benefit, or a combination thereof, to a mammal, or both, wherein the one or more suspending agents selected from the group consisting of phytosterols, phytosterol esters, plant stanols or plant stanol esters, or a combination thereof;
   (d) two or more edible hollow oral dosage forms;
   wherein the one or more water-soluble vitamins minerals, or combination thereof, and the one or more edible oils, or combination thereof, are present in the compositions in a manner or form that permits substantially a uniform quantity of the one or more water-soluble vitamins or minerals, or combination thereof, and the one or more edible oils, or combination thereof, to be inserted into each of the one or more hollow oral dosage forms, and wherein the one or more water-soluble vitamins or minerals, or combination thereof, has an ability to travel through an acidic environment of a stomach and into the intestinal tract of the mammal without being substantially or fully degraded, and to be absorbed by the body of the mammal.

97. The composition of claim 1 further comprising one or more edible antioxidant agents, or a combination thereof in a combined amount that is effective for preventing or reducing an oxidation, degradation or other decomposition of the one or more vitamins or minerals, or combination thereof, the one or more edible oils, or combination thereof, or one or more other components that are included in the composition, or any combination thereof.

98. The composition of claim 1 further comprising wherein the one or more edible diluents, or a combination thereof, in a combined amount that is effective for diluting, rendering less potent, thinning, weakening or facilitating a physical separation of one or more components that are included in the composition.

99. The composition of claim 1 further comprising one or more edible emulsifiers, or a combination thereof, in a combined amount that is effective for causing or enhancing a formation of an emulsion.

100. The composition of claim 1 further comprising one or more edible surfactants, or a combination thereof, in a combined amount that is effective for reducing a surface tension when dissolved or otherwise included in an aqueous liquid or reducing an interfacial tension between two liquids, or between a liquid and a solid.

101. The method of claim 52, between steps (d) and (e), further comprising: providing one or more edible antioxidant agents, or a combination thereof in a combined amount that is effective for preventing or reducing an oxidation, degradation or other decomposition of the one or more vitamins or minerals, or combination thereof, the one or more edible oils, or combination thereof, or one or more other components that are included in the composition, or any combination thereof.

102. The method of claim 52, between steps (d) and (e), further comprising: providing one or more edible diluents, or a combination thereof, in a combined amount that is effective for diluting, rendering less potent, thinning, weakening or facilitating a physical separation of one or more components that are included in the composition.

103. The method of claim 52, between steps (d) and (e), further comprising: providing one or more edible emulsifiers, or a combination thereof, in a combined amount that is effective for causing or enhancing a formation of an emulsion.

104. The method of claim 52, between steps (d) and (e), further comprising: providing one or more edible surfactants, or a combination thereof, in a combined amount that is effective for reducing a surface tension when dissolved or otherwise included in an aqueous liquid or reducing an interfacial tension between two liquids, or between a liquid and a solid.

105. The method of claim 52, after step (h), further comprising: combining the antioxidant agents, diluents, emulsifiers, surfactants or other optional ingredients, or combination thereof, with the one or more vitamins or minerals or the one or more edible oils, or with any combination thereof.

106. The composition of claim 96, wherein the one or more edible antioxidant agents, or a combination thereof in a combined amount that is effective for preventing or reducing an oxidation, degradation or other decomposition of the one or more vitamins or minerals, or combination thereof, the one or more edible oils, or combination thereof, or one or more other components that are included in the composition, or any combination thereof.

107. The composition of claim 96, wherein the one or more edible diluents, or a combination thereof, in a combined amount that is effective for diluting, rendering less potent, thinning, weakening or facilitating a physical separation of one or more components that are included in the composition.

108. The composition of claim 96, wherein the one or more edible emulsifiers, or a combination thereof, in a combined amount that is effective for causing or enhancing a formation of an emulsion.

\* \* \* \* \*